US012630589B2

(12) United States Patent
Avilés Marín et al.

(10) Patent No.: US 12,630,589 B2
(45) Date of Patent: May 19, 2026

(54) COMPOUNDS FOR USE IN VIRAL INFECTIONS

(71) Applicant: PHARMA MAR, S.A., Madrid (ES)

(72) Inventors: Pablo Avilés Marín, Madrid (ES); Alejandro Losada González, Madrid (ES); José María Fernández Sousa-Faro, Madrid (ES); Salvador Fudio Muñoz, Madrid (ES)

(73) Assignee: PHARMA MAR, S.A., Madrid (ES)

(*) Notice: Subject to any disclaimer, the term of this patent is extended or adjusted under 35 U.S.C. 154(b) by 682 days.

(21) Appl. No.: 17/908,533

(22) PCT Filed: Mar. 2, 2021

(86) PCT No.: PCT/EP2021/055147

§ 371 (c)(1),
(2) Date: Aug. 31, 2022

(87) PCT Pub. No.: WO2021/175831

PCT Pub. Date: Sep. 10, 2021

(65) Prior Publication Data

US 2023/0159594 A1 May 25, 2023

(30) Foreign Application Priority Data

| | | |
|---|---|---|
| Mar. 2, 2020 | (EP) | 20182152 |
| Mar. 13, 2020 | (EP) | 20182192 |
| Apr. 2, 2020 | (EP) | 20382266 |
| Apr. 27, 2020 | (EP) | 20382339 |
| Sep. 16, 2020 | (EP) | 20382815 |
| Sep. 16, 2020 | (EP) | 20382816 |
| Jan. 25, 2021 | (EP) | 21382059 |

(51) Int. Cl.

| | |
|---|---|
| ***C07K 11/02*** | (2006.01) |
| ***A61K 31/138*** | (2006.01) |
| ***A61K 31/341*** | (2006.01) |
| ***A61K 31/4178*** | (2006.01) |
| ***A61K 31/573*** | (2006.01) |
| ***A61K 38/15*** | (2006.01) |
| ***A61P 29/00*** | (2006.01) |
| ***A61P 31/14*** | (2006.01) |
| ***A61P 31/16*** | (2006.01) |
| ***A61P 31/18*** | (2006.01) |
| ***A61P 37/06*** | (2006.01) |
| *A61K 38/00* | (2006.01) |

(52) U.S. Cl.

CPC ............ *C07K 11/02* (2013.01); *A61K 31/138* (2013.01); *A61K 31/341* (2013.01); *A61K 31/4178* (2013.01); *A61K 31/573* (2013.01); *A61K 38/15* (2013.01); *A61P 29/00* (2018.01); *A61P 31/14* (2018.01); *A61P 31/16* (2018.01); *A61P 31/18* (2018.01); *A61P 37/06* (2018.01); *A61K 38/00* (2013.01)

(58) Field of Classification Search

None

See application file for complete search history.

(56) References Cited

U.S. PATENT DOCUMENTS

| | | | | |
|---|---|---|---|---|
| 4,493,796 | A | 1/1985 | Rinehart, Jr. | |
| 5,834,586 | A * | 11/1998 | Rinehart | A61P 35/00 930/DIG. 549 |
| 6,156,724 | A | 12/2000 | Rinehart | |
| 2012/0040033 | A1* | 2/2012 | Armstrong | A61P 31/12 514/23 |

FOREIGN PATENT DOCUMENTS

| | | | |
|---|---|---|---|
| WO | 91/04985 | A1 | 4/1991 |
| WO | 99/42125 | A1 | 8/1999 |
| WO | 2001/76616 | A1 | 10/2001 |
| WO | 2002/02596 | A2 | 1/2002 |
| WO | 2004/084812 | A2 | 9/2004 |
| WO | 2011/020913 | A2 | 2/2011 |
| WO | 2021/175857 | A1 | 9/2021 |

OTHER PUBLICATIONS

Bellini. Parasites and Vectors, 2014, 7:323, 1-11 (Year: 2014).*

Couch. The New England Journal of Medicine, 2000, 343 (24), 1778-1787 (Year: 2000).*

Anonymous, "West Nile virus disease therapeutics," CDC, 11 Pages, (Feb. 3, 2018).

Anonymous, "PharmaMar reports positive results for Aplidin® against coronavirus HCoV-229E," (Mar. 13, 2020).

Anonymous, "Boryung Pharmaceutical, PharmaMar's partner in South Korea, announces superior potent results for plitidepsin (Aplidin) against SARS-COV-2," (Jul. 2, 2020).

Anonymous, "PharmaMar has announced that the Spanish Medicines Agency has authorized the APLICOV-PC, clinical trial with Aplidin (plitidepsin) for the treatment of patients with COVID-19" 2 Pages, (Apr. 28, 2020).

Anonymous, History of Changes for Study: NCT04382066, "Proof of Concept Study to Evaluate the Safety Profile of Plitidepsin in Patients With COVID-19 (Aplicov-Pc)," (May 11, 2020).

Boryung Pharmaceutical, PharmaMar's partner in South Korea, announces superior potent results for plitidepsin (Aplidin®) against SARS-COV-2. Pharmamar Press Release (see https://pharmamar.com/en/company/newsroom/), Jul. 2, 2020.

Boryung Pharmaceutical Designates Orphan Drug for Small Cell Lung Cancer New Drug 'Rurbinectedin', Aug. 4, 2020.

Clinical Trials Study: NCT04382066, "Proof of Concept Study to Evaluate the Safety Profile of Plitidepsin in Patients With COVID-19 (Aplicov-Pc)," https://clinicaltrials.gov/ct2/show/NCT0438066, May 11, 2020.

(Continued)

*Primary Examiner* — Noble E Jarrell

(74) *Attorney, Agent, or Firm* — Ballard Spahr LLP

(57) ABSTRACT

The present invention relates to the use of compounds in the treatment of a viral infection, wherein the virus is selected from the Orthomyxoviridae family or wherein the virus is West Nile virus.

24 Claims, 18 Drawing Sheets

(56) References Cited

OTHER PUBLICATIONS

Clinical Trial information—APL-D-002-20 Multicenter, randomized, parallel and proof of concept study to evaluate the safety profile of three doses of Plitidepsin in patients with COVID-19 requiring hospitalization, Clinical trial publication, Mar. 22, 2021.
Communication to National Securities Market Commission (Registration No. 82) Pharmamar Press Release (see https://www.cnmv.es/Portal/verDoc.axd?t={bfcd6a1c-d209-42a6-8096-7a953198f8a1}), Mar. 3, 2020.
Communication to National Securities Market Commission (Registration No. 90) Pharmamar Press Release (see https://www.cnmv.es/Portal/verDoc.axd?t={67a1abfd-9477-4f3a-b030-ff7f5b2d958a}), Mar. 13, 2020.
Communication to National Securities Market Commission (Registration No. 188), Pharmamar Press Release (see https://www.cnmv.es/Portal/verDoc.axd?t={45a5606c-8cf9-420f-9ef1-5792f3cf697c}), Apr. 28, 2020.
Communication to National Securities Market Commission (Registration No. 496). Pharmamar Press Release (see https://www.cnmv.es/Portal/verDoc.axd?t={cbc13dcd-9dc3-4ccc-9185-a523a38e7827}), Oct. 16, 2020.
Communication to National Securities Market Commission (Registration No. 565) Pharmamar Press Release (see https://www.cnmv.es/Portal/verDoc.axd?t={3ca9678d-c53d-42a0-afec-e5fce5ccbbf3}), Nov. 10, 2020.
PharmaMar reports positive results for Aplidin® against coronavirus HCoV-229E, Pharmamar Press Release (see https://pharmamar.com/en/company/newsroom/), 2 Pages, Mar. 13, 2020.
PharmaMar has submitted a Phase II clinical trial of Aplidin® (plitidepsin) for the treatment of COVID-19 to the Spanish Medicines Agency, Pharmamar Press Release (see https://pharmamar.com/en/company/newsroom/), Apr. 2, 2020.
PharmaMar has announced that the Spanish Medicines Agency has authorized the APLICOV-PC clinical trial with Aplidin® (plitidepsin) for the treatment of patients with COVID-19, Pharmamar Press Release (see https://pharmamar.com/en/company/newsroom/), Apr. 28, 2020.
PharmaMar announces positive results of its APLICOV trial against COVID-19. Pharmamar Press Release (see https://pharmamar.com/en/company/newsroom/), Oct. 16, 2020.
The Peer Review journal Science confirms the potent activity of PharmaMar's plitidepsin against SARS-COV-2 Pharmamar Press Release (see https://pharmamar.com/en/company/newsroom/), Jan. 26, 2021.
UK approves the initiation of the Phase III Neptuno clinical trial with PharmaMar's Aplidin® (plitidepsin) for the treatment of patients with COVID-19, Pharmamar Press Release (see https://pharmamar.com/en/company/newsroom/), Feb. 17, 2021.
Stabio Pharma Australian Product Information APLIDIN (plitidepsin), 20 Pages, Dec. 10, 2018.
Al-Horani, R.A., et al., "Potential Anti-SARS-COV-2 Therapeutics That Target the Post-Entry Stages of the Viral Life Cycle: A Comprehensive Review," Viruses, 12(1092), v12101092, Sep. 23, 2020.
Ankisetty, S., et al., "Chlorinated Didemnins from the Tunicate Trididemnum solidum," Marine Drugs, 11(110): 4478-4486, Nov. 11, 2013.
Bairi, K.E., et al., "Repurposing anticancer drugs for the management of COVID-19," European Journal of Cancer, 141: 40-61 (2020).
Brönstrup, M., et al., "Natural products targeting the elongation phase of eukaryotic protein biosynthesis," Natural Product Reports, 37: 752-762 (2020).
Cavasotto, C., et al., "In silico Drug Repurposing for COVID-19 Targeting Sars COV-2 Proteins through Docking and Consensus Ranking," Molecular Informatics, 10.1002/minf.202000115, (2021).
Conte, M., et al., "Marine-Derived Secondary Metabolites as Promising Epigenetic Bio-Compounds for Anticancer Therapy," Therapy. Mar. Drugs 2021, 19, 15, 28 Pages, (2021) https://doi.org/10.3390/md19010015.
Davis, W.G., et al., "Interaction between the Cellular Protein eEF1A and the 3'-Terminal Stem-Loop of West Nile Virus Genomic RNA Facilitates Viral Minus-Strand RNA Synthesis," Journal of Virology, 8 1(18) 10172-10187 (2007).
Derosa, L., et al., "The immuno-oncological challenge of COVID-19," Nature Cancer, 1: 946-964, Oct. 2020.
Gatti, M., et al., "Drug Repurposing in the COVID-19 Era: Insights from Case Studies Showing Pharmaceutical Peculiarities," Pharmaceutics 13, 302, (2021), https://doi.org/10.3390/pharmaceutics13030302.
Getts, D.R., et al., "Ly6c+ "inflammatory monocytes" are microglial precursors recruited in a pathogenic manner in West Nile virus encephalitis," The Journal of Experimental Medicine, 205(10): 2319-2337 (2008).
Halford, B., "Plitidepsin could fight COVID-19," Cen.Acs. Org, 1 Page, Feb. 1, 2021.
Harrison, C., "Drug researchers pursue new lines of attack against COVID-19," Nature Biotechnology, 38: 655-664, Jun. 2020.
Kakeya, H., et al., "Steroid Drugs and Infectious Diseases," Japanese Journal of Internal Medicine, 108(11): 2268-2274 (2019).
Kalhotra, P., et al., "Field-Template, QSAR, Ensemble Molecular Docking, and 3D-RISM Solvation Studies Expose Potential of FDA-Approved Marine Drugs as SARS-CoVID-2 Main Protease Inhibitors," Molecules, 26(4), 936 (2021).
Kawai, T. et al., "Signaling to NF-KB by Toll-like receptors," Trends in Molecular Medicine; 13(11): 460-469 (2007).
Kumar, M., et al., "Pro-inflammatory cytokines derived from West Nile virus (WNV) -infected SK-N-SH cells mediate neuroinflammatory markers and neuronal death," Journal of Neuroinflammation, 7:73, 14 Pages (2010).
Lee, Y., et al., "Structural diversity of marine cyclic peptides and their molecular mechanisms for anticancer, antibacterial, antifungal, and other clinical applications," Peptides, 95: 94-105 (2017).
Leis, A.A., et al., "Lazarus Effect of High Dose Corticosteroids in a Patient With West Nile Virus Encephalitis: A Coincidence or a Clue?" Frontiers in Medicine, 6(81), pp. 1-3 (2019).
Li, H., et al., "Effect of low-to-moderate-dose corticosteroids on mortality of hospitalized adolescents and adults with influenza A(H1N1)pdm09 viral pneumonia," Influenza Other Respi. Viruses, 11: 345-354, Mar. 30, 2017.
Losada, A., et al., "Translation Elongation Factor eEF1A2 is a Novel Anticancer Target for the Marine Natural Product Plitidepsin," Scientific Reports, 6(1): pp. 1-15, Oct. 7, 2016.
Losada A., et al., "Binding of eEFIA2 to the RNA-dependent protein kinase PKR modulates its activity and promotes tumour cell survival," British Journal of Cancer, 119(11): 1410-1420, (2018).
Losada, A., et al., "Generation of endoplasmic reticulum stress and inhibition of autophagy by plitidepsin induces proteotoxic apoptosis in cancer cells," Biochemical Pharmacology, 172: 113744, 16 Pages (2020).
Luesch, H., et al., "Targeting and extending the eukaryotic druggable genome with natural products," Natural Product Reports, 37(6): 744-746 (2020).
Maroun, J.A., et al., "Phase I study of Aplidine in a dailyx5 one-hour infusion every 3 weeks in patients with solid tumors refractory to standard therapy. A National Cancer Institute of Canada Clinical Trials Group study: NCIC CTG IND 115,". Annals of Oncology, 17(9): 1371-1378 (2006).
Martinez, M.A., "Plitidepsin: a Repurposed Drug for the Treatment of COVID-19," Antimicrobial Agents Chemotherapy, 65(4), e00200-21, 3 Pages (2021), https://doi.org/10.1128/AAC.00200-21.
Mateos, M., et al. "Final Results of a Phase II Trial with Plitidepsin (Aplidin) Alone and in Combination with Dexamethasone in Patients with Relapsed/Refractory Multiple Myeloma," Blood, 112(11): 3700, 6 Pages (2008).
Mateyak, M.K., et al., "eEFI A: thinking outside the ribosome," The Journal of Biological Chemistry, 285(28): 21209-21213 (2010).

(56) References Cited

OTHER PUBLICATIONS

Nalda-Molina, R., et al., "Popultion pharmacokinetics meta-analysis of plitidepsin (Aplidin) in cancer subject," Cancer Chemother Pharmacol. 64(11): 97-108 (2009).
Ni, Y.N., et al., "The effect of corticosteroids on mortality of patients with influenza pneumonia: a systematic review and meta-analysis," Critical Care, 23(99): pp. 1-9 (2019).
Ranieri, V.M., et al., Acute respiratory distress syndrome: the Berlin Definition, JAMA, 307(23): 2526-2533 (2012).
Reuschl, A.K., et al., "Host-directed therapies against early-lineage SARS-COV-2 retain efficacy against B.1.1.7 variant,". bioRxiv preprint doi: https://doi.org/10.1101/2021.01.24.427991, Feb. 4, 2021.
Rinehart, Jr., K.L., et al., "Didemnins: Antiviral and Antitumor Depsipeptides from a Caribbean Tunicate," Science, 212: 933-935 (1981).
Rinehart, et al., "Biologically active peptides and their mass spectra," Pure and Applied Chemistry.54(12: 2409-2424 (1982).
Rinehart, K.L., "Antiviral Agents from Novel Marine and Terrestrial Sources", Innovations in Antiviral Development and the Detection of Viral Infection, pp. 41-60 (1992).
Rodon, J., et al., "Search for SARS-COV-2 inhibitors in currently approved drugs to tackle COVID-19 pandemia," BioRxiv, 19 Pages (2020), http://www.koreabiomed.com/news/articleView.html?idxno=8662.
Rodon, J., et al., "Preclinical search of SARS-COV-2 inhibitors and their combinations within approved drugs to tackle COVID-19 pandemic," BioRxiv, 38 Pages (2020), doi: https://doi.org/10.1101/2020.04.23.055756.
Rodon, J., et al., "Identification of Plitidepsin as Potent Inhibitor of SARS-COV-2-Induced Cytopathic Effect after a Drug Repurposing Screen," BioRxiv, 38 Pages (2021), https://doi.org/10.1101/2020.04.23.055756.
Rossi, S.L., et al., "West Nile Virus," Clin Lab Med., 30(1): 47-65 (2010).
Rossini, G., et al., "Innate host responses to West Nile virus: Implications for central nervous system immunopathology," World Journal of Virology,2(2): 49-56 (2013).
Sammaibashi, S., et al., "Strain-Specific Contribution of Eukaryotic Elongation Factor 1 Gamma to the Translation of Influenza A Virus Proteins," Frontiers in Microbiology, 9(1446): pp. 1-10 (2018).
Shim, H., "Boryung finds cancer drug has antiviral effect on Covid-19," Korea Biomedical Review, 3 Pages (2020).
Song, Z., et al., "EIF4A2 interacts with the membrane protein of transmissible gastroenteritis coronavirus and plays a role in virus replication, " Research in Veterinary Science, 123: 39-46 (2019).
Spicka, et al., "Randomized phase III study (ADMYRE) of plitidepsin in combination with dexamethasone vs. dexamethasone alone in patients with relapsed/refractory multiple myeloma.," Annals of Hematology, 98(9):2139-2150 (2019).
Stark G.R., et al., "How cells respond to interferons," Annu. Rev. Biochem., 67: 227-264 (1998).
Sultanta, J., et al., "Challenges for Drug Repurposing in the COVID-19 Pandemic Era," Frontiers in Pharmacology, 11 (Article 588654): 13 Pages (2020).
Suthar, M.S., et al., "West Nile virus infection and immunity," Nature Reviews Microbiology, 11(2): 115-28 (2013).
Taglialatela-Scafati, O., "New hopes for drugs against COVID-19 come from the sea," Marine Drugs (2021), 19, 104 (2021).
Tilvi, S., et al., "Marine-Derived Natural Products Inhibiting Specific Inflammatory Cytokines," Studies in Natural Products Chemistry, 62: 455-481, (2019).
Vera, M.S., et al., "Natural products as probes of cell biology: 20 years of didemnin research," Medicinal Research Reviews, 22(2): 102-145 (2002).
Wang, T., et al., "Toll-like receptor 3 mediates West Nile virus entry into the brain causing lethal encephalitis,". Nature Medicine, 10(12): 1366-1373 (2004).
White, K., et al., "Repurposing of clinically-approved drugs for the treatment of COVID-19, " Report from the isirv-AVG Virtual Conference, Oct. 6-8, 2020).
White, K.M., et al., "Plitidepsin has potent preclinical efficacy against SARS-CoV-2 by targeting the host protein eEF1A," Science, 371: 926-931 (2021).
Wong, J.P, et al., "SARS-CoV-2 dependence on host pathways," Science, 371(6532): 884-885 (2021), DOI: 10.1126/ science. abg6837.
Zhou, Y et al., "Use of corticosteroids in influenza-associated acute respiratory distress syndrome and severe pneumonia: a systemic review and meta-analysis," Scientific Reports 10 (3044), 10 Pages (2020).

* cited by examiner

COMPOUNDS FOR USE IN VIRAL INFECTIONS

FIELD OF THE INVENTION

The present invention relates to the treatment of viral infections from the Orthomyxoviridae family or wherein the virus is West Nile virus.

BACKGROUND TO THE INVENTION

Treating viral infections is not only important for reducing disease severity, but also for preventing disease and minimising viral transmission. For example, a number of viruses cause life-long infections that can be effectively managed or cured by treatment. Almost all viruses are capable of causing complications in vulnerable patients, such as viremia, pneumonia and sepsis, but certain viruses can cause severe infections that if left untreated in any individual can result in organ damage, organ failure, and even death. These symptoms arise due to the virus itself but can also be caused by an excessive immune response. Some viruses are latent and do not cause symptomatic illness immediately following infection. While latent viruses can lead to the inadvertent spread of the virus to other individuals, they can also become reactivated several years after the initial infection, causing severe symptoms that are often fatal and could have been avoided with earlier treatment.

West Nile Virus (WNV) in particular has received significant attention recently as the number of new infections reported in non-endemic areas is increasing. For example, in the past ten years approximately 40,000 individuals have been infected with WNV in the United States, of which ~20% developed neuroinvasive diseases (i.e. encephalitis and meningitis) with a 12% fatality rate.

Influenza viruses cause a common illness known as 'flu' and are particularly prevalent among the population in the winter months. Most individuals infected with influenza develop a mild respiratory illness, but disease burden increases with age and individuals with weakened immune systems are at risk of developing more severe illness. The mortality rate of influenza is reported as between 0.1 and 0.5% in the US, but the mortality rate varies depending on the particular influenza strain and country. The World Health Organisation estimated that seasonal influenza epidemics cause 3-5 million cases of severe illness and 291,000-646,000 deaths globally each year. Due to the ability of influenza viruses to undergo genetic shift, specific influenza strains can have significantly higher mortality rates and are capable of causing pandemics. Notably, four influenza pandemics have occurred since 1900 (H1N1 Spanish flu, H2N2 Asian flu, H3N2 Hong Kong flu, the H1N1 swine flu).

As such, there is a need to provide new treatments for viral infections such as West Nile virus and Influenza. The present invention address this need.

SUMMARY OF THE INVENTION

In one aspect, the present invention is directed to a compound of general formula I, or a pharmaceutically acceptable salt or stereoisomer thereof, (I)

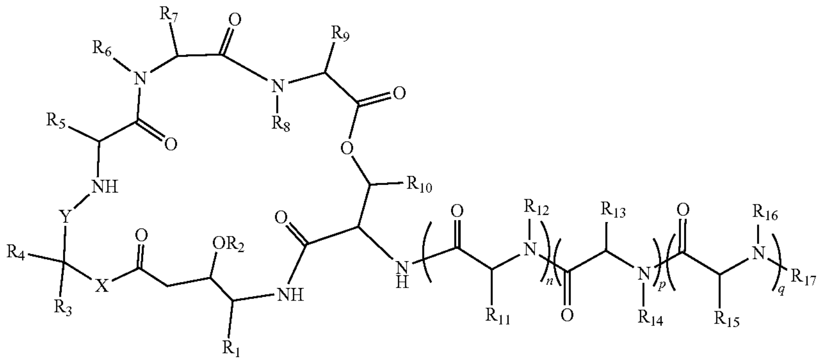

wherein X is selected from O and NH;

Y is selected from CO and —COCH(CH3)CO—;

each n and p is independently selected from 0 and 1, and q is selected from 0, 1 and 2; each R1, R3, R5, R9, R11, and R15 is independently selected from hydrogen, substituted or unsubstituted C1-C6 alkyl, substituted or unsubstituted C2-C6 alkenyl, and substituted or unsubstituted C2-C6 alkynyl;

R2 is selected from hydrogen, CORa, COORa, substituted or unsubstituted C1-C6 alkyl, substituted or unsubstituted C2-C6 alkenyl, and substituted or unsubstituted C2-C6 alkynyl;

each R4, R8, R10, R12, and R16 is independently selected from hydrogen and substituted or unsubstituted C1-C6 alkyl;

each R7 and R13 is independently selected from hydrogen, substituted or unsubstituted C1-C6 alkyl, substituted or unsubstituted C2-C6 alkenyl, and substituted or unsubstituted C2-C6 alkynyl;

each R6 and R14 is independently selected from hydrogen and substituted or unsubstituted C1-C6 alkyl; or R6 and R7 and/or R13 and R14 together with the corresponding N atom and C atom to which they are attached may form a substituted or unsubstituted heterocyclic group;

R17 is selected from hydrogen, CORa, COORa, CONHRb, COSRc, (C═NRb)ORa, (C═NRb)NHRb, (C═NRb)SRc, (C═S)ORa, (C═S)NHRb, (C═S)SRc, SO2Rc, SO3Rc, substituted or unsubstituted C1-C12 alkyl, substituted or unsubstituted C2-C12 alkenyl, substituted or unsubstituted C2-C12 alkynyl, substituted or unsubstituted aryl, and substituted or unsubstituted heterocyclic group, with the proviso that when n, p, and q are 0 then R17 is not hydrogen; and each Ra, Rb, and Rc is independently selected from hydrogen, substituted or unsubstituted C1-C12 alkyl, substituted or unsubstituted C2-C12 alkenyl, substituted or unsubstituted C2-C12 alkynyl, substituted or unsubstituted aryl, and substituted or unsubstituted heterocyclic group; for use in the treatment of a viral infection, wherein the virus is selected from the Orthomyxoviridae family or wherein the virus is West Nile virus. In one embodiment, the virus is selected from the Orthomyxoviridae family. In another embodiment, the virus is West Nile virus.

In a particular aspect, the compound of general formula I is PLD, or a pharmaceutically acceptable salt or stereoisomer thereof.

In a particular aspect, the compound of general formula I is DidemninB, or a pharmaceutically acceptable salt or stereoisomer thereof.

In another aspect, the present invention is also directed to a pharmaceutical composition comprising a compound as defined herein, and a pharmaceutically acceptable carrier, for use according to the present invention.

In another aspect, the present invention is directed to the use of a compound as defined herein, in the manufacture of a medicament for the treatment of a viral infection, wherein the virus is selected from the Orthomyxoviridae family or wherein the virus is West Nile virus.

In another aspect, the present invention is directed to a method for treating a viral infection in any mammal, preferably a human, wherein the method comprises administering to an individual in need thereof a therapeutically effective amount of a compound as defined herein, and wherein the virus is selected from the Orthomyxoviridae family or wherein the virus is West Nile virus.

In a further aspect of the invention, there is provided a kit comprising the compound as defined herein, together with instructions for treating a viral infection, wherein the virus is selected from the Orthomyxoviridae family or wherein the virus is West Nile virus.

The following embodiments apply to all aspects of the present invention.

In one embodiment, the Orthomyxoviridae virus is selected from Influenzavirus A, Influenzavirus B, Influenzavirus C, Thogotovirus, Quaranjavirus, and Isavirus. In another embodiment, the Orthomyxoviridae virus is Influenza A, preferably selected from H1N1, H1N2 and H3N2. In another embodiment, the Orthomyxoviridae virus is influenza B, preferably selected from the Yamagata or Victoria lineages.

In one embodiment, the West Nile virus is selected from lineage 1, 2, 3, 4, 5, 6, 7 or 8. Preferably the virus is lineage 1 or 2 (WNV-1 or WNV-2). In one embodiment the west nile virus is West Nile-NY99.

$R_3$ and $R_4$ may be independently selected from hydrogen and substituted or unsubstituted $C_1$-$C_6$ alkyl. $R_3$ may be isopropyl and $R_4$ may be hydrogen. $R_3$ and $R_4$ may be methyl (this compound is also designated a compound of general formula II).

$R_{11}$ may be selected from hydrogen and substituted or unsubstituted $C_1$-$C_6$ alkyl. $R_{11}$ may be methyl or isobutyl. $R_{11}$ may be methyl and n=1 (this compound is also designated a compound of general formula III).

$R_1$, $R_5$, $R_9$, and $R_{15}$ may be independently selected from hydrogen and substituted or unsubstituted $C_1$-$C_6$ alkyl. $R_1$ may be selected from sec-butyl and isopropyl, $R_5$ may be isobutyl, $R_9$ may be p-methoxybenzyl, and $R_{15}$ may be selected from methyl and benzyl.

$R_8$, $R_{10}$, $R_{12}$, and $R_{16}$ may be independently selected from hydrogen and substituted or unsubstituted $C_1$-$C_6$ alkyl. $R_8$, $R_{10}$ and $R_{12}$ may be methyl, and $R_{16}$ may be hydrogen.

$R_6$ and $R_{14}$ may be independently selected from hydrogen and substituted or unsubstituted $C_1$-$C_6$ alkyl. $R_6$ may be selected from hydrogen and methyl, and $R_{14}$ may be hydrogen.

$R_7$ and $R_{13}$ may be independently selected from hydrogen and substituted or unsubstituted $C_1$-$C_6$ alkyl. $R_7$ may be methyl and $R_{13}$ may be selected from hydrogen, methyl, isopropyl, isobutyl, and 3-amino-3-oxopropyl.

$R_6$ and $R_7$ and/or $R_{13}$ and $R_{14}$ together with the corresponding N atom and C atom to which they are attached may form a substituted or unsubstituted pyrrolidine group.

$R_2$ may be selected from hydrogen, substituted or unsubstituted $C_1$-$C_6$ alkyl, and CORa, and wherein $R_a$ may be a substituted or unsubstituted $C_1$-$C_6$ alkyl. $R_2$ may be hydrogen.

$R_{17}$ may be selected from hydrogen, CORa, $COOR_a$, $CONHR_b$, (C═S)$NHR_b$, and $SO_2R_c$, and wherein each $R_a$, $R_b$, and $R_c$ may be independently selected from substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted aryl, and substituted or unsubstituted heterocyclic group. $R_{17}$ may be selected from hydrogen, COObenzyl, CObenzo[b]thiophen-2-yl, $SO_2$(p-methylphenyl), $COCOCH_3$ and $COOC(CH_3)_3$.

X may be NH. X may be O. Y may be CO. Y may be —$COCH(CH_3)CO$—.

The compound may be PLD, or pharmaceutically acceptable salts or stereoisomers thereof. The compound may be PLD.

The compound may be didemninB, or pharmaceutically acceptable salts or stereoisomers thereof. The compound may be didemninB.

The viral infection may be a mild infection; and/or moderate infection; and/or severe infection.

The use may include use in the treatment of a patient with signs and symptoms of the viral infection for up to 4 weeks; and/or from 4 weeks to 12 weeks; and/or for more than 12 weeks.

The use may include use in the prophylaxis, reduction or treatment of persistent, viral symptoms.

The use may reduce the infectivity of infected patients; including wherein the patient is asymptomatic or not very symptomatic yet has a high viral load. The use may reduce the occurrence of supercontagators (asymptomatic or not very symptomatic patients with high viral loads (e.g. TC<25)). The present invention achieves a rapid and significant reduction in the viral burden. Reducing the viral burden may reduce the infectiveness of patients. This is particularly beneficial with patients who are asymptomatic or not very symptomatic yet have a high viral loads (e.g. TC<25). Such patients may be supercontagators or superspreaders. Administration of compounds according to the present invention upon detection of infection can reduce the viral burden and therefore reduce the infectiveness of the patient.

The treatment may result in a reduction of viral load. This may be expressed as a replication cycle threshold (Ct) value greater than 30 (Ct>30), on day 6 after the administration. The treatment may reduce viral load from baseline. This may be expressed as a reduction in the percentage of patients requiring hospitalisation following administration. This may be expressed as a reduction in the percentage of patients requiring invasive mechanical ventilation and/or admission to the ICU following administration. This may be expressed as a reduction of patients who develop sequelae related to persistent disease. This may be expressed as an increase in the percentage of patients with normalization of analytical parameters chosen as poor prognosis criteria (including, for example, lymphopenia, LDH, D-dimer or PCR). This may be expressed as an increase in the percentage of patients with normalization of clinical criteria (disappearance of symptoms), including, for example: headache, fever, cough, fatigue, dyspnea (shortness of breath), arthromyalgia or diarrhoea.

The compound may be administered in combination with a corticosteroid, preferably dexamethasone. The compound and corticosteroid may be administered concurrently, separately or sequentially.

The compound may be administered according to a regimen of a once daily dose for 10 days, 9 days, 8 days, 7 days, 6 days, 5 days, 4 days, 3 days, 2 days or 1 day; preferably 2-5 days, 3-5 days, or 3, 4 or 5 days; most preferably 3 days or 5 days; most preferably 3 days.

The compound may be administered at a dose of 5 mg a day or less, 4.5 mg a day or less, 4 mg a day or less, 3.5 mg a day or less, 3 mg a day or less, 2.5 mg a day or less or 2 mg a day or less; 0.5 mg/day, 1 mg/day, 1.5 mg/day, 2 mg/day, 2.5 mg/day, 3 mg/day, 3.5 mg/day, 4 mg/day, 4.5 mg/day, or 5 mg/day; preferably 1 mg/day, 1.5 mg/day, 2 mg/day or 2.5 mg/day; preferably 1.5-2.5 mg/day; further preferably 1.5 mg/day, 2 mg/day or 2.5 mg/day.

The compound may be administered at a total dose of 1-50 mg, 1-40 mg, 1-30 mg, 1-20 mg, 1-15 mg, 3-15 mg, 3-12 mg, 4-12 mg, 4-10 mg, or 4.5-10 mg; 4 mg, 4.5 mg, 5 mg, 5.5 mg, 6 mg, 6.5 mg, 7 mg, 7.5 mg, 8 mg, 8.5 mg, 9 mg, 9.5 mg or 10 mg; preferably 4.5 mg, 5 mg, 6 mg, 7.5 mg, 8 mg, 9 mg or 10 mg; more preferably 4.5-7.5 mg/day. The total dose may be split over 1, 2, 3, 4, 5, 6, 7, 8, 9 or 10 days, preferably 3 days or 5 days; most preferably 3 days.

The compound may be administered at a once daily dose for 3 days at a dose of 1.5-2.5 mg/day. The dose may be 1.5 mg/day. The dose may be 2.5 mg/day.

The compound may be PLD administered as a 1.5-hour infusion, once a day for 3 consecutive days. 1.5 mg of PLD may be administered as a 1.5-hour infusion, once a day for 3 consecutive days. 2 mg of PLD may be administered as a 1.5-hour infusion, once a day for 3 consecutive days. 2.5 mg of PLD may be administered as a 1.5-hour infusion, once a day for 3 consecutive days. 1 mg of PLD may be administered as a 1.5-hour infusion, once a day for 5 consecutive days. 2 mg of PLD may be administered as a 1.5-hour infusion, once a day for 5 consecutive days.

The regimen may be a single dose (1 day). The compound may be administered as a single dose of 1-10 mg, 4-10 mg, 4.5-10 mg; 4 mg, 4.5 mg, 5 mg, 5.5 mg, 6 mg, 6.5 mg, 7 mg, 7.5 mg, 8 mg, 8.5 mg, 9 mg, 9.5 mg or 10 mg; preferably 4.5 mg, 5 mg, 6 mg, 7.5 mg, 8 mg, 9 mg or 10 mg; more preferably 5-9 mg, 6.5-8.5 mg, 7-8 mg or 7.5 mg. The compound may be PLD administered as a single dose 1.5-hour infusion.

The single dose regimen may be utilised with all therapies set out in the present invention. The combination use with corticosteroids (including subsequent corticosteroid administration) may in embodiments be used with the single dose regimen. The multi-day regimen may be utilised with all therapies set out in the present invention.

The corticosteroid may be administered daily on the same day(s) as administering a compound according to the present invention. The corticosteroid may be administered on one or more subsequent days. The corticosteroid may be administered on 1, 2, 3, 4, 5, 6, 7, 8, 9, 10 or more subsequent days. The corticosteroid may be administered at a higher dose when administered on the same day(s) as a compound according to the present invention and at a lower dose on subsequent days. The corticosteroid may be dexamethasone.

The compound according to the present invention may be administered at a dose according to the present invention on days 1-3 of the dosage regimen. The corticosteroid may be administered intravenously on days 1-3 of the dosage regimen. The corticosteroid may thereafter be administered by oral administration or IV from Day 4 and up to Day 10 (as per physician judgement according to patient clinical condition and evolution). The corticosteroid may be dexamethasone. The dose may be 6.6 mg/day IV on Days 1 to 3 (for example 8 mg dexamethasone phosphate), followed by dexamethasone 6 mg/day (for example 7.2 mg dexamethasone phosphate or 6 mg dexamethasone base) oral administration or IV from Day 4 and up to Day 10.

In embodiments, dexamethasone is dexamethasone phosphate and is administered at a dose of 8 mg/day IV on Days 1 to 3, followed by dexamethasone 7.2 mg/day oral administration or IV from Day 4 and up to Day 10.

The compound according to the present invention may be administered as an infusion, preferably a 1 hour infusion, a 1.5 hour infusion, a 2 hour infusion, a 3 hour infusion or longer; particularly preferably a 1.5 hour infusion.

The regimen may be 1.5 mg of plitidepsin administered as a 1.5-hour infusion, once a day for 3 consecutive days; or 2 mg of plitidepsin administered as a 1.5-hour infusion, once a day for 3 consecutive days; or 2.5 mg of plitidepsin administered as a 1.5-hour infusion, once a day for 3 consecutive days; or 1 mg of plitidepsin administered as a 1.5-hour infusion, once a day for 5 consecutive days; or 2 mg of plitidepsin administered as a 1.5-hour infusion, once a day for 5 consecutive days.

The regimen may be 7.5 mg of plitidepsin administered as a 1.5-hour infusion, as a single dose on day 1.

The compound according to the present invention may be administered using a loading dose and a maintenance dose.

The regimen according to the present invention may be:

- a loading dose of 2.5 mg for day 1, and followed by a maintenance dose of 2 mg/day for subsequent days;
- a loading dose of 2.5 mg for day 1, and followed by a maintenance dose of 1.5 mg/day for subsequent days;
- a loading dose of 2.5 mg for day 1, and followed by a maintenance dose of 1 mg/day for subsequent days;
- a loading dose of 2.5 mg for day 1, and followed by a maintenance dose of 0.5 mg/day for subsequent days;
- a loading dose of 2 mg for day 1, and followed by a maintenance dose of 1.5 mg/day for subsequent days;
- a loading dose of 2 mg for day 1, and followed by a maintenance dose of 1 mg/day for subsequent days;
- a loading dose of 2 mg for day 1, and followed by a maintenance dose of 0.5 mg/day for subsequent days;
- a loading dose of 1.5 mg for day 1, and followed by a maintenance dose of 1 mg/day for subsequent days;
- a loading dose of 1.5 mg for day 1, and followed by a maintenance dose of 0.5 mg/day for subsequent days; or
- a loading dose of 1 mg for day 1, and followed by a maintenance dose of 0.5 mg/day for subsequent days.

The compound according to the present invention may be administered in combination with a corticosteroid. The corticosteroid may be administered on the same day(s) as administration of the compound.

The corticosteroid may also be administered on one or more subsequent days. For example, the corticosteroid is administered with the compound on days 1-3 and the corticosteroid is further administered on one or more of days 4-10.

The corticosteroid may be administered intravenously on days when the compound is administered but administered by oral administration or IV on subsequent days.

The corticosteroid may be dexamethasone. Dexamethasone may be administered at a dose of 6.6 mg/day IV on days when the compound is administered.

Dexamethasone may be administered at a dose of 6 mg/day oral administration or IV on subsequent days, preferably one or more of days 4, 5, 6, 7, 8, 9 and 10.

The dexamethasone dose as defined herein refers to the base weight. The dose can therefore be adjusted if used in salt form. For example, the dexamethasone may be dexamethasone phosphate such that 8 mg/day is equivalent to 6.6 mg of dexamethasone base, and 7.2 mg/day is equivalent to 6 mg of dexamethasone base.

The compound according to the present invention, particularly PLD, may be administered 1.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

The compound according to the present invention, particularly PLD, may be administered 2.0 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

The compound according to the present invention, particularly PLD, may be administered 2.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

The corticosteroid may be administered 20 to 30 minutes prior to starting treatment with the compound as defined herein.

In regimens according to the present invention, the patient may additionally receive the following medications, preferably 20 to 30 minutes prior to starting treatment with the compound according to the present invention:

Ondansetron 8 mg IV (or equivalent);

Diphenhydramine hydrochloride 25 mg IV (or equivalent); and

Ranitidine 50 mg IV (or equivalent).

In regimens according to the present invention, on Days 4 and 5, patients may receive ondansetron (or equivalent) 4 mg twice a day PO.

When administered as a single dose, patients may receive the following prophylactic medications 20-30 minutes prior to plitidepsin infusion:

Diphenhydramine hydrochloride 25 mg i.v;

Ranitidine 50 mg i.v;

Dexamethasone 6.6 mg intravenously;

Ondansetron 8 mg i.v. in slow infusion of 15 minutes.

Ondansetron 4 mg orally may be given every 12 hours for 3 days after plitidepsin administration to relieve drug-induced nausea and vomiting. If plitidepsin is administered in the morning the patient may receive the first dose of ondansetron in the afternoon.

DESCRIPTION OF THE FIGURES

The invention is further described in the following non-limiting figures.

DETAILED DESCRIPTION OF THE INVENTION

Figure 1A:
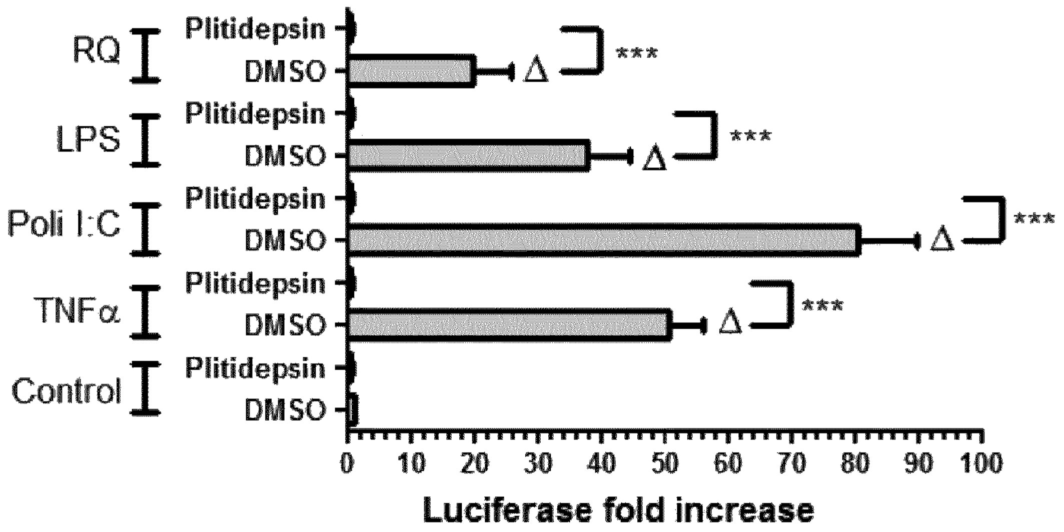
FIG. 1 shows that NF-κB transactivation in response to the activation of Toll-like receptors is inhibited by PLD. Human monocytic cells (THP-1) were stably transfected with a NF-kB-Luc plasmid and (A) levels of NF-kB transactivation measured in the presence and absence of PLD. (B) Compound-induced cytotoxicity was tested by the MTT cell proliferation assay. Cultures were exposed to PLD at 100 nM for 6 hours. RQ—Resiquimod at 10 μg/mL. LPS-B5—Lipopolysaccharide from *Escherichia coli* 055:B5 (LPS-B5) at 10 μg/mL. Poly-C—Polyinosinic-polycytidylic at 500 μg/mL. TNF-α was used as a positive control. $*p<0.001$; $p<0.01$

The following embodiments apply to all aspects of the present invention.

The present invention will now be further described. In the following passages, different aspects of the invention are defined in more detail. Each aspect so defined may be combined with any other aspect or aspects or embodiment or embodiments unless clearly indicated to the contrary. In particular, any feature indicated as being preferred or advantageous may be combined with any other feature or features indicated as being preferred or advantageous.

In the present application, a number of general terms and phrases are used, which should be interpreted as follows.

The term "treating", as used herein, unless otherwise indicated, means reversing, attenuating, alleviating or inhibiting the progress of the disease or condition to which such term applies, or one or more symptoms of such disorder or condition. The term treating as used herein may also include prophylactic treatment.

"Treat", "treating", and "treatment" in the context of a viral infection may refer to one or more of the following: 1) reduction in the number of infected cells; 2) reduction in the number of virions present in the serum, including reduction in viral titre (which can be measured by qPCR); 3) inhibition (i.e., slowing to some extent, preferably stopping) the rate of viral replication; 4) reduction in the viral RNA load; 5) reduction in the viral infectivity titre (the number of virus particles capable of invading a host cell); and 6) relieving or reducing to some extent one or more of the symptoms associated with the viral infection. This may include inflammation associated with viral infection.

"Patient" includes humans, non-human mammals (e.g., dogs, cats, rabbits, cattle, horses, sheep, goats, swine, deer, and the like) and non-mammals (e.g., birds, and the like). The patient my require hospitalisation for management of the infection.

Plitidepsin (PLD) is a cyclic depsipeptide originally isolated from the marine tunicate *Aplidium albicans*. PLD is also known as Aplidin or Aplidine. Such terms are used interchangeably herein.

PLD analogues are those analogues as defined herein as compounds of Formula I, II or III. In a preferred embodiment, the present invention relates to the use of PLD.

West Nile virus (WNV) is an important emerging neurotropic virus, responsible for increasingly severe encephalitis outbreaks in humans and horses worldwide. WNV is encoded by a ~11 kb positive-sense single-stranded RNA (ssRNA) genome. The genome is translated as a single polyprotein, and subsequent cleavage of this polyprotein by viral and host proteases generates 10 viral proteins. WNV pathogenesis follow three phases, the early phase initial infection and spread (the early phase), peripheral viral amplification (the visceral-organ dissemination phase) and neuroinvasion (the central nervous system (CNS) phase).

The early phase after subcutaneous infection is defined by WNV replication in keratinocytes and skin-resident DCs, followed by viral amplification within the draining lymph node, which results in viremia and spread to visceral organs. The specific target cells for WNV infection are not well defined, but are thought to be subsets of DCs, macrophages and possibly neutrophils. WNV invasion of the CNS tissues (for example, the brain and spinal cord) constitutes the third phase of the infection. WNV may enter the brain though a combination of mechanisms that facilitates viral neuroinvasion, such as direct infection with or without a breakdown of the blood-brain barrier (BBB) and/or virus transport along peripheral neurons.

A major hallmark of WNV pathogenesis is neuroinflammation, which is caused by exaggerated innate and acquired immune response. Accumulation of inflammatory monocytes into the brain and their differentiation to macrophages and microglia can also worsen neuroinflammation and CNS injury, as demonstrated in a murine model of nonlethal WNV infection. Recognition of WNV nucleic acid in monocytes/microglia by TLRs may lead to the production of TNF-α, which results in a loss of tight junctions, allowing the entry of WNV and immune cells into the perivascular space of the brain in mice. Thus, activation of cells of the monocyte/macrophage system by WNV appears to result in important neuropathological consequences, and exaggerated innate responses may cause inflammation, altering the blood brain barrier permeability and allowing the virus to enter the CNS. Indeed, treatment of infected neuronal cells with antibodies blocking TNF-α and other pro-inflammatory mediators results in a significant reduction of WNV-mediated neuronal death, suggesting that such mediators play a major role in the pathogenesis of WNV infection in the CNS.

The family Orthomyxoviridae is a family of negative-sense RNA viruses and contains significant pathogens of both humans and animals. There are seven genera in the family, including Influenzavirus A, Influenzavirus B, Influenzavirus C, Thogotovirus, Quaranjavirus, and Isavirus There are four classes of influenza viruses: A, B, C and D, with influenza virus A and B in particular causing winter epidemics of flu, causing around 300 to 650 thousand deaths a year.

Influenza A viruses are of particular clinical significance as they have been the cause of a number of flu pandemics where many countries have been affected by large outbreaks. Influenza A viruses are negative-sense, single-stranded, segmented RNA viruses that are divided into subtypes based on two proteins on the surface of the virus: hemagglutinin (H) and neuraminidase (N). There are 18 different hemagglutinin subtypes and 11 different neuraminidase subtypes (H1 through H18 and N1 through N11, respectively), therefore there are many subtypes of influenza virus that may be circulating in the population at any given time, causing the disease known as flu. However, in one embodiment, the invention relates to the human influenza viruses, and in particular the H1N1, H1N2 and H3N2 sub-types of Influenza A and the Victoria and Yamagata lineages of Influenza B.

Flu is characterized by a mild to severe disease which symptoms include high fever, runny nose, sore throat, muscle and joint pain, headache, coughing and tiredness, although vomiting and diarrhea can also occur in children infected with the virus. These symptoms typically appear one to four days after exposure and are generally self-limiting, however in some cases, particularly in those with weaker immune systems, complications such as pneumonia and sepsis can occur.

Severe influenza infection has been associated with significant pathological changes in pulmonary tissues associated with heightened levels of inflammatory cytokines and chemokines. This exuberant immune response, known as the cytokine storm, is associated with high levels of pro-inflammatory cytokines and widespread tissue damage. In fact, the term "cytokine storm" was first coined when describing the immune response to influenza-associated encephalopathy. It is thought that influenza infection of epithelial cells in the respiratory tract leads to a wave of inflammatory cytokine production from these cells, driving various interferon-regulated genes that go on to cause further downstream cytokine production through activation of innate immune cells such as macrophages, neutrophils and dendritic cells which, in severe cases, can proceed to cause tissue damage and chronic inflammation. It is this positive feedback loop of inflammation that can result in complications relating to influenza infection, and can ultimately result in death for patients most severely affected.

In compounds of the present invention; the groups can be selected in accordance with the following guidance:

Alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, n-propyl, isopropyl and butyl, including n-butyl, tert-butyl, sec-butyl and isobutyl are particularly preferred alkyl groups in the compounds of the present invention. As used herein, the term alkyl, unless otherwise stated, refers to both cyclic and noncyclic groups, although cyclic groups will comprise at least three carbon ring members.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 6 carbon atoms. Even more preferred are alkenyl and alkynyl groups having 2, 3 or 4 carbon atoms. The terms alkenyl and alkynyl as used herein, unless otherwise stated, refer to both cyclic and noncyclic groups, although cyclic groups will comprise at least three carbon ring members.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl, and substituted or unsubstituted anthryl.

Suitable heterocyclic groups include heteroaromatic and heteroalicyclic groups containing from 1 to 3 separated or fused rings and from 5 to about 18 ring atoms. Preferably heteroaromatic and heteroalicyclic groups contain from 5 to about 10 ring atoms, most preferably 5, 6 or 7 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl including pyrazol-3-yl, pyrazol-4-yl and pyrazol-5-yl, pyrimidinyl, furanyl including furan-2-yl, furan-3-yl, furan-4-yl and furan-5-yl, pyrrolyl, thienyl, thiazolyl including thiazol-2-yl, thiazol-4-yl and thiazol-5-yl, isothiazolyl, thiadiazolyl including thiadiazol-4-yl and thiadiazol-5-yl, triazolyl, tetrazolyl, isoxazolyl including isoxazol-3-yl, isoxazol-4-yl and isoxazol-5-yl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl including benzo[b]thiophen-2-yl and benzo[b]thiophen-3-yl, benzothiazolyl, benzoxazolyl, imidazo[1,2-a]pyridinyl including imidazo[1,2-a]pyridine-2-yl and imidazo[1,2-a]pyridine-3-yl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuranyl, dihydrofuranyl, tetrahydrothienyl, tetrahydrothiopyranyl, piperidinyl including piperidin-3-yl, piperidin-4-yl and piperidin-5-yl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, dihydropyrrolyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

In the above mentioned groups one or more hydrogen atoms may be substituted by one or more suitable groups such as OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. When a substituent group terminates with a double bound (such as =O and =N—R') it replaces 2 hydrogen atoms in the same carbon atom.

Suitable halogen substituents in the compounds of the present invention include F, Cl, Br and I.

The term "pharmaceutically acceptable salts" refers to any salt which, upon administration to the patient is capable of providing (directly or indirectly) a compound as described herein. It will be appreciated that non-pharmaceutically acceptable salts also fall within the scope of the invention since those may be useful in the preparation of pharmaceutically acceptable salts. The preparation of salts can be carried out by methods known in the art. For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic amino acids salts.

The compounds of the invention may be in crystalline form either as free compounds or as solvates (e.g. hydrates, alcoholates, particularly methanolates) and it is intended that both forms are within the scope of the present invention. Methods of solvation are generally known within the art. The compounds of the invention may present different polymorphic forms, and it is intended that the invention encompasses all such forms Any compound referred to herein is intended to represent such specific compound as well as certain variations or forms. In particular, compounds referred to herein may have asymmetric centres and therefore exist in different enantiomeric or diastereomeric forms. Thus any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same or different than the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

In compounds of general formula I and II, particularly preferred $R_1$, $R_5$, $R_9$, Rn, and $R_{15}$ are independently selected from hydrogen and substituted or unsubstituted $C_1$-$C_6$ alkyl. More preferred $R_1$, $R_5$, $R_9$, $R_{11}$, and $R_{15}$ are independently selected from hydrogen, substituted or unsubstituted methyl, substituted or unsubstituted ethyl, substituted or unsubstituted n-propyl, substituted or unsubstituted isopropyl and substituted or unsubstituted butyl, including substituted or unsubstituted n-butyl, substituted or unsubstituted tert-butyl, substituted or unsubstituted isobutyl, and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Hydrogen, methyl, n-propyl, isopropyl, isobutyl, sec-butyl, 4-aminobutyl, 3-amino-3-oxopropyl, benzyl, p-methoxybenzyl, p-hydroxybenzyl, and cyclohexylmethyl are the most preferred $R_1$, $R_5$, $R_9$, Rn, and $R_{15}$ groups. Specifically, particularly preferred $R_1$ is selected from sec-butyl and isopropyl, being sec-butyl the most preferred. Particularly preferred $R_5$ is selected from isobutyl and 4-aminobutyl, being isobutyl the most preferred. Particularly preferred Rn is methyl and isobutyl. Particularly preferred $R_9$ is selected from p-methoxybenzyl, p-hydroxybenzyl, and cyclohexylmethyl, being p-methoxybenzyl the most preferred. Particularly preferred $R_{15}$ is selected from methyl, n-propyl, and benzyl, being methyl and benzyl the most preferred.

In compounds of general formula III, particularly preferred $R_1$, $R_5$, $R_9$, and $R_{15}$ are independently selected from hydrogen and substituted or unsubstituted $C_1$-$C_6$ alkyl. More preferred $R_1$, $R_5$, $R_9$, and $R_{15}$ are independently selected from hydrogen, substituted or unsubstituted methyl, substituted or unsubstituted ethyl, substituted or unsubstituted n-propyl, substituted or unsubstituted isopropyl and substituted or unsubstituted butyl, including substituted or unsubstituted n-butyl, substituted or unsubstituted tert-butyl, substituted or unsubstituted isobutyl, and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Hydrogen, methyl, n-propyl, isopropyl, isobutyl, sec-butyl, 4-aminobutyl, 3-amino-3-oxopropyl, benzyl, p-methoxybenzyl, p-hydroxybenzyl, and cyclohexylmethyl are the most preferred $R_1$, $R_5$, $R_9$, and $R_{15}$ groups. Specifically, particularly preferred $R_1$ is selected from sec-butyl and isopropyl, being sec-butyl the most preferred. Particularly preferred $R_5$ is selected from isobutyl and 4-aminobutyl, being isobutyl the most preferred. Particularly preferred $R_9$ is selected from p-methoxybenzyl, p-hydroxybenzyl, and cyclohexylmethyl, being p-methoxybenzyl the most preferred. Particularly preferred $R_{15}$ is selected from methyl, n-propyl, and benzyl, being methyl and benzyl the most preferred.

In compounds of general formula I, II and III, particularly preferred $R_8$, $R_{10}$, $R_{12}$, and $R_{16}$ are independently selected from hydrogen and substituted or unsubstituted $C_1$-$C_6$ alkyl. More preferred $R_8$, $R_{10}$, $R_{12}$, and $R_{16}$ are independently selected from hydrogen, methyl, ethyl, n-propyl, isopropyl and butyl, including n-butyl, tert-butyl, isobutyl and sec-butyl, and even more preferred they are independently selected from hydrogen and methyl. Specifically, particularly preferred $R_8$, $R_{10}$ and $R_{12}$ are methyl, and particularly preferred $R_{16}$ is hydrogen.

In compounds of general formula I and III, particularly preferred $R_3$ and $R_4$ are independently selected from hydrogen and substituted or unsubstituted $C_1$-$C_6$ alkyl. More preferred $R_3$ and $R_4$ are independently selected from hydrogen, substituted or unsubstituted methyl, substituted or unsubstituted ethyl, substituted or unsubstituted n-propyl, substituted or unsubstituted isopropyl, and substituted or unsubstituted butyl, including substituted or unsubstituted n-butyl, substituted or unsubstituted tert-butyl, substituted or unsubstituted isobutyl and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Hydrogen, methyl, isopropyl, and sec-butyl are the most preferred $R_3$ and $R_4$ groups. Specifically, particularly preferred $R_3$ is selected from methyl and isopropyl and particularly preferred $R_4$ is methyl or hydrogen.

In one embodiment of compounds of general formula I, II and III, particularly preferred $R_6$ and $R_7$ are independently selected from hydrogen and substituted or unsubstituted $C_1$-$C_6$ alkyl. More preferred $R_7$ is selected from hydrogen, substituted or unsubstituted methyl, substituted or unsubstituted ethyl, substituted or unsubstituted n-propyl, substituted or unsubstituted isopropyl and substituted or unsubstituted butyl, including substituted or unsubstituted n-butyl, substituted or unsubstituted tert-butyl, substituted or unsubstituted isobutyl, and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred $R_6$ is selected from hydrogen, methyl, ethyl, n-propyl, isopropyl and butyl, including n-butyl, tert-butyl, isobutyl and sec-butyl. Most preferred $R_6$ is selected from hydrogen and methyl and most preferred $R_7$ is methyl.

In another embodiment of compounds of general formula I, II and III, it is particularly preferred that $R_6$ and $R_7$ together with the corresponding N atom and C atom to which they are attached form a substituted or unsubstituted heterocyclic group. In this regard, preferred heterocyclic group is a heteroalicyclic group containing one, two or three heteroatoms selected from N, O or S atoms, most preferably one N atom, and having from 5 to about 10 ring atoms, most preferably 5, 6 or 7 ring atoms. A pyrrolidine group is the most preferred.

In one embodiment of compounds of general formula I, II and III, particularly preferred $R_{13}$ and $R_{14}$ are independently selected from hydrogen and substituted or unsubstituted $C_1$-$C_6$ alkyl. More preferred $R_{13}$ is selected from hydrogen, substituted or unsubstituted methyl, substituted or unsubstituted ethyl, substituted or unsubstituted n-propyl, substituted or unsubstituted isopropyl and substituted or unsubstituted butyl, including substituted or unsubstituted n-butyl, substituted or unsubstituted tert-butyl, substituted or unsubstituted isobutyl, and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred $R_{14}$ is selected from hydrogen, methyl, ethyl, n-propyl, isopropyl and butyl, including n-butyl, tert-butyl, isobutyl and sec-butyl. Most preferred $R_{13}$ is selected from hydrogen, methyl, isopropyl, isobutyl, and 3-amino-3-oxopropyl and most preferred $R_{14}$ is hydrogen.

In another embodiment of compounds of general formula I, II and III, it is particularly preferred that $R_{13}$ and $R_{14}$ together with the corresponding N atom and C atom to which they are attached form a substituted or unsubstituted heterocyclic group. In this regard, preferred heterocyclic group is a heteroalicyclic group containing one, two or three heteroatoms selected from N, O or S atoms, most preferably one N atom, and having from 5 to about 10 ring atoms, most preferably 5, 6 or 7 ring atoms. A pyrrolidine group is the most preferred.

In compounds of general formula I, II and III, particularly preferred $R_2$ is selected from hydrogen, substituted or unsubstituted $C_1$-$C_6$ alkyl, and CORa, wherein $R_a$ is a substituted or unsubstituted $C_1$-$C_6$ alkyl, and even more preferred $R_a$ is methyl, ethyl, n-propyl, isopropyl and butyl, including n-butyl, tert-butyl, sec-butyl and isobutyl. More preferably $R_2$ is hydrogen.

In compounds of general formula I, II and III, particularly preferred $R_{17}$ is selected from hydrogen, CORa, $COOR_a$, CONHRb, (C═S)NHRb, and $SO_2R_c$, wherein each $R_a$, $R_b$, and $R_c$ is preferably and independently selected from substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted aryl, and substituted or unsubstituted heterocyclic group. Preferred substituents of said groups are OR', ═O, SR', SOR', $SO_2R'$, $NO_2$, NHR', NR'R', ═N—R', NHCOR', $N(COR')_2$, $NHSO_2R'$, NR'C(═NR')NR'R', CN, halogen, COR', COOR', OCOR', OCONHR', OCONR'R', CONHR', CONR'R', substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Hydrogen, CORa, COORa, and $SO_2R_c$ are the most preferred $R_{17}$ groups, and hydrogen, COObenzyl, CObenzo[b]thiophen-2-yl, $SO_2$(p-methylphenyl), $COCOCH_3$ and $COOC(CH_3)_3$ are even most preferred.

In another embodiment of compounds of general formula I, II and III, it is particularly preferred that Y is CO. In another embodiment, it is particularly preferred that Y is —$COCH(CH_3)CO$—.

In another embodiment of compounds of general formula I, II and III, it is particularly preferred that X is O. In another embodiment, it is particularly preferred that X is NH.

In another embodiment of compounds of general formula I and II, it is particularly preferred that n, p and q are 0. In another embodiment, it is particularly preferred that n is 1 and p and q are 0. In another embodiment, it is particularly preferred that n and p are 1 and q is 0. In another embodiment, it is particularly preferred that n, p, and q are 1. In another embodiment, it is particularly preferred that n and p are 1 and q is 2.

In another embodiment of compounds of general formula III, it is particularly preferred that p and q are 0. In another embodiment, it is particularly preferred that p is 1 and q is 0. In another embodiment, it is particularly preferred that p and q are 1. In another embodiment, it is particularly preferred that p is 1 and q is 2.

In additional preferred embodiments, the preferences described above for the different substituents are combined. The present invention is also directed to such combinations of preferred substitutions of formula I, II and III above.

In the present description and definitions, when there are several groups $R_a$, $R_b$, and $R_c$ present in the compounds of the invention, and unless it is stated explicitly so, it should be understood that they can be each independently different within the given definition, i.e. $R_a$ does not represent necessarily the same group simultaneously in a given compound of the invention.

In compounds of general formula I, II and III when q takes a value of 2 there are two groups $R_{15}$ and two groups $R_{16}$ in the compound. It is hereby clarified that each $R_{15}$ and each $R_{16}$ group in a given compound may be independently selected among the different possibilities described above for such groups.

A particularly preferred stereochemistry for compounds of general formula I is

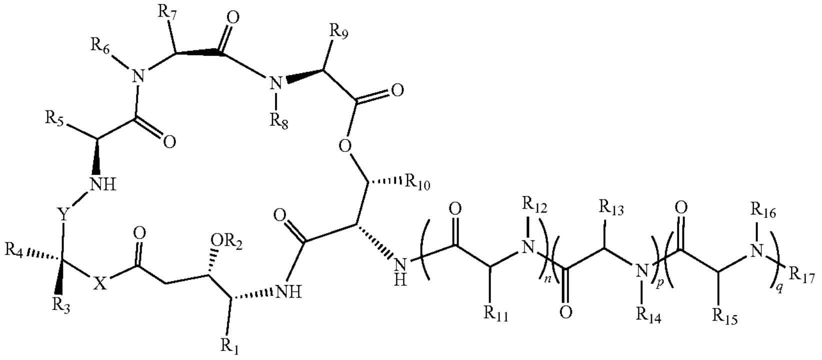

wherein X, Y, n, p, q, and $R_1$-$R_{17}$ are as defined above, and when Y is —$COCH(CH_3)CO$— it has the following stereochemistry:

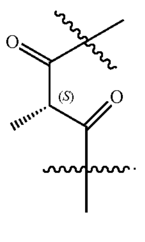

A particularly preferred stereochemistry for compounds of general formula II is

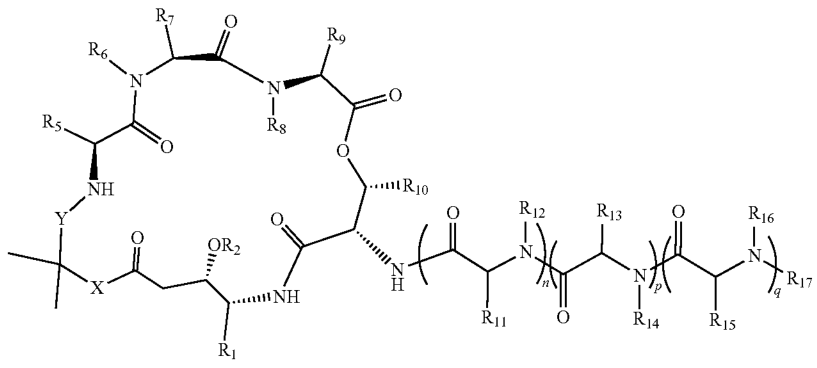

wherein X, Y, n, p, q, $R_1$, $R_2$, and $R_5$-$R_{17}$ are as defined above, and when Y is —COCH($CH_3$)CO— it has the following stereochemistry:

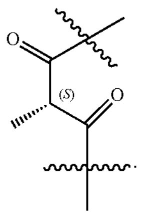

A particularly preferred stereochemistry for compounds of general formula III is

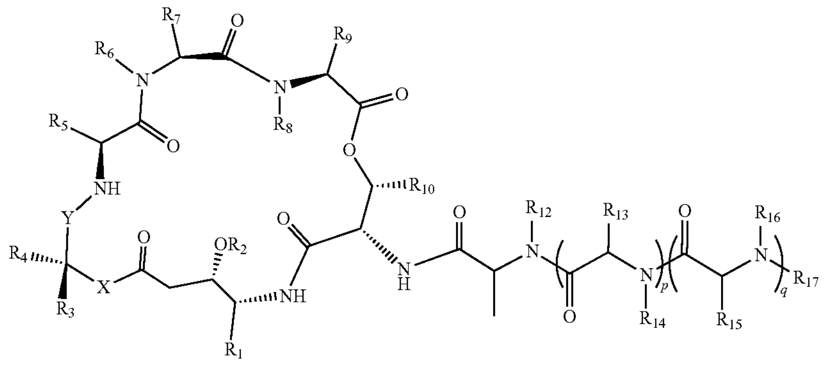

wherein X, Y, p, q, $R_1$-$R_{10}$, and $R_{12}$-$R_{17}$ are as defined above, and when Y is —COCH($CH_3$)CO— it has the following stereochemistry:

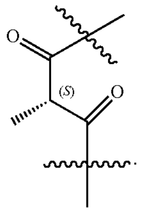

Particularly preferred compounds of the invention are the following:
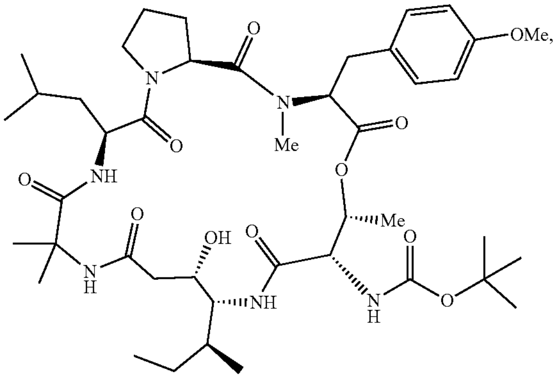
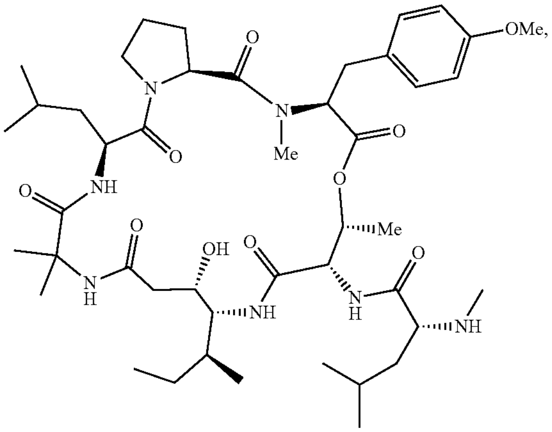
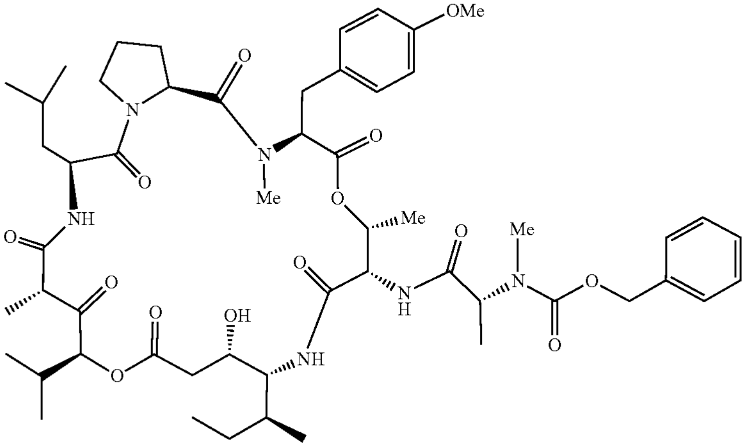
, -continued
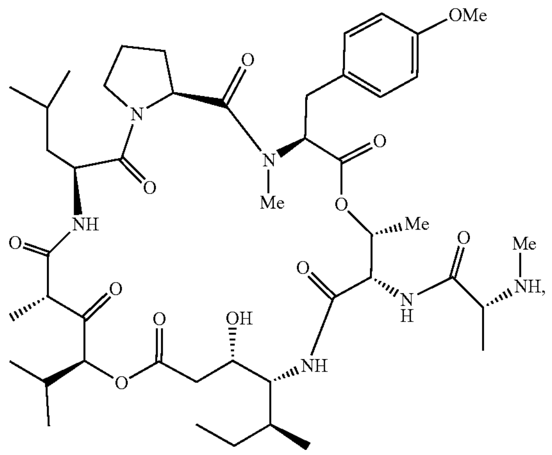
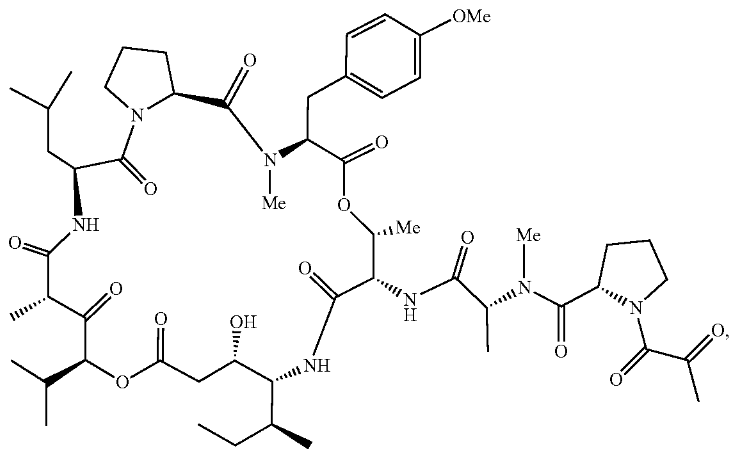
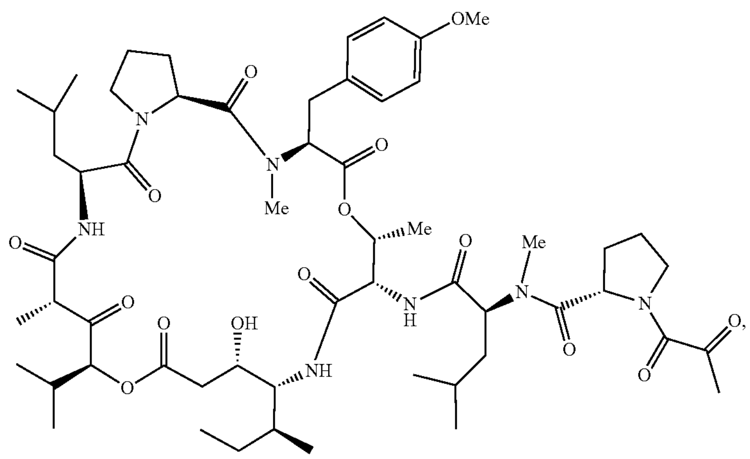

-continued

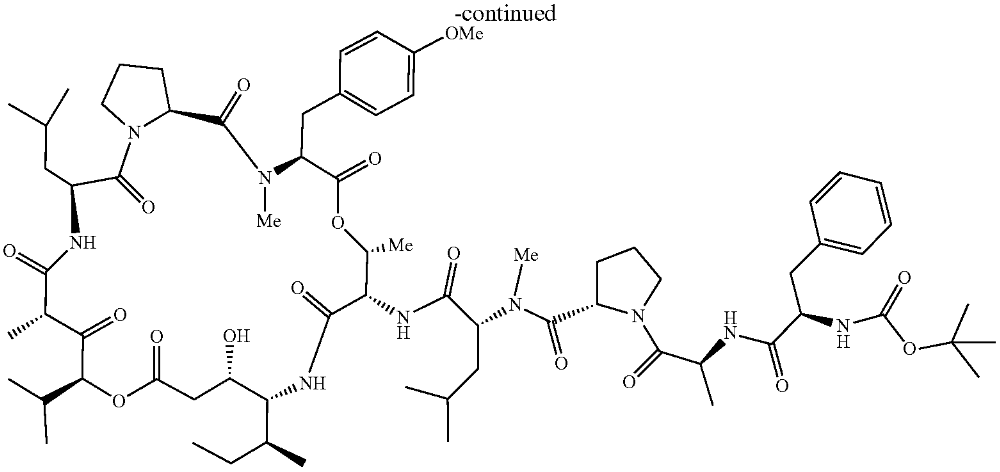

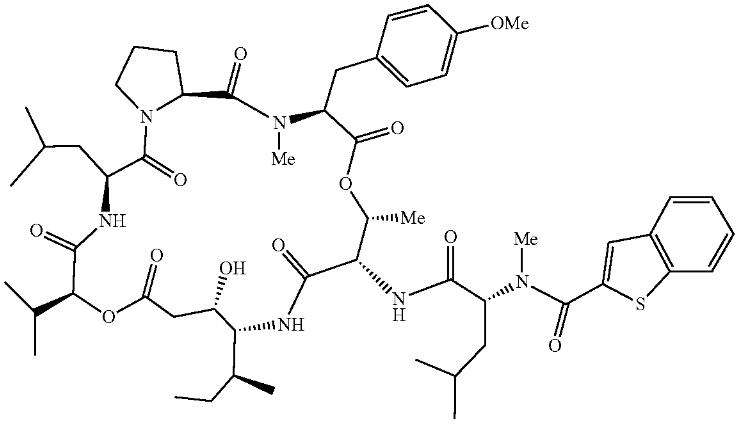

, and

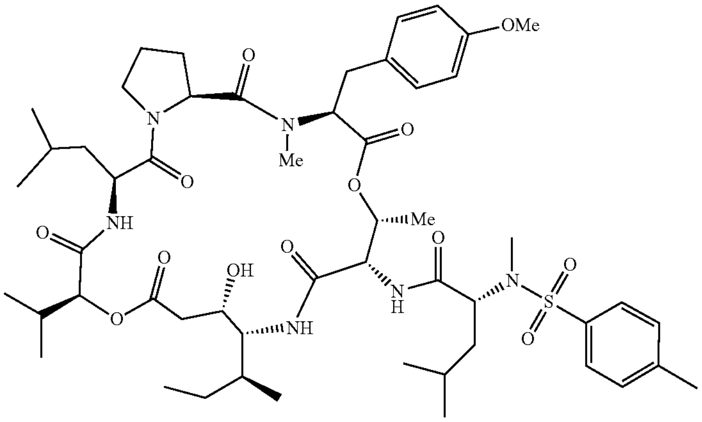

, or pharmaceutically acceptable salts or stereoisomers thereof.

The compounds of general formula I, II and III may be prepared following any of the synthetic processes disclosed in Vera et al. Med. Res. Rev. 2002, 22(2), 102-145, WO 2011/020913 (see in particular Examples 1-5), WO 02/02596, WO 01/76616, and WO 2004/084812, which are incorporated herein by reference.

The preferred compound is PLD or pharmaceutically acceptable salts or stereoisomers thereof. Most preferred is PLD.

The chemical name of plitidepsin is (−)-(3S,6R,7S,10R,11S,15S,17S,20S,25aS)-11-hydroxy-3-(4-methoxybenzyl)-2,6,17-trimethyl-15-(1-methylethyl)-7-[[(2R)-4-methyl-2-[methyl[[(2S)-1-(2-oxopropanoyl)pyrrolidin-2-yl]carbonyl]amino]pentanoyl]amino]-10-[(1S)-1-methylpropyl]-20-(2-methylpropyl)tetradecahydro-15H-pyrrolo[2,1-f]-[1,15,4,7,10,20]dioxatetrazacyclotricosine-1,4,8,13,16,18,21(17H)-heptone corresponding to the molecular formula $C_{57}H_{87}N_7O_{15}$. It has a relative molecular mass of 1110.34 g/mol and the following structure:

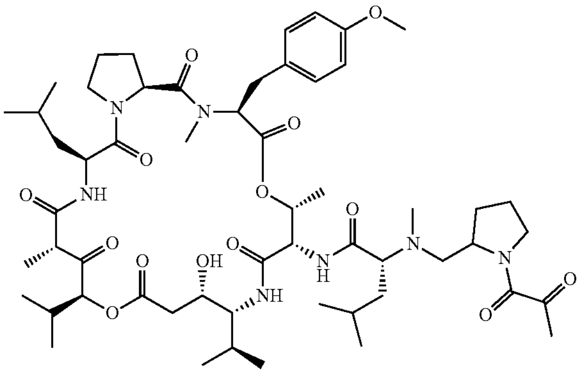

Plitidepsin is a cyclic depsipeptide originally isolated from a Mediterranean marine tunicate (*Aplidium albicans*) and currently manufactured by full chemical synthesis. It is licensed and marketed in Australia under the brand name plitidepsin for the treatment of multiple myeloma.

The present invention provides the use of a compound of the present invention in the treatment of a viral infection, wherein the virus is selected from the Orthomyxoviridae family or wherein the virus is West Nile virus.

In one aspect of the invention, there is provided a compound of the present invention, for use in the treatment of viral infection, wherein the virus is selected from the Orthomyxoviridae family or wherein the virus is West Nile virus.

In another aspect of the invention, there is provided the use of a compound of the present invention, in the manufacture of a medicament for the treatment of viral infection, wherein the virus is selected from the Orthomyxoviridae family or wherein the virus is West Nile virus.

In another aspect of the invention, there is provided a method for the treatment of a viral infection, wherein the virus is selected from the Orthomyxoviridae family or wherein the virus is West Nile virus, wherein the method comprises administering to an individual in need thereof a therapeutically effective amount of a compound of the present invention.

The infection may also be characterised by excessive or increased production or secretion of one or more pro-inflammatory cytokines, and preferably at least one of IL-12, IL-10, IL-1, IL-6, IL-8, CCL-2 and TNF-α and more preferably at least one of IL-1, IL-6, IL-8 and TNF-α.

In a further embodiment, the compound of the invention may be further administered in combination with an (a different) anti-viral agent. The anti-viral agent may be administered concurrently, sequentially or separately to administration of a compound of the invention. In this example, the compound of the invention may be used as an anti-inflammatory to treat inflammation or hyperinflammation associated or as a consequence of the viral infection.

In another aspect of the invention, there is provided a compound as defined herein, for use in the treatment of a disorder caused by a virus selected from the Orthomyxoviridae family or wherein the virus is West Nile virus, wherein the disorder is selected from neuroinflammation, pneumonia and immunopathology, in particular hypercytokinemia (cytokine storm syndrome), and sepsis. In another aspect of the invention, there is provided the use of a compound as defined herein, in the manufacture of a medicament for the treatment of a disorder caused by virus selected from the Orthomyxoviridae family or wherein the virus is West Nile virus, wherein the disorder is selected from neuroinflammation, pneumonia and immunopathology, in particular hypercytokinemia (cytokine storm syndrome), and sepsis. In another aspect of the invention, there is provided a method for the treatment of a disorder caused by virus selected from the Orthomyxoviridae family or wherein the virus is West Nile virus, wherein the disorder is selected from neuroinflammation, pneumonia and immunopathology, in particular hypercytokinemia (cytokine storm syndrome) and sepsis, the method comprising administering to an individual in need thereof a therapeutically effective amount of a compound as defined herein. In a particularly preferred embodiment, the disorder is immunopathology and in particular, hypercytokinemia.

In another aspect of the invention, there is provided a compound as defined herein, for use in the treatment of pneumonia and immunopathology, caused by influenza, in particular hypercytokinemia (cytokine storm syndrome), and sepsis. In another aspect of the invention, there is provided the use of a compound as defined herein, in the manufacture of a medicament for the treatment of pneumonia and immunopathology, caused by influenza, in particular hypercytokinemia (cytokine storm syndrome), and sepsis. In another aspect of the invention, there is provided a method for the treatment of pneumonia and immunopathology, caused by influenza, in particular hypercytokinemia (cytokine storm syndrome) and sepsis, the method comprising administering to an individual in need thereof a therapeutically effective amount of a compound as defined herein. In a particularly preferred embodiment, the disorder is immunopathology and in particular, hypercytokinemia.

In another aspect of the invention, there is provided a compound as defined herein, for use in the treatment of neuroinflammation or immunopathology, caused by West Nile virus, in particular hypercytokinemia (cytokine storm syndrome), and sepsis. In another aspect of the invention, there is provided the use of a compound as defined herein, in the manufacture of a medicament for the treatment of neuroinflammation or immunopathology, caused by West Nile virus, in particular hypercytokinemia (cytokine storm syndrome), and sepsis. In another aspect of the invention, there is provided a method for the treatment neuroinflammation or immunopathology, caused by West Nile virus, in particular hypercytokinemia (cytokine storm syndrome) and sepsis, the method comprising administering to an individual in need thereof a therapeutically effective amount of a compound as defined herein. In a particularly preferred embodiment, the disorder is immunopathology and in particular, hypercytokinemia.

In one embodiment, the Orthomyxoviridae virus is selected from Influenzavirus A, Influenzavirus B, Influenzavirus C, Thogotovirus, Quaranjavirus, and Isavirus. In another embodiment, the Orthomyxoviridae virus is Influenza A, preferably selected from H1N1, H1N2 and H3N2 sub-types. In another embodiment, the Orthomyxoviridae virus is influenza B, preferably selected from the Yamagata or Victoria lineages.

In one embodiment, the West Nile virus is selected from lineage 1, 2, 3, 4, 5, 6, 7 or 8. Preferably the virus is lineage 1 or 2 (WNV-1 or WNV-2).

Compounds of the invention may be used in pharmaceutical compositions having biological/pharmacological activity for the treatment of the above mentioned conditions. These pharmaceutical compositions comprise a compound of the invention together with a pharmaceutically acceptable carrier. The term "carrier" refers to a diluent, adjuvant, excipient or vehicle with which the active ingredient is administered. Suitable pharmaceutical carriers are described in “Remington’s Pharmaceutical Sciences” by E. W. Martin, 1995. Examples of pharmaceutical compositions include any solid (tablets, pills, capsules, granules, etc.) or liquid (solutions, suspensions, emulsions, etc.) compositions for oral, topical or parenteral administration. Pharmaceutical compositions containing compounds of the invention may be delivered by liposome or nanosphere encapsulation, in sustained release formulations or by other standard delivery means.

An exemplary composition is in the form of powder for solution for infusion. For example, compositions as described in WO9942125. For example, a lyophilised preparation of a compound of the invention including water-soluble material and secondly a reconstitution solution of mixed solvents. A particular example is a lyophilised preparation of PLD and mannitol and a reconstitution solution of mixed solvents, for example PEG-35 castor oil, ethanol and water for injections. Each vial, for example may contain 2 mg of PLD. After reconstitution, each mL of reconstituted solution may contain: 0.5 mg of PLD, 158 mg of PEG-35 castor oil, and ethanol 0.15 mL/mL.

The specific dosage and treatment regimen for any particular patient may be varied and will depend upon a variety of factors, including the activity of the specific compound employed, the particular formulation being used, the mode of application, the age, body weight, general health, sex, diet, time of administration, rate of excretion, drug combination, reaction sensitivities, and the severity of the particular disease or condition being treated.

In embodiments of the invention, the compounds of the present invention may be administered according to a dosing regimen of a daily dose.

In embodiments of the invention, the compounds of the present invention may be administered according to a dosing regimen of a once daily dose.

In further embodiments, the compounds of the present invention may be administered according to a dosing regimen of a daily dose for 10 days, 9 days, 8 days, 7 days, 6 days, 5 days, 4 days, 3 days, 2 days or 1 day. Preferred regimen is 2-5 days, or 3-5 days, or 3, 4 or 5 days, most preferably 3 days or 5 days.

The dose may be a dose of 5 mg a day or less, 4.5 mg a day or less, 4 mg a day or less, 3.5 mg a day or less, 3 mg a day or less, 2.5 mg a day or less or 2 mg a day or less.

Particular doses include 0.5 mg/day, 1 mg/day, 1.5 mg/day, 2 mg/day, 2.5 mg/day, 3 mg/day, 3.5 mg/day, 4 mg/day, 4.5 mg/day, or 5 mg/day. Preferred doses are 1 mg/day, 1.5 mg/day, 2 mg/day and 2.5 mg/day.

In further embodiments, the compounds of the present invention may be administered according to a total dose of 1-50 mg, 1-40 mg, 1-30 mg, 1-20 mg, 1-15 mg, 3-15 mg, 3-12 mg, 4-12 mg, 4-10 mg, or 4.5-10 mg. Total doses may be 4 mg, 4.5 mg, 5 mg, 5.5 mg, 6 mg, 6.5 mg, 7 mg, 7.5 mg, 8 mg, 8.5 mg, 9 mg, 9.5 mg or 10 mg. Preferred total doses are 4.5 mg, 5 mg, 6 mg, 7.5 mg, 8 mg, 9 mg or 10 mg. The total dose may be split over 1, 2, 3, 4, 5, 6, 7, 8, 9 or 10 days, preferably 3 days or 5 days.

In a particular embodiment, the compounds of the present invention may be administered according to a dosing regimen of a once daily dose for 5 days, at a dose of 2.5 mg a day or less.

In a further embodiment, the compounds of the present invention may be administered according to a dosing regimen of a once daily dose for 5 days, at a dose of 2 mg a day or less.

In a further embodiment, the compounds of the present invention may be administered according to a dosing regimen of a once daily dose for 3 days, at a dose of 1.5 mg a day or less.

In a further embodiment, the compounds of the present invention may be administered according to a dosing regimen of a once daily dose for 3 days, at a dose of 2 mg a day or less.

In a further embodiment, the compounds of the present invention may be administered according to a dosing regimen of a once daily dose for 3 days, at a dose of 2.5 mg a day or less.

In a further embodiment, the compounds of the present invention may be administered according to a dosing regimen of a once daily dose for 3 days, at a dose of 1.5 mg a day.

In a further embodiment, the compounds of the present invention may be administered according to a dosing regimen of a once daily dose for 3 days, at a dose of 2.0 mg a day.

In a further embodiment, the compounds of the present invention may be administered according to a dosing regimen of a once daily dose for 3 days, at a dose of 2.5 mg a day.

In a further embodiment, the compounds of the present invention may be administered according to a dosing regimen of a once daily dose for 3 days, at a dose of 1.5 to 2.5 mg a day.

An alternative regimen is a single dose on day 1. The single dose may be 1-10 mg, 4-10 mg, 4.5-10 mg; 4 mg, 4.5 mg, 5 mg, 5.5 mg, 6 mg, 6.5 mg, 7 mg, 7.5 mg, 8 mg, 8.5 mg, 9 mg, 9.5 mg or 10 mg; preferably 4.5 mg, 5 mg, 6 mg, 7.5 mg, 8 mg, 9 mg or 10 mg; more preferably 5-9 mg, 6.5-8.5 mg, 7-8 mg or 7.5 mg.

In a further embodiment, the compounds of the present invention may be administered according to the present invention, wherein the compounds of the present invention are administered with a corticosteroid. Preferably the corticosteroid is dexamethasone.

The corticosteroid may be administered daily with the compounds of the present invention. Administration may be sequential, concurrent or consecutive. The corticosteroid may be further administered on the days following administration of compounds according to the present invention. By way of example, with a 3 day dosing regimen, the corticosteroid may be administered on days 1-3 and then further administered daily for 3, 4, 5, 6, 7, 8, 9 or 10 or more further days.

In a particular embodiment, the corticosteroid may be administered is administered on days 1-3 as an intravenous administration and then on days 6-10 as an oral administration. In a further embodiment, the dosage of corticosteroid may be higher during the co-administration phase with the compounds of the present invention, and is lowered during the subsequent days.

Particular dosing schedules include:

Plitidepsin 1.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

Plitidepsin 2.0 mg/day intravenous (IV) combined with dexamethasone 6.6 mg/day IV on Days 1 to 3, followed by dexamethasone 6 mg/day oral administration (PO)/

IV from Day 4 and up to Day 10 (as per physician judgement according to patient clinical condition and evolution).

Plitidepsin 2.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

In an embodiment, to avoid administration-related infusion reactions, patients may receive the following medications 20 to 30 minutes prior to starting the infusion with a compound according to the present invention:

Ondansetron 8 mg IV (or equivalent)

Diphenhydramine hydrochloride 25 mg IV (or equivalent)

Ranitidine 50 mg IV (or equivalent)

Dexamethasone 6.6 mg IV (which is included in the schedule above)

Additionally, on Days 4 and 5 patients treated with compounds according to the present invention may receive ondansetron 4 mg twice a day PO.

Doses of dexamethasone, ondansetron and ranitidine are herein defined on the basis of the base form. The dose of diphenhydramine hydrochloride is given on the basis of the hydrochloride salt. Doses of compounds of the invention are given on the basis of the base form.

The daily doses may be administered as an infusion. The infusion may be a 1 hour infusion, a 1.5 hour infusion, a 2 hour infusion, a 3 hour infusion or longer. Preferably, the infusion is 1.5 hours.

In certain embodiments, the dose may be administered according to a regimen which uses a loading dose and a maintenance dose. Loading/maintenance doses according to the present invention includes:

a loading dose of 2.5 mg for day 1, and followed by a maintenance dose of 2 mg/day for subsequent days;

a loading dose of 2.5 mg for day 1, and followed by a maintenance dose of 1.5 mg/day for subsequent days;

a loading dose of 2.5 mg for day 1, and followed by a maintenance dose of 1 mg/day for subsequent days;

a loading dose of 2.5 mg for day 1, and followed by a maintenance dose of 0.5 mg/day for subsequent days;

a loading dose of 2 mg for day 1, and followed by a maintenance dose of 1.5 mg/day for subsequent days;

a loading dose of 2 mg for day 1, and followed by a maintenance dose of 1 mg/day for subsequent days;

a loading dose of 2 mg for day 1, and followed by a maintenance dose of 0.5 mg/day for subsequent days;

a loading dose of 1.5 mg for day 1, and followed by a maintenance dose of 1 mg/day for subsequent days;

a loading dose of 1.5 mg for day 1, and followed by a maintenance dose of 0.5 mg/day for subsequent days; and a loading dose of 1 mg for day 1, and followed by a maintenance dose of 0.5 mg/day for subsequent days.

According to a further embodiment, the daily dose may be reduced in the final day or days of the regimen.

According to a further embodiment, if the daily dose is 2 mg, the dose may be reduced to 1 mg on days 4 and 5.

Particular regimens include:

1 mg of plitidepsin administered as a 1.5-hour infusion, once a day for 5 consecutive days (total dose 5 mg);

2 mg of plitidepsin administered as a 1.5-hour infusion, once a day for 5 consecutive days. At the discretion of the researcher, the dose may be reduced to 1 mg/day on days 4 and 5 (total dose 8-10 mg);

1.5 mg of plitidepsin administered as a 1.5-hour infusion, once a day for 3 consecutive days (total dose 4.5 mg);

2 mg of plitidepsin administered in 1.5 hour infusion, once a day for 3 consecutive days. (total dose 6 mg); and 2.5 mg of plitidepsin administered as a 1.5-hour infusion, once a day for 3 consecutive days (total dose 7.5 mg).

A single dose regimen includes:

Plitidepsin administered as a 1.5-hour infusion, once on day 1 at a dose of 1-10 mg, 4-10 mg, 4.5-10 mg, 4 mg, 4.5 mg, 5 mg, 5.5 mg, 6 mg, 6.5 mg, 7 mg, 7.5 mg, 8 mg, 8.5 mg, 9 mg, 9.5 mg or 10 mg, preferably 4.5 mg, 5 mg, 6 mg, 7.5 mg, 8 mg, 9 mg or 10 mg, more preferably 5-9 mg, 6.5-8.5 mg, 7-8 mg or most preferably 7.5 mg.

The single dose regimen may further include the following prophylactic medications 20-30 minutes prior to plitidepsin infusion:

Diphenhydramine hydrochloride 25 mg i.v.,

Ranitidine 50 mg i.v.

Dexamethasone 6.6 mg intravenously.

Ondansetron 8 mg i.v. in slow infusion of 15 minutes

Ondansetron 4 mg orally may be given every 12 hours for 3 days after plitidepsin administration to relieve drug-induced nausea and vomiting. If plitidepsin is administered in the morning the patient may receive the first dose of ondansetron in the afternoon.

According to further embodiments, patients may be selected for treatment with compounds of the present invention based on clinical parameters and/or patient characteristics. Suitable parameters may be measurements disclosed in the present application.

The regimens and doses outlined above apply to both methods of treatment according to the present invention, use, and use of a compound as defined herein in the manufacture of medicaments as defined herein.

In embodiments, the present invention is directed to a compound for use according to the present invention, wherein the compound is administered in combination with one or more of the following prophylactic medications: diphenhydramine hydrochloride, ranitidine, dexamethasone, ondansetron. In particular, one or more of diphenhydramine hydrochloride 25 mg iv or equivalent; Ranitidine 50 mg iv or equivalent; Dexamethasone 8 mg intravenous; Ondansetron 8 mg i.v. in slow infusion of 15 minutes or equivalent. Patients may receive said prophylactic medications 20-30 minutes before the infusion of plitidepsin. Dexamethasone 8 mg intravenous may be dexamethasone phosphate leading to 6.6 mg dexamethasone base.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

EXAMPLES

Compounds of the present invention can be obtained according to the processes set out in the literature, for example: Vera et al. Med. Res. Rev. 2002, 22(2), 102-145, WO 2011/020913 (see in particular Examples 1-5), WO 02/02596, WO 01/76616, and WO 2004/084812, the contents of which are incorporated herein by reference.

Particular compounds used in experiments of the present invention are:

| Compound | Structure |
|---|---|
| PLD | 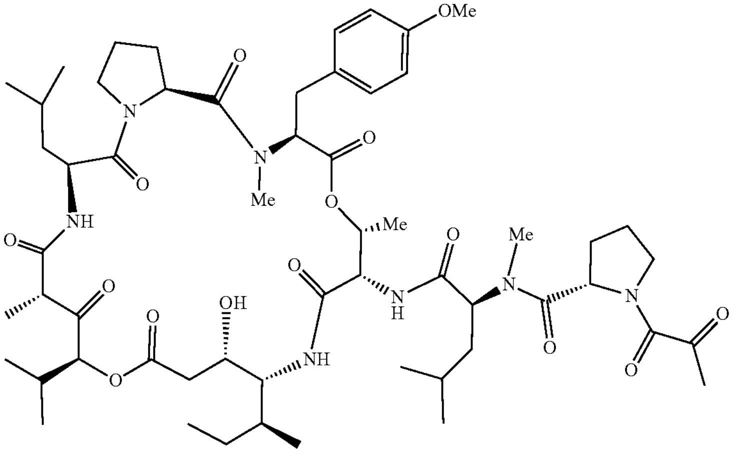 [SMILES: CC[C@H](C)[C@H]1NC(=O)[C@@H](NC(=O)[C@H](CC(C)C)N(C)C(=O)[C@@H]2CCCN2C(=O)C(C)=O)[C@@H](C)OC(=O)[C@H](Cc2ccc(OC)cc2)N(C)C(=O)[C@@H]2CCCN2C(=O)[C@H](CC(C)C)NC(=O)[C@@H](C)C(=O)[C@H](C(C)C)OC(=O)C[C@@H]1O] |
| DidemninB (compound 240) | 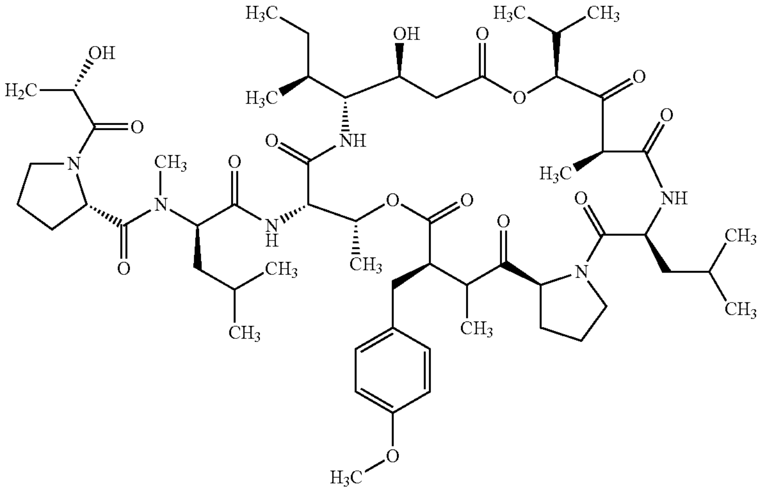 [SMILES: CC[C@H](C)[C@H]1NC(=O)[C@@H](NC(=O)[C@@H](CC(C)C)N(C)C(=O)[C@@H]2CCCN2C(=O)[C@H](C)O)[C@@H](C)OC(=O)[C@H](Cc2ccc(OC)cc2)C(C)C(=O)[C@@H]2CCCN2C(=O)[C@H](CC(C)C)NC(=O)[C@@H](C)C(=O)[C@H](C(C)C)OC(=O)C[C@@H]1O] |
| Compound 3 | 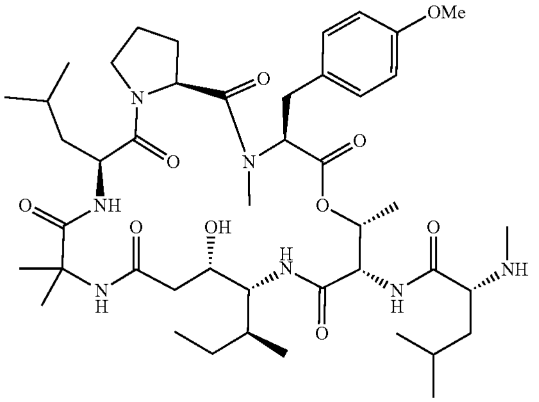 [SMILES: CC[C@H](C)[C@H]1NC(=O)[C@@H](NC(=O)[C@@H](CC(C)C)NC)[C@@H](C)OC(=O)[C@H](Cc2ccc(OC)cc2)N(C)C(=O)[C@@H]2CCCN2C(=O)[C@H](CC(C)C)NC(=O)C(C)(C)NC(=O)C[C@@H]1O] |

-continued
| Compound | Structure |
|---|---|
| Compound 8 | 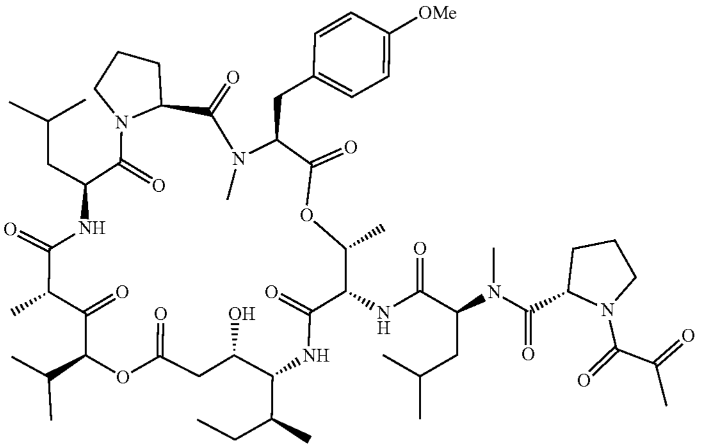 [SMILES: CC[C@H](C)[C@H]1NC(=O)[C@@H](NC(=O)[C@H](CC(C)C)N(C)C(=O)[C@@H]2CCCN2C(=O)C(C)=O)[C@@H](C)OC(=O)[C@H](Cc2ccc(OC)cc2)N(C)C(=O)[C@@H]2CCCN2C(=O)[C@H](CC(C)C)NC(=O)[C@@H](C)C(=O)[C@H](C(C)C)OC(=O)C[C@@H]1O] |
| Compound 9 | 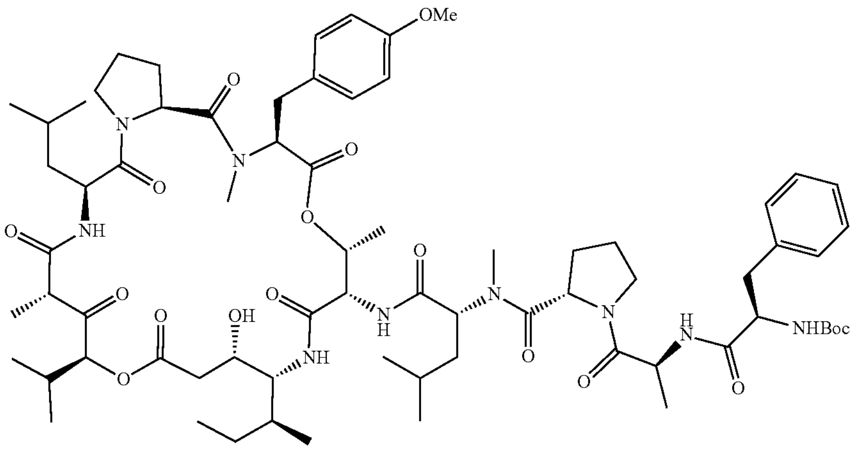 [SMILES: CC[C@H](C)[C@H]1NC(=O)[C@@H](NC(=O)[C@@H](CC(C)C)N(C)C(=O)[C@@H]2CCCN2C(=O)[C@H](C)NC(=O)[C@@H](Cc2ccccc2)NC(=O)OC(C)(C)C)[C@@H](C)OC(=O)[C@H](Cc2ccc(OC)cc2)N(C)C(=O)[C@@H]2CCCN2C(=O)[C@H](CC(C)C)NC(=O)[C@@H](C)C(=O)[C@H](C(C)C)OC(=O)C[C@@H]1O] |
| Compound 10 | 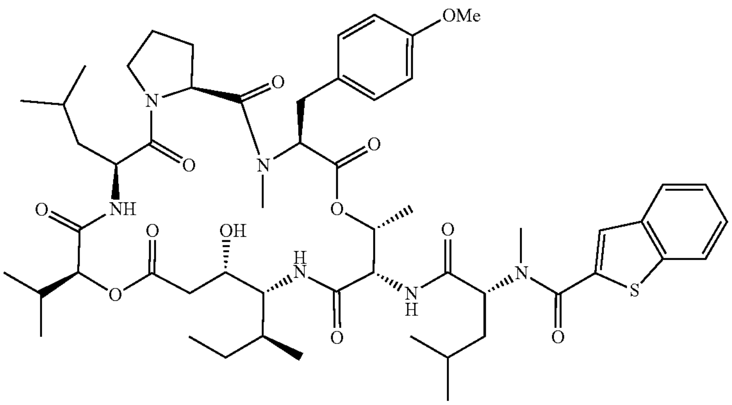 [SMILES: CC[C@H](C)[C@H]1NC(=O)[C@@H](NC(=O)[C@@H](CC(C)C)N(C)C(=O)c2cc3ccccc3s2)[C@@H](C)OC(=O)[C@H](Cc2ccc(OC)cc2)N(C)C(=O)[C@@H]2CCCN2C(=O)[C@H](CC(C)C)NC(=O)[C@H](C(C)C)OC(=O)C[C@@H]1O] |

-continued
| Compound | Structure |
|---|---|
| Compound 11 | 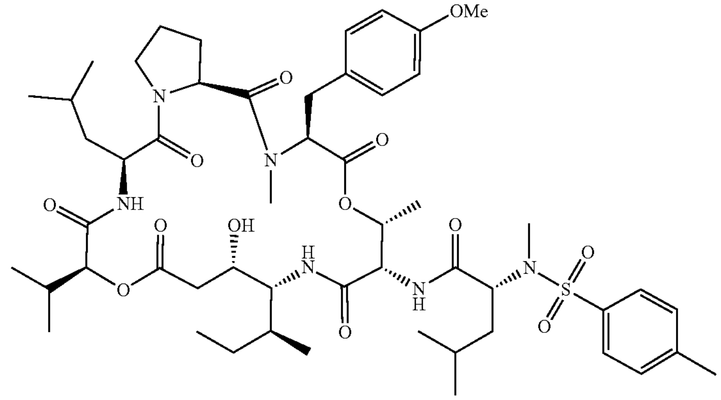 [SMILES: CC[C@H](C)[C@H]1NC(=O)[C@@H](NC(=O)[C@@H](CC(C)C)N(C)S(=O)(=O)c2ccc(C)cc2)[C@@H](C)OC(=O)[C@H](Cc2ccc(OC)cc2)N(C)C(=O)[C@@H]2CCCN2C(=O)[C@H](CC(C)C)NC(=O)[C@H](C(C)C)OC(=O)C[C@@H]1O] |
Following the procedures described in WO 02/02596 and in the specification, and further disclosed in the previous examples, the following compounds are obtainable:
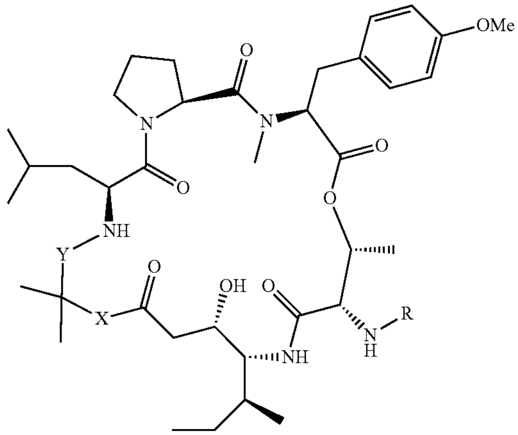
| Compound | X | Y | R |
|---|---|---|---|
| 12 | O | CO | 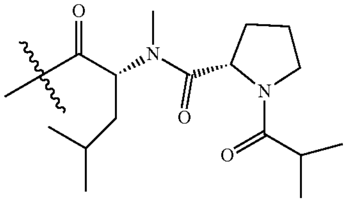 [SMILES: *C(=O)[C@@H](CC(C)C)N(C)C(=O)[C@@H]1CCCN1C(=O)C(C)C] |
| 13 | NH | CO | |
| 14 | O | —COCH($CH_3$)CO— | |
| 15 | NH | —COCH($CH_3$)CO— | |
| 16 | O | CO | 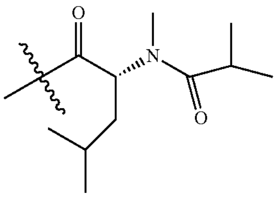 [SMILES: *C(=O)[C@@H](CC(C)C)N(C)C(=O)C(C)C] |
| 17 | NH | CO | |
| 18 | O | —COCH($CH_3$)CO— | |
| 19 | NH | —COCH($CH_3$)CO— | |

-continued
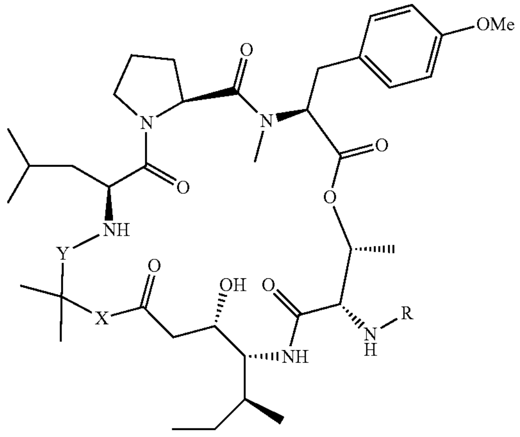
| Compound | X | Y | R |
|---|---|---|---|
| 20 | O | CO | 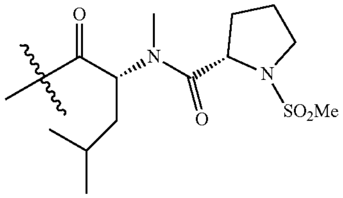 [SMILES: *C(=O)[C@@H](CC(C)C)N(C)C(=O)[C@@H]1CCCN1S(C)(=O)=O] |
| 21 | NH | CO | |
| 22 | O | —COCH($CH_3$)CO— | |
| 23 | NH | —COCH($CH_3$)CO— | |
| 24 | O | CO | 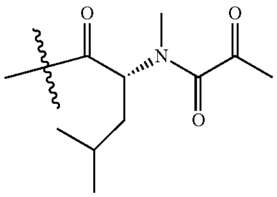 [SMILES: *C(=O)[C@@H](CC(C)C)N(C)C(=O)C(C)=O] |
| 25 | NH | CO | |
| 26 | O | —COCH($CH_3$)CO— | |
| 27 | NH | —COCH($CH_3$)CO— | |
| 28 | O | CO | 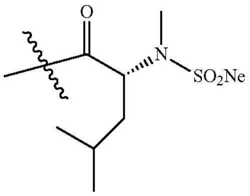 |
| 29 | NH | CO | |
| 30 | O | —COCH($CH_3$)CO— | |
| 31 | NH | —COCH($CH_3$)CO— | |
| 32 | O | CO | 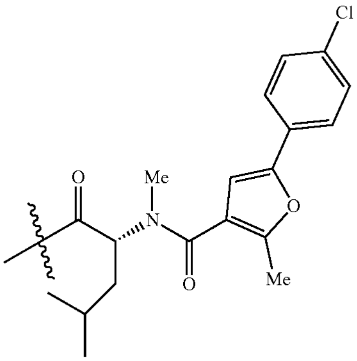 [SMILES: *C(=O)[C@@H](CC(C)C)N(C)C(=O)c1cc(-c2ccc(Cl)cc2)oc1C] |
| 33 | NH | CO | |
| 34 | O | —COCH($CH_3$)CO— | |
| 35 | NH | —COCH($CH_3$)CO— | |

-continued
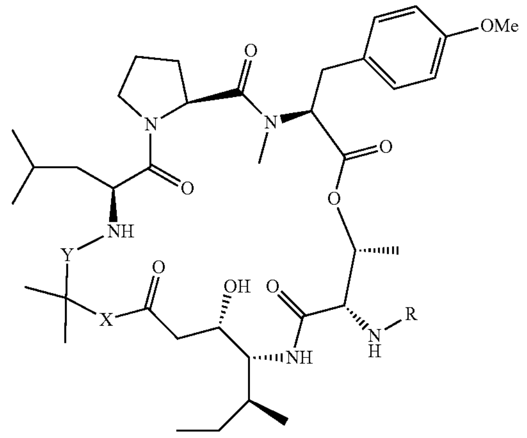
| Compound | X | Y | R |
| --- | --- | --- | --- |
| 36 | O | CO | 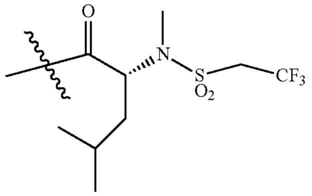 [SMILES: *C(=O)[C@@H](CC(C)C)N(C)S(=O)(=O)CC(F)(F)F] |
| 37 | NH | CO | |
| 38 | O | —COCH($CH_3$)CO— | |
| 39 | NH | —COCH($CH_3$)CO— | |
| 40 | O | CO | 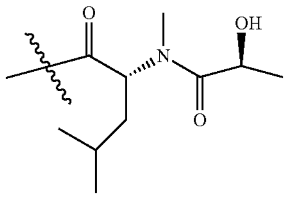 [SMILES: *C(=O)[C@@H](CC(C)C)N(C)C(=O)[C@H](C)O] |
| 41 | NH | CO | |
| 42 | O | —COCH($CH_3$)CO— | |
| 43 | NH | —COCH($CH_3$)CO— | |
| 44 | O | CO | 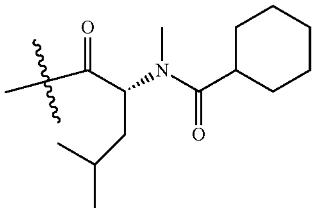 [SMILES: *C(=O)[C@@H](CC(C)C)N(C)C(=O)C1CCCCC1] |
| 45 | NH | CO | |
| 46 | O | —COCH($CH_3$)CO— | |
| 47 | NH | —COCH($CH_3$)CO— | |
| 48 | O | CO | 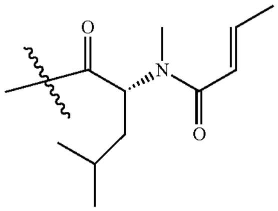 [SMILES: *C(=O)[C@@H](CC(C)C)N(C)C(=O)/C=C/C] |
| 49 | NH | CO | |
| 50 | O | —COCH($CH_3$)CO— | |
| 51 | NH | —COCH($CH_3$)CO— | |
| 52 | O | CO | 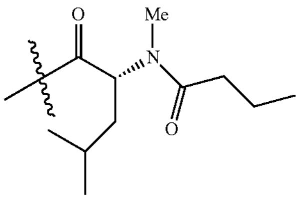 [SMILES: *C(=O)[C@@H](CC(C)C)N(C)C(=O)CCC] |
| 53 | NH | CO | |
| 54 | O | —COCH($CH_3$)CO— | |
| 55 | NH | —COCH($CH_3$)CO— | |

-continued
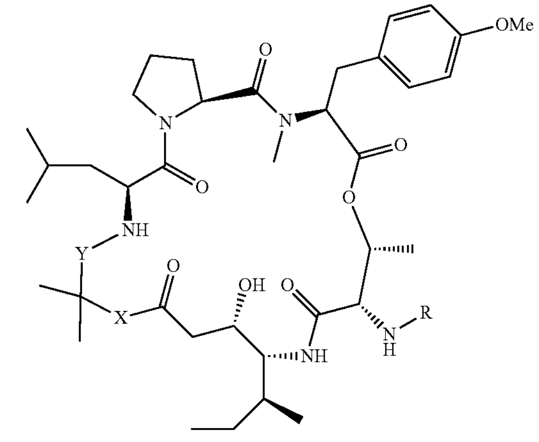
| Compound | X | Y | R |
|---|---|---|---|
| 56 | O | CO | 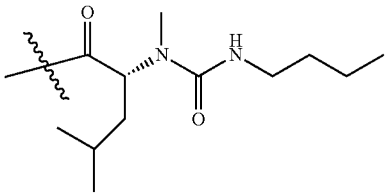 [SMILES: *C(=O)[C@@H](CC(C)C)N(C)C(=O)NCCCC] |
| 57 | NH | CO | |
| 58 | O | —COCH($CH_3$)CO— | |
| 59 | NH | —COCH($CH_3$)CO— | |
| 60 | O | CO | 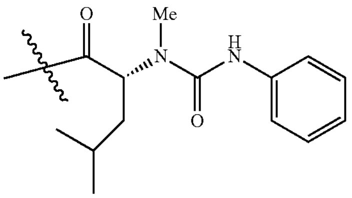 [SMILES: *C(=O)[C@@H](CC(C)C)N(C)C(=O)Nc1ccccc1] |
| 61 | NH | CO | |
| 62 | O | —COCH($CH_3$)CO— | |
| 63 | NH | —COCH($CH_3$)CO— | |
| 64 | O | CO | 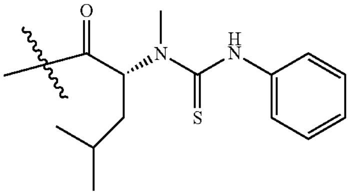 [SMILES: *C(=O)[C@@H](CC(C)C)N(C)C(=S)Nc1ccccc1] |
| 65 | NH | CO | |
| 66 | O | —COCH($CH_3$)CO— | |
| 67 | NH | —COCH($CH_3$)CO— | |
| 68 | O | CO | 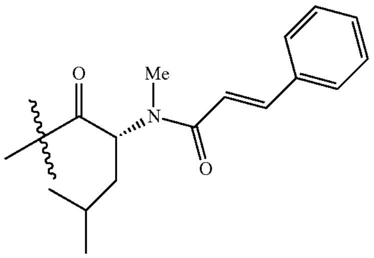 [SMILES: *C(=O)[C@@H](CC(C)C)N(C)C(=O)/C=C/c1ccccc1] |
| 69 | NH | CO | |
| 70 | O | —COCH($CH_3$)CO— | |
| 71 | NH | —COCH($CH_3$)CO— | |
| 72 | O | CO | 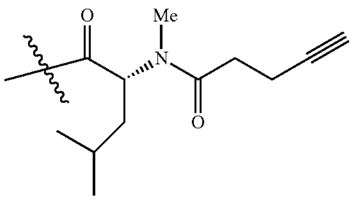 [SMILES: *C(=O)[C@@H](CC(C)C)N(C)C(=O)CCC#C] |
| 73 | NH | CO | |
| 74 | O | —COCH($CH_3$)CO— | |
| 75 | NH | —COCH($CH_3$)CO— | |

-continued
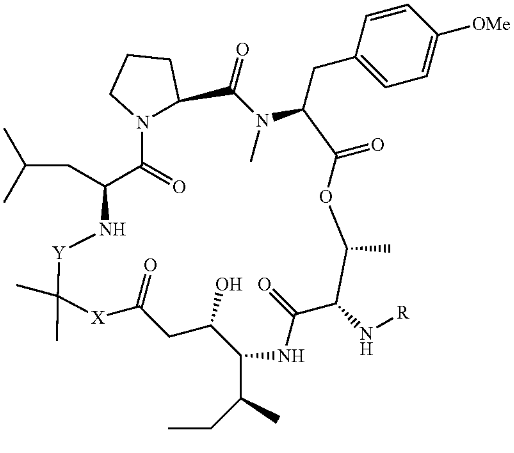
| Compound | X | Y | R |
|---|---|---|---|
| 76 | O | CO | 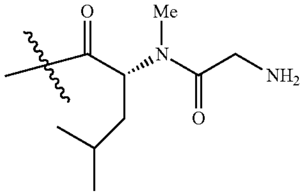 [SMILES: *C(=O)[C@@H](CC(C)C)N(C)C(=O)CN] |
| 77 | NH | CO | |
| 78 | O | —COCH($CH_3$)CO— | |
| 79 | NH | —COCH($CH_3$)CO— | |
| 80 | O | CO | 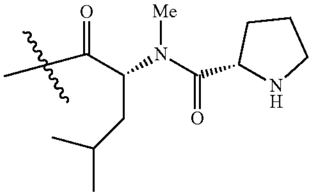 [SMILES: *C(=O)[C@@H](CC(C)C)N(C)C(=O)[C@@H]1CCCN1] |
| 81 | NH | CO | |
| 82 | O | —COCH($CH_3$)CO— | |
| 83 | NH | —COCH($CH_3$)CO— | |
| 84 | O | CO | 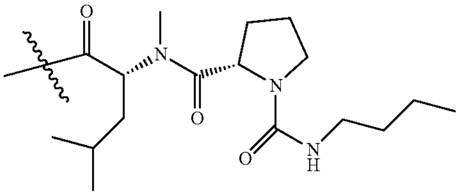 [SMILES: *C(=O)[C@@H](CC(C)C)N(C)C(=O)[C@@H]1CCCN1C(=O)NCCCC] |
| 85 | NH | CO | |
| 86 | O | —COCH($CH_3$)CO— | |
| 87 | NH | —COCH($CH_3$)CO— | |
| 88 | O | CO | 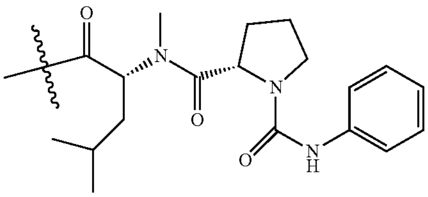 [SMILES: *C(=O)[C@@H](CC(C)C)N(C)C(=O)[C@@H]1CCCN1C(=O)Nc1ccccc1] |
| 89 | NH | CO | |
| 90 | O | —COCH($CH_3$)CO— | |
| 91 | NH | —COCH($CH_3$)CO— | |
| 92 | O | CO | 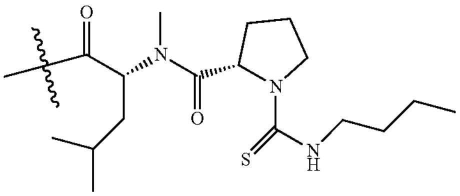 [SMILES: *C(=O)[C@@H](CC(C)C)N(C)C(=O)[C@@H]1CCCN1C(=S)NCCCC] |
| 93 | NH | CO | |
| 94 | O | —COCH($CH_3$)CO— | |
| 95 | NH | —COCH($CH_3$)CO— | |

-continued
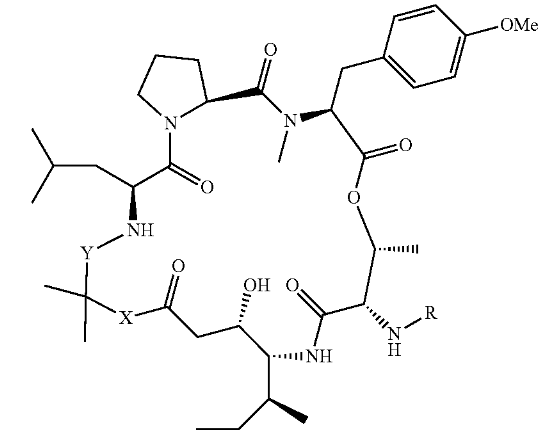
| Compound | X | Y | R |
|---|---|---|---|
| 96 | O | CO | 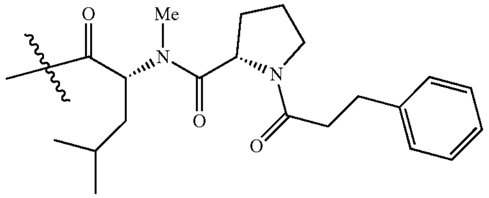 [SMILES: *C(=O)[C@@H](CC(C)C)N(C)C(=O)[C@@H]1CCCN1C(=O)CCc1ccccc1] |
| 97 | NH | CO | |
| 98 | O | —COCH($CH_3$)CO— | |
| 99 | NH | —COCH($CH_3$)CO— | |
| 100 | O | CO | 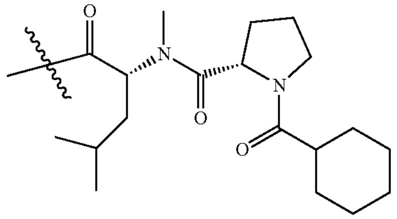 [SMILES: *C(=O)[C@@H](CC(C)C)N(C)C(=O)[C@@H]1CCCN1C(=O)C1CCCCC1] |
| 101 | NH | CO | |
| 102 | O | —COCH($CH_3$)CO— | |
| 103 | NH | —COCH($CH_3$)CO— | |
| 104 | O | CO | 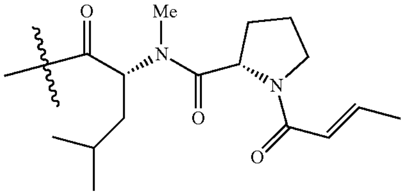 [SMILES: *C(=O)[C@@H](CC(C)C)N(C)C(=O)[C@@H]1CCCN1C(=O)/C=C/C] |
| 105 | NH | CO | |
| 106 | O | —COCH($CH_3$)CO— | |
| 107 | NH | —COCH($CH_3$)CO— | |
| 108 | O | CO | 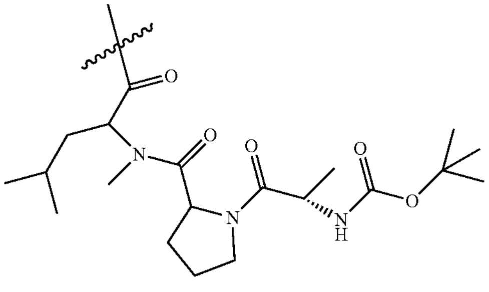 [SMILES: *C(=O)C(CC(C)C)N(C)C(=O)C1CCCN1C(=O)[C@H](C)NC(=O)OC(C)(C)C] |
| 109 | NH | CO | |
| 110 | O | —COCH($CH_3$)CO— | |
| 111 | NH | —COCH($CH_3$)CO— | |
| 112 | O | CO | 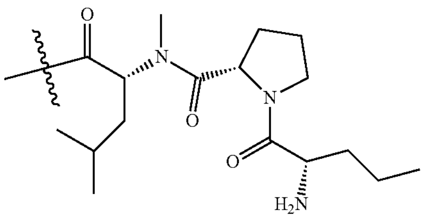 [SMILES: *C(=O)[C@@H](CC(C)C)N(C)C(=O)[C@@H]1CCCN1C(=O)[C@@H](N)CCC] |
| 113 | NH | CO | |
| 114 | O | —COCH($CH_3$)CO— | |
| 115 | NH | —COCH($CH_3$)CO— | |

-continued
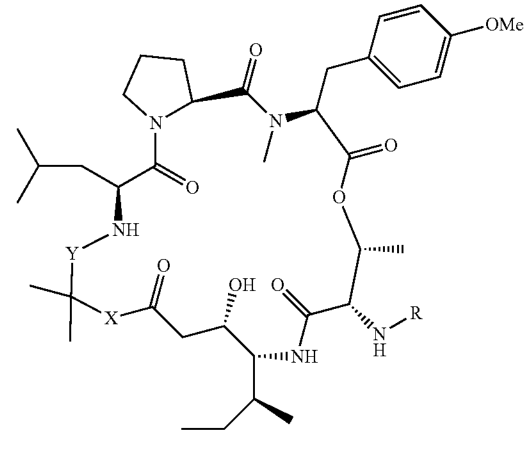
| Compound | X | Y | R |
|---|---|---|---|
| 116 | O | CO | 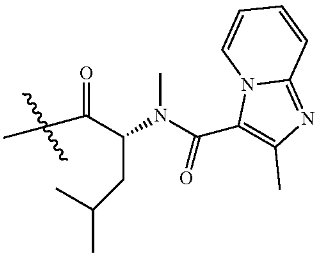 [SMILES: *C(=O)[C@@H](CC(C)C)N(C)C(=O)c1c(C)nc2ccccn12] |
| 117 | NH | CO | |
| 118 | O | —COCH($CH_3$)CO— | |
| 119 | NH | —COCH($CH_3$)CO— | |
| 120 | O | CO | 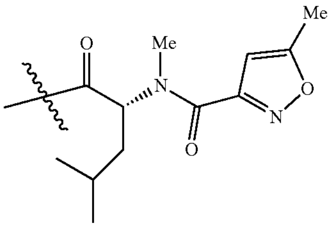 [SMILES: *C(=O)[C@@H](CC(C)C)N(C)C(=O)c1cc(C)on1] |
| 121 | NH | CO | |
| 122 | O | —COCH($CH_3$)CO— | |
| 123 | NH | —COCH($CH_3$)CO— | |
| 124 | O | CO | 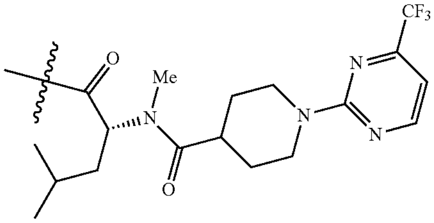 [SMILES: *C(=O)[C@@H](CC(C)C)N(C)C(=O)C1CCN(c2nccc(C(F)(F)F)n2)CC1] |
| 125 | NH | CO | |
| 126 | O | —COCH($CH_3$)CO— | |
| 127 | NH | —COCH($CH_3$)CO— | |
| 128 | O | CO | 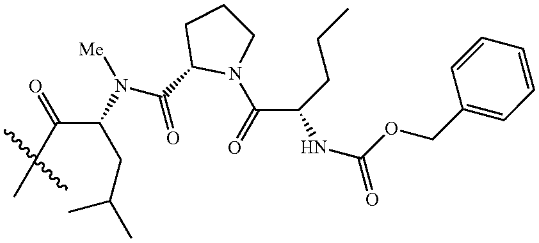 [SMILES: *C(=O)[C@@H](CC(C)C)N(C)C(=O)[C@@H]1CCCN1C(=O)[C@H](CCC)NC(=O)OCc1ccccc1] |
| 129 | NH | CO | |
| 130 | O | —COCH($CH_3$)CO— | |
| 131 | NH | —COCH($CH_3$)CO— | |

Following the procedures described in WO 02/02596 and in the specification, and further disclosed in the previous examples, the following compounds are obtainable:

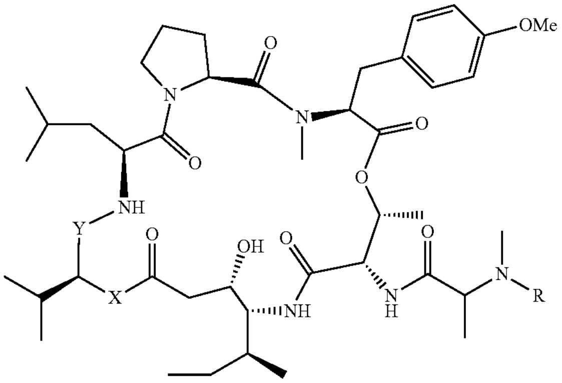

| Compound | X | Y | R |
|---|---|---|---|
| 132 | O | CO | 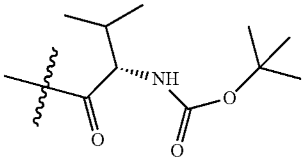 [SMILES: *C(=O)[C@@H](NC(=O)OC(C)(C)C)C(C)C] |
| 133 | NH | CO | |
| 134 | O | —COCH($CH_3$)CO— | |
| 135 | NH | —COCH($CH_3$)CO— | |
| 136 | O | CO | 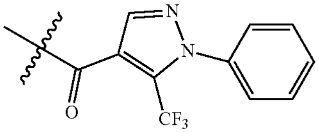 [SMILES: *C(=O)c1cnn(-c2ccccc2)c1C(F)(F)F] |
| 137 | NH | CO | |
| 138 | O | —COCH($CH_3$)CO— | |
| 139 | NH | —COCH($CH_3$)CO— | |
| 140 | O | CO | 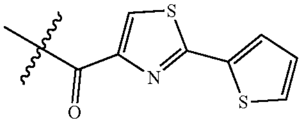 [SMILES: *C(=O)c1csc(-c2cccs2)n1] |
| 141 | NH | CO | |
| 142 | O | —COCH($CH_3$)CO— | |
| 143 | NH | —COCH($CH_3$)CO— | |
| 144 | O | CO | 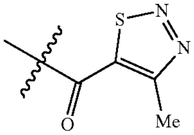 [SMILES: *C(=O)c1snnc1C] |
| 145 | NH | CO | |
| 146 | O | —COCH($CH_3$)CO— | |
| 147 | NH | —COCH($CH_3$)CO— | |
| 148 | O | CO | 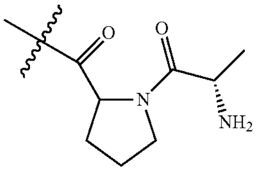 [SMILES: *C(=O)C1CCCN1C(=O)[C@H](C)N] |
| 149 | NH | CO | |
| 150 | O | —COCH($CH_3$)CO— | |
| 151 | NH | —COCH($CH_3$)CO— | |
| 152 | O | CO | 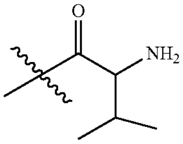 [SMILES: *C(=O)C(N)C(C)C] |
| 153 | NH | CO | |
| 154 | O | —COCH($CH_3$)CO— | |
| 155 | NH | —COCH($CH_3$)CO— | |
| 156 | O | CO | 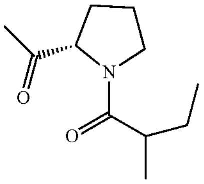 |
| 157 | NH | CO | |
| 158 | O | —COCH($CH_3$)CO— | |
| 159 | NH | —COCH($CH_3$)CO— | |

-continued
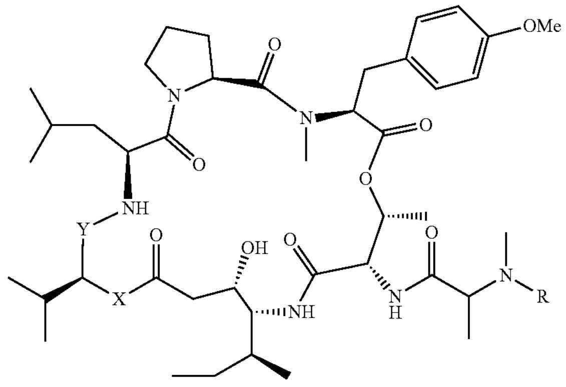
| Compound | X | Y | R |
|---|---|---|---|
| 160 | O | CO | 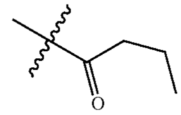 [SMILES: *C(=O)CCC] |
| 161 | NH | CO | |
| 162 | O | —COCH($CH_3$)CO— | |
| 163 | NH | —COCH($CH_3$)CO— | |
| 164 | O | CO | 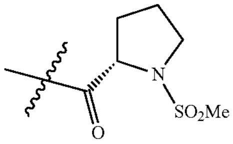 [SMILES: *C(=O)[C@@H]1CCCN1S(C)(=O)=O] |
| 165 | NH | CO | |
| 166 | O | —COCH($CH_3$)CO— | |
| 167 | NH | —COCH($CH_3$)CO— | |
| 168 | O | CO | 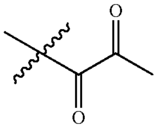 [SMILES: *C(=O)C(C)=O] |
| 169 | NH | CO | |
| 170 | O | —COCH($CH_3$)CO— | |
| 171 | NH | —COCH($CH_3$)CO— | |
| 172 | O | CO | 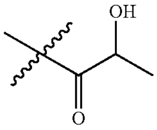 [SMILES: *C(=O)C(C)O] |
| 173 | NH | CO | |
| 174 | O | —COCH($CH_3$)CO— | |
| 175 | NH | —COCH($CH_3$)CO— | |
| 176 | O | CO | —$SO_2$Me |
| 177 | NH | CO | |
| 178 | O | —COCH($CH_3$)CO— | |
| 179 | NH | —COCH($CH_3$)CO— | |
| 180 | O | CO | 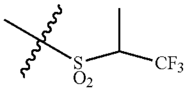 |
| 181 | NH | CO | |
| 182 | O | —COCH($CH_3$)CO— | |
| 183 | NH | —COCH($CH_3$)CO— | |
| 184 | O | CO | 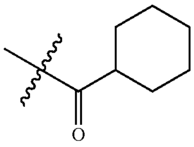 [SMILES: *C(=O)C1CCCCC1] |
| 185 | NH | CO | |
| 186 | O | —COCH($CH_3$)CO— | |
| 187 | NH | —COCH($CH_3$)CO— | |
| 188 | O | CO | 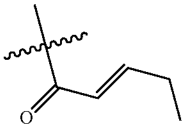 [SMILES: *C(=O)/C=C/CC] |
| 189 | NH | CO | |
| 190 | O | —COCH($CH_3$)CO— | |
| 191 | NH | —COCH($CH_3$)CO— | |

-continued
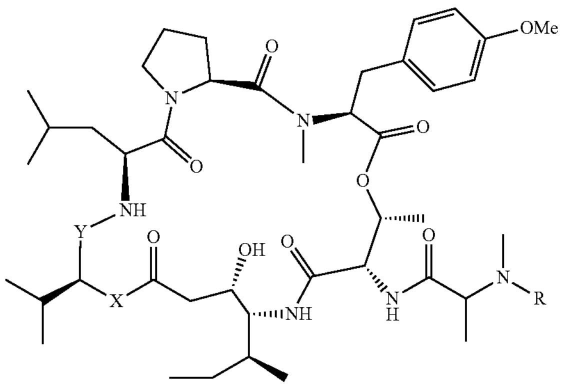
| Compound | X | Y | R |
|---|---|---|---|
| 192 | O | CO | 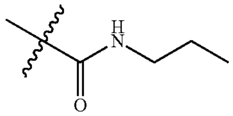 [SMILES: *C(=O)NCCC] |
| 193 | NH | CO | |
| 194 | O | —COCH($CH_3$)CO— | |
| 195 | NH | —COCH($CH_3$)CO— | |
| 196 | O | CO | 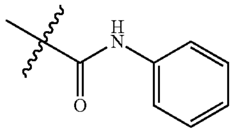 [SMILES: *C(=O)Nc1ccccc1] |
| 197 | NH | CO | |
| 198 | O | —COCH($CH_3$)CO— | |
| 199 | NH | —COCH($CH_3$)CO— | |
| 200 | O | CO | 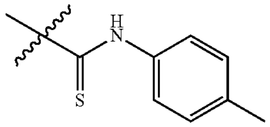 [SMILES: *C(=S)Nc1ccc(C)cc1] |
| 201 | NH | CO | |
| 202 | O | —COCH($CH_3$)CO— | |
| 203 | NH | —COCH($CH_3$)CO— | |
| 204 | O | CO | 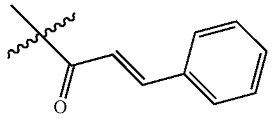 [SMILES: *C(=O)/C=C/c1ccccc1] |
| 205 | NH | CO | |
| 206 | O | —COCH($CH_3$)CO— | |
| 207 | NH | —COCH($CH_3$)CO— | |
| 208 | O | CO | 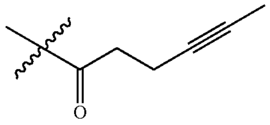 [SMILES: *C(=O)CCC#CC] |
| 209 | NH | CO | |
| 210 | O | —COCH($CH_3$)CO— | |
| 211 | NH | —COCH($CH_3$)CO— | |
| 212 | O | CO | 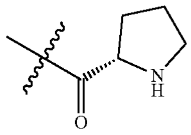 [SMILES: *C(=O)[C@@H]1CCCN1] |
| 213 | NH | CO | |
| 214 | O | —COCH($CH_3$)CO— | |
| 215 | NH | —COCH($CH_3$)CO— | |
| 216 | O | CO | 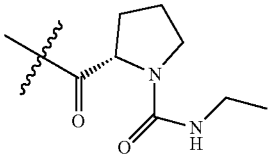 [SMILES: *C(=O)[C@@H]1CCCN1C(=O)NCC] |
| 217 | NH | CO | |
| 218 | O | —COCH($CH_3$)CO— | |
| 219 | NH | —COCH($CH_3$)CO— | |

-continued
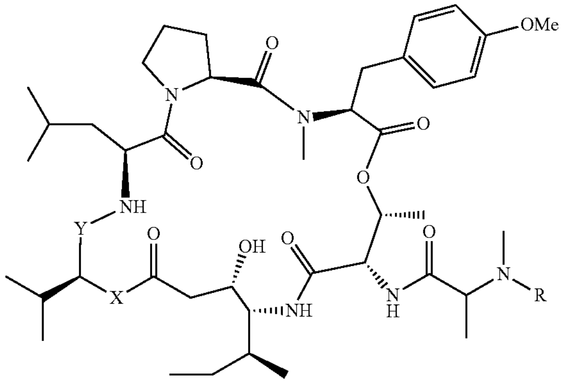
| Compound | X | Y | R |
|---|---|---|---|
| 220 | O | CO | 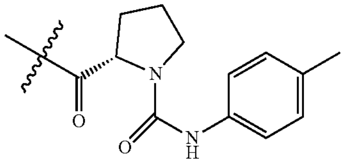 [SMILES: *C(=O)[C@@H]1CCCN1C(=O)Nc1ccc(C)cc1] |
| 221 | NH | CO | |
| 222 | O | —COCH($CH_3$)CO— | |
| 223 | NH | —COCH($CH_3$)CO— | |
| 224 | O | CO | 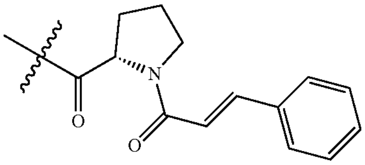 [SMILES: *C(=O)[C@@H]1CCCN1C(=O)/C=C/c1ccccc1] |
| 225 | NH | CO | |
| 226 | O | —COCH($CH_3$)CO— | |
| 227 | NH | —COCH($CH_3$)CO— | |
| 228 | O | CO | 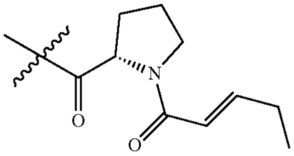 [SMILES: *C(=O)[C@@H]1CCCN1C(=O)/C=C/CC] |
| 229 | NH | CO | |
| 230 | O | —COCH($CH_3$)CO— | |
| 231 | NH | —COCH($CH_3$)CO— | |
| 232 | O | CO | 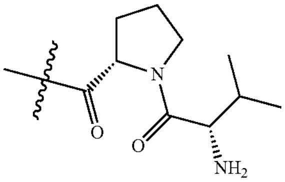 [SMILES: *C(=O)[C@@H]1CCCN1C(=O)[C@@H](N)C(C)C] |
| 233 | NH | CO | |
| 234 | O | —COCH($CH_3$)CO— | |
| 235 | NH | —COCH($CH_3$)CO— | |
| 236 | O | CO | 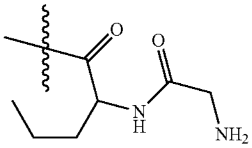 [SMILES: *C(=O)C(CCC)NC(=O)CN] |
| 237 | NH | CO | |
| 238 | O | —COCH($CH_3$)CO— | |
| 239 | NH | —COCH($CH_3$)CO— | |

A further compound is Compound 240, known as DidemninB and shown by the structure below:

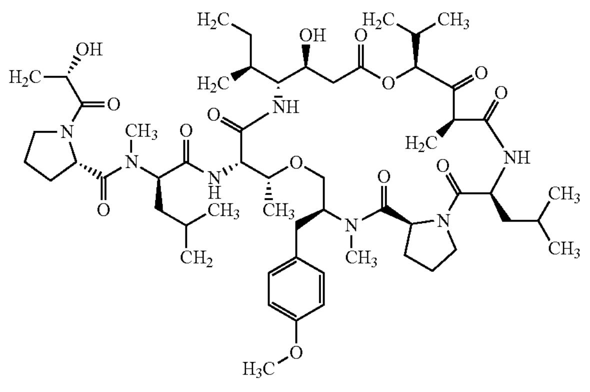 [SMILES: CC[C@H](C)[C@H]1NC(=O)[C@@H](NC(=O)[C@@H](CC(C)C)N(C)C(=O)[C@@H]2CCCN2C(=O)[C@H](C)O)[C@@H](C)OC[C@H](Cc2ccc(OC)cc2)N(C)C(=O)[C@@H]2CCCN2C(=O)[C@H](CC(C)C)NC(=O)[C@@H](C)C(=O)[C@H](C(C)C)OC(=O)C[C@@H]1O]

Example 1

Figure 1B:
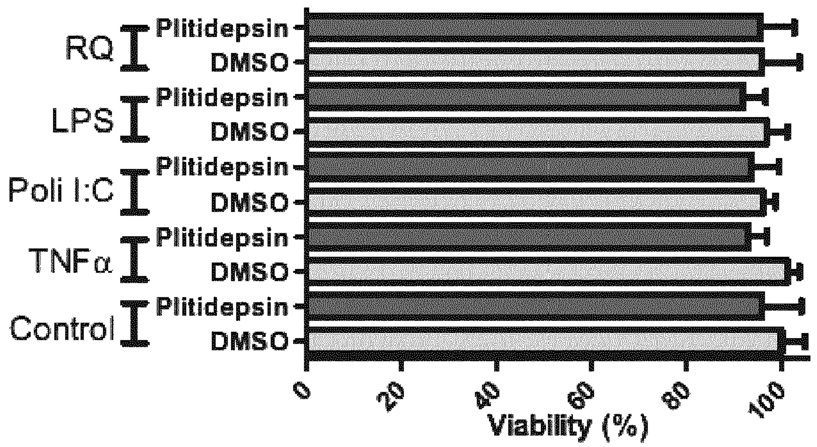

As shown in FIG. 1, PLD inhibits in vitro the transactivation of NF-κB.

We checked whether the transcriptional activity of NFκB was regulated by plitidepsin. To that end, we took advantage of THP-1 cells stably transfected with an NFκB luciferase reporter plasmid. We treated the cells with 100 ng/mL TNFα (an activator of NF-κB), 500 μg/mL poly I:C (TLR3 ligand), 10 μg/mL LPS-B5 (TLR4 ligand) or 10 g/mL Resiquimod (TLR-7/8 ligand). The compounds were used either alone (FIG. 1A grey bars) or combined with 100 nM of plitidepsin (FIG. 1A black bars) for 6 hours, and quantified the luciferase activity under each condition. In the presence of each one of the TLR ligands, plitidepsin clearly inhibited the production of luciferase indicating that transactivation from NF-κB was inhibited in the presence of the drug. Survival was analysed with the MTT assay (FIG. 1B grey bars (activators) and red bars (activators combined with 100 nM of plitidepsin)). No cytotoxic effect was detected.

Figure 2:
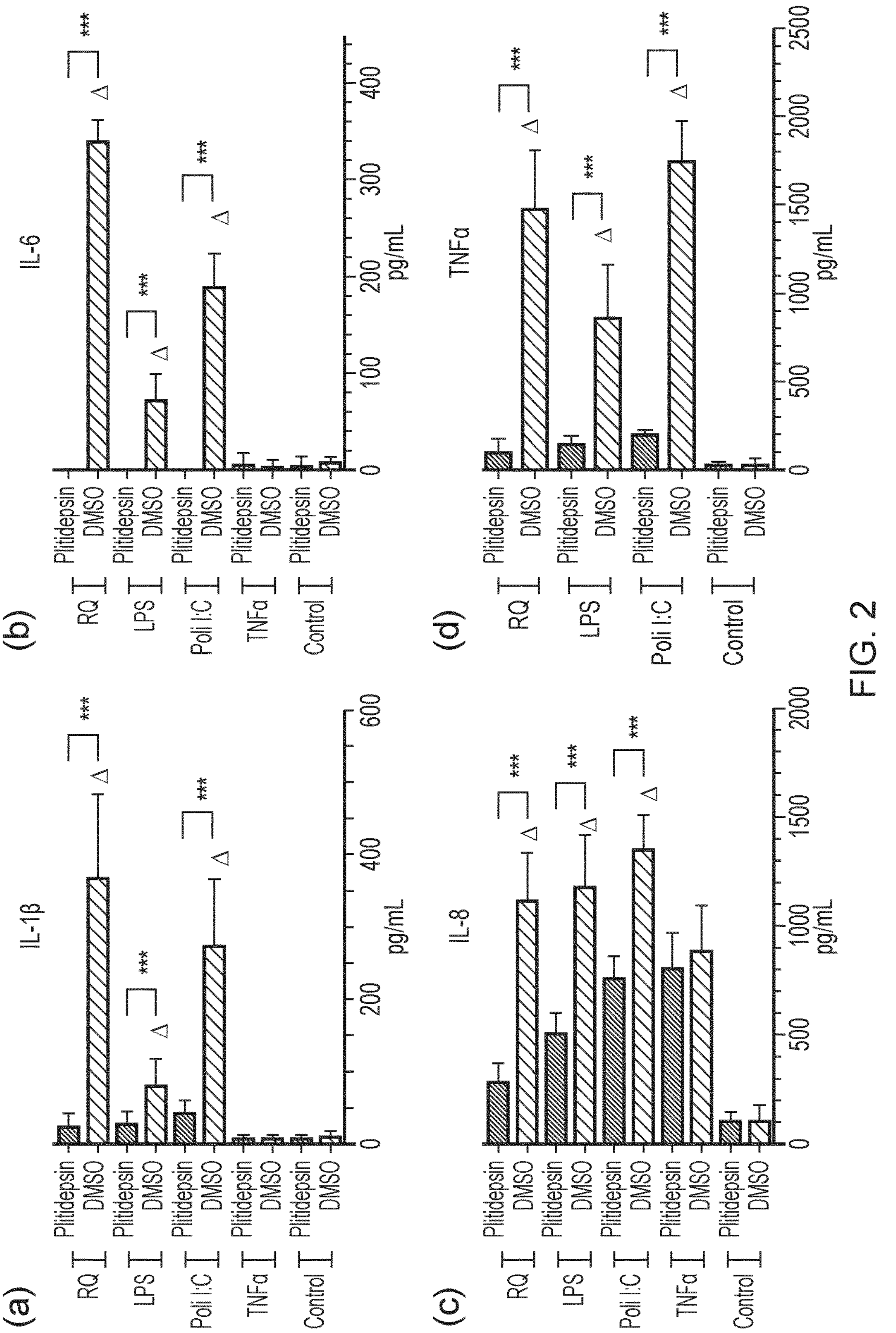
FIG. 2 shows that Plitidepsin negatively regulates TLR-trigged cytokine secretion. NF-κB transactivation in response to the activation of Toll-like receptors leads to increased secretion of the pro-inflammatory cytokines: IL-1 (a), IL-6 (b), IL-8 (c) and TNF-α (d). Cultures were exposed to PLD at 100 nM or DMSO for 6 hours. At 6 hours post-treatment secreted cytokines were analysed by ELISA. TNF-α was used as a positive control. $*p<0.001$; $p<0.01$ FIG. 3A

As shown in FIG. 2, PLD also inhibits in vitro the secretion of the pro-inflammatory cytokines IL-1, IL-6, IL-8 and TNF-alpha in human monocytes.

To investigate whether plitidepsin inhibits the TLR-trigged cytokine secretion, we treated THP-1 cells with 100 ng/mL TNFα (an activator of NF-κB), 500 μg/mL poly I:C (TLR3 ligand), 10 g/mL LPS-B5 (TLR4 ligand) or 10 g/mL Resiquimod (TLR-7/8 ligand). The compounds were used either alone (grey bars) or combined with 100 nM of plitidepsin (red bars) for 6 hours. We compared the variations in cytokine secretion in the cell culture supernatants between the different treatments by ELISA assays. As can be seen in FIG. 2, poly I:C, LPS and Resiquimod induce the secretion of IL-1, IL-6, IL-8 and TNFα. Furthermore, plitidepsin clearly inhibited the production of IL-1, IL-6, IL-8 and TNFα. TNFα failed to increase the secretion of IL-1 and IL-6. It is possible that THP-1 cells need other TNFα exposure times to secret these cytokines.

In the presence of each one of the TLR ligands, plitidepsin clearly inhibited the secretion of pro-inflammatory cytokines IL-1, IL-6, IL-8.

Figure 13A:
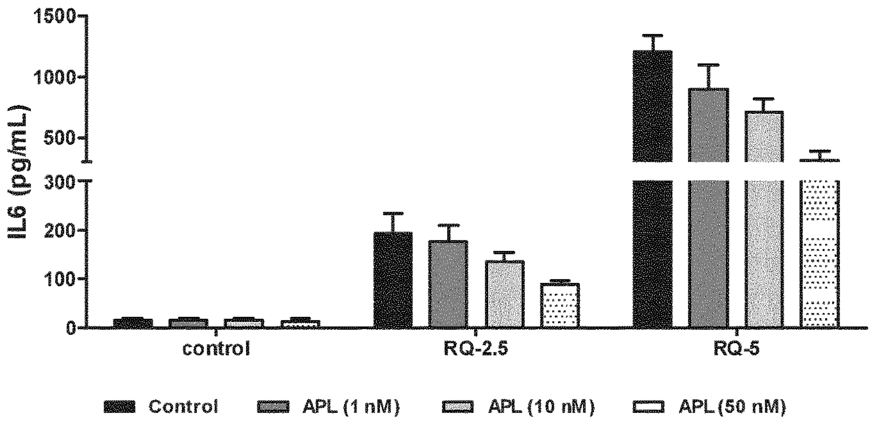
FIG. 13 shows the effect of plitidepsin (APL) pre-treatment at 1 nM, 10 nM and 50 nM on secretion of the pro-inflammatory cytokines IL6 (a), IL8 (b), IL1β (c) and TNF-α (d). (e) shows the effect of 1 nM, 10 nM and 50 nM PLD treatment on cell viability (as a percent of control). At 0 time THP-1 cells were treated with 1 nM, 10 nM or 50 nM APL or DMSO (0.2%) followed by stimulus with Resiquimod at 2.5 or 5 μg/mL at 8 hours. At 24 hours cytokines or cell viability was measured.
Figure 13B:
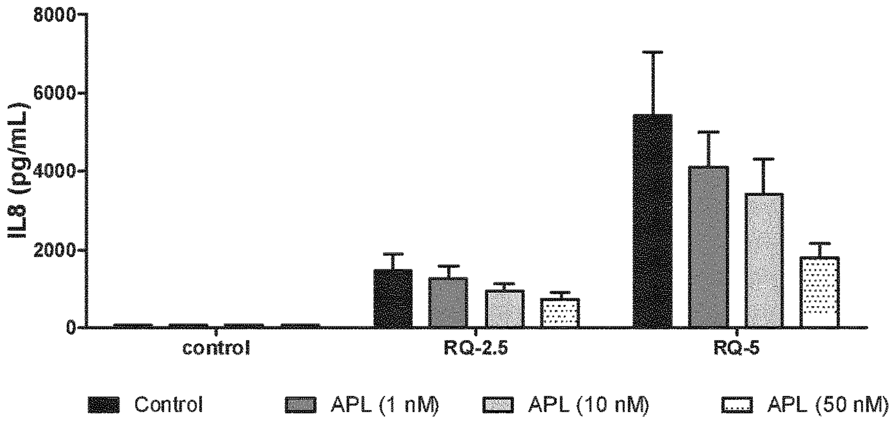
Figure 13C:
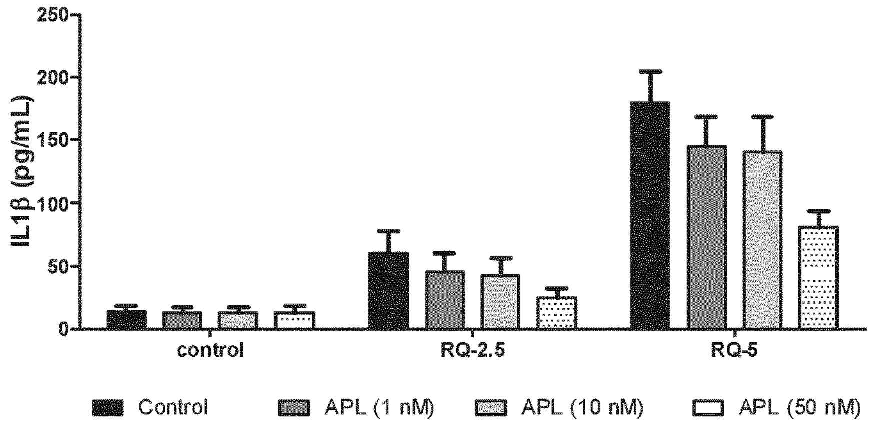
Figure 13D:
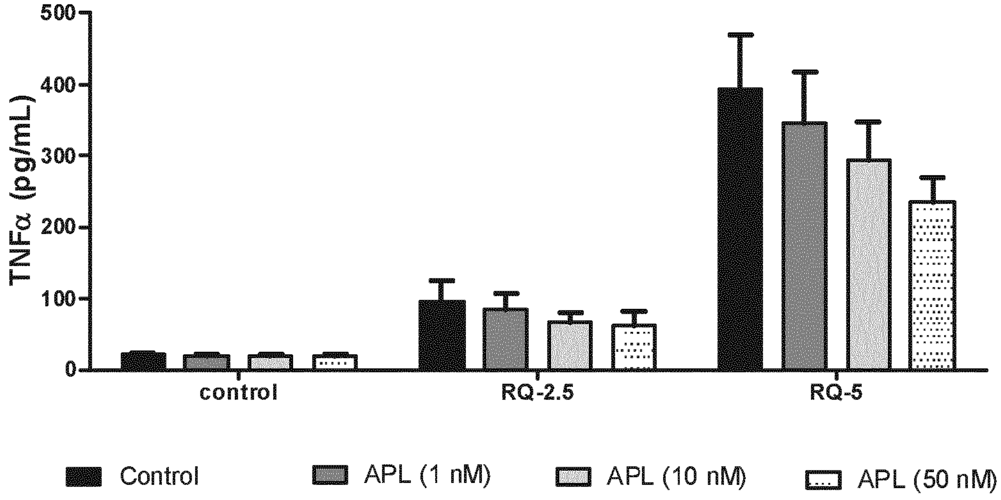
Figure 13E:
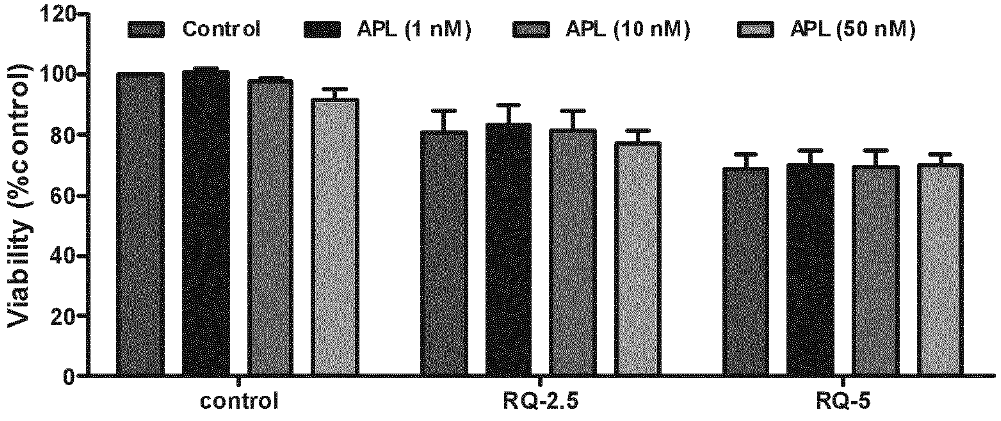
Figure 14A:
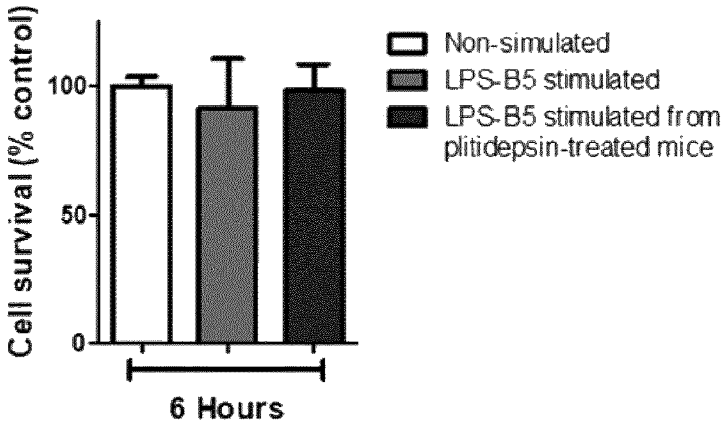
FIG. 14 shows the effect of plitidepsin treatment on the production of the pro-inflammatory cytokines, IL-6 (c), IL-10 (d) and TNF-α (e) mediated by LPS-B5 in $CD45^+$ cells isolated from bronco-alveolar lavages (BALF). (a) shows the percent of $CD45^+$ live cells in control, LPS-B5 and LPS-B5 and PLD treated cells. (b) shows cell survival as a percent of control in LPS-B5 and LPS-B5 and PLD treated cells.
Figure 14B:
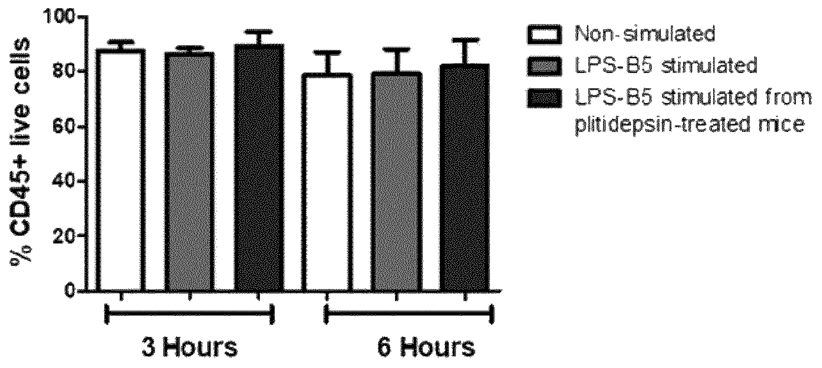
Figure 14C:
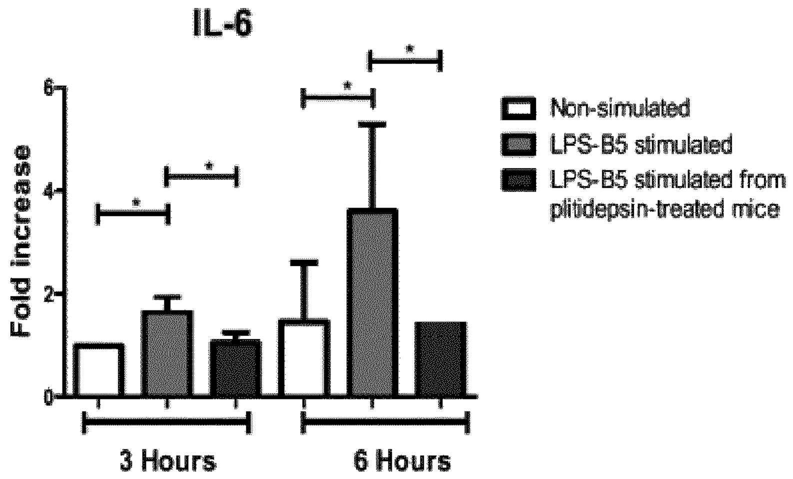
Figure 14D:
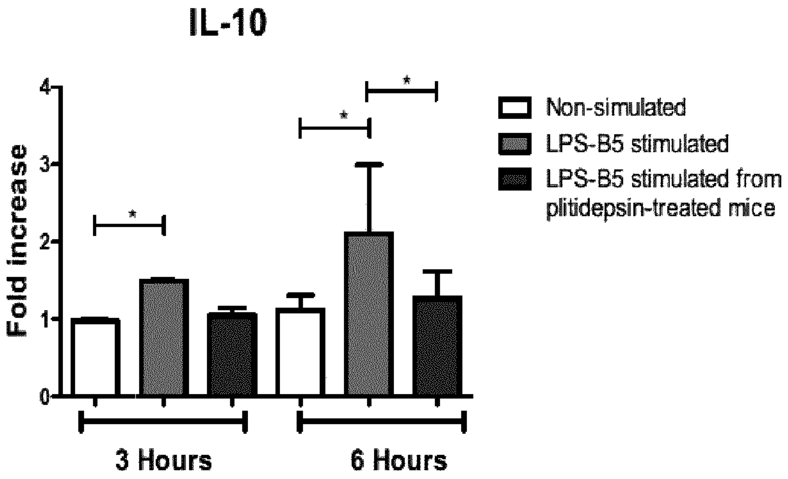
Figure 14E:
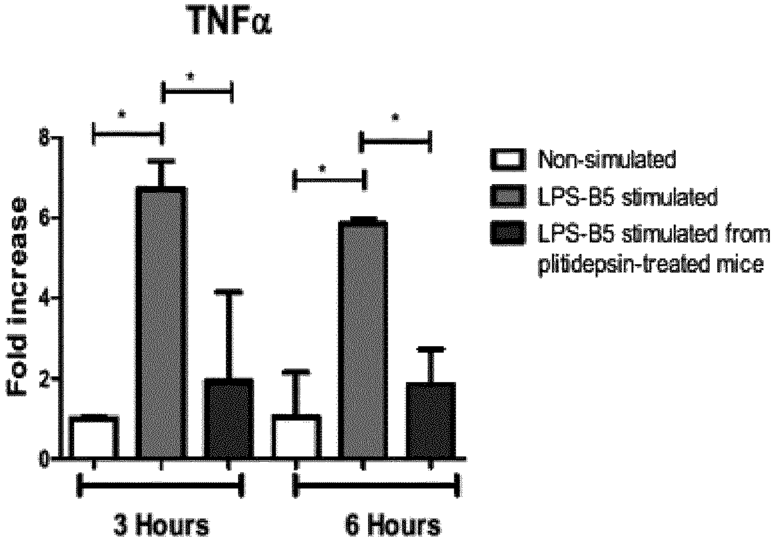

In a further in vitro experiment, the effect of plitidepsin (APL) pre-treatment on THP-1 cells was studied. Using a THP-1 NFκB luc line, 1, 10 or 50 nM of APL or DMSO (0.2%) was added 8 hours before stimulus with Resiquimod (RQ) at 2.5 or 5 μg/mL. RQ is a TLR7/8 agonist and mimics ssRNA. At 24 hours the level of cytokines or cell viability was measured. As shown in FIG. 13, PLD pre-treatment inhibited secretion of the pro-inflammatory cytokines: IL6, IL8, IL1β and TNF-α induced by RQ. Of note, the addition of PLD does not decrease viability over the untreated control at any of the 2 RQ concentrations assayed (FIG. 13*e*). While it is true that RQ itself displays some degree of dose-related toxicity, this effect is not increased by the presence of PLD in the culture and therefore, the changes in cytokine production is unrelated with this RQ induced slight cytotoxicity.

Example 2

Figure 3A:
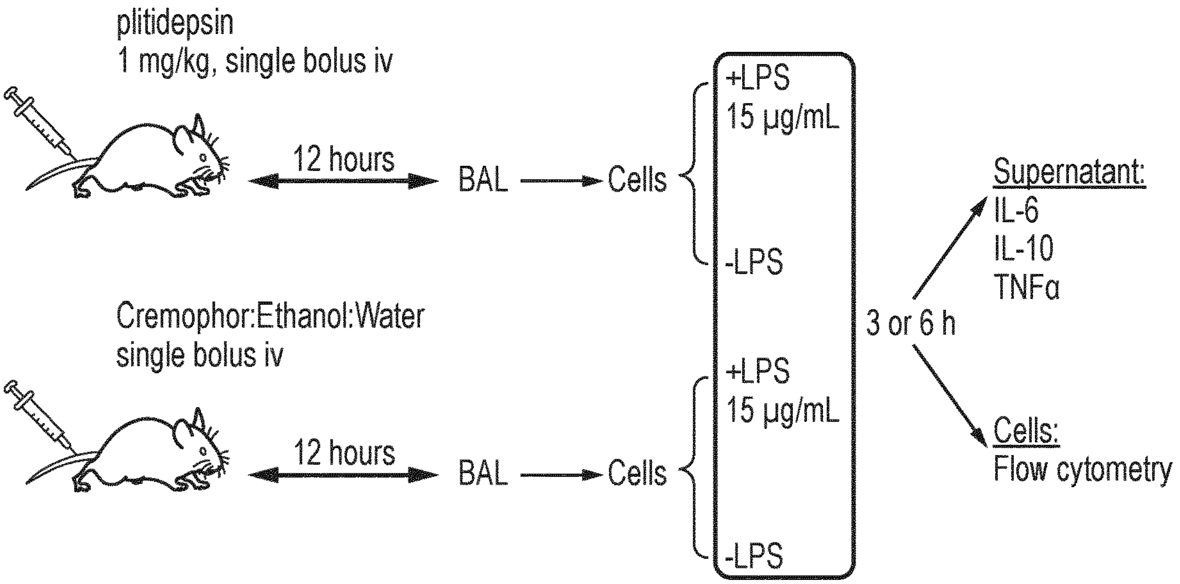
FIG. 3B shows the ex-vivo down-regulation of cytokines IL-6, IL-10 and TNF-α by PLD.
Figure 3B:
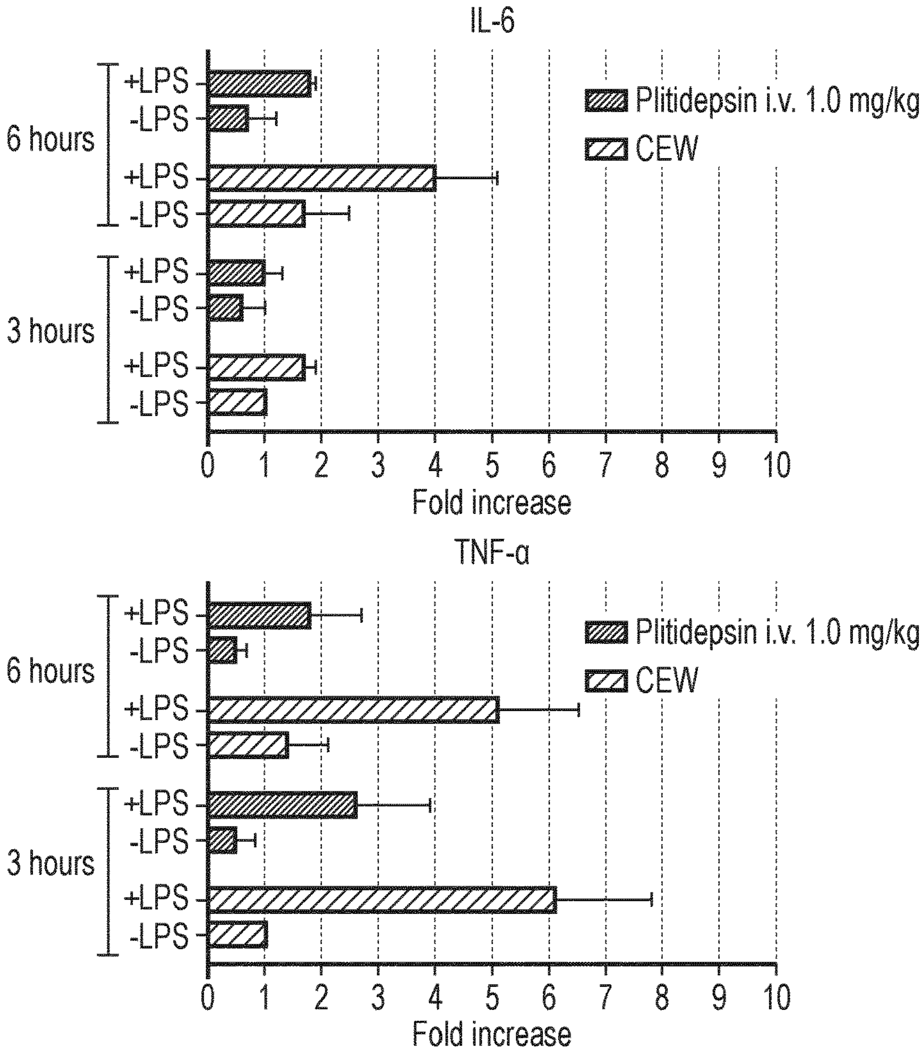
Figure 3B:
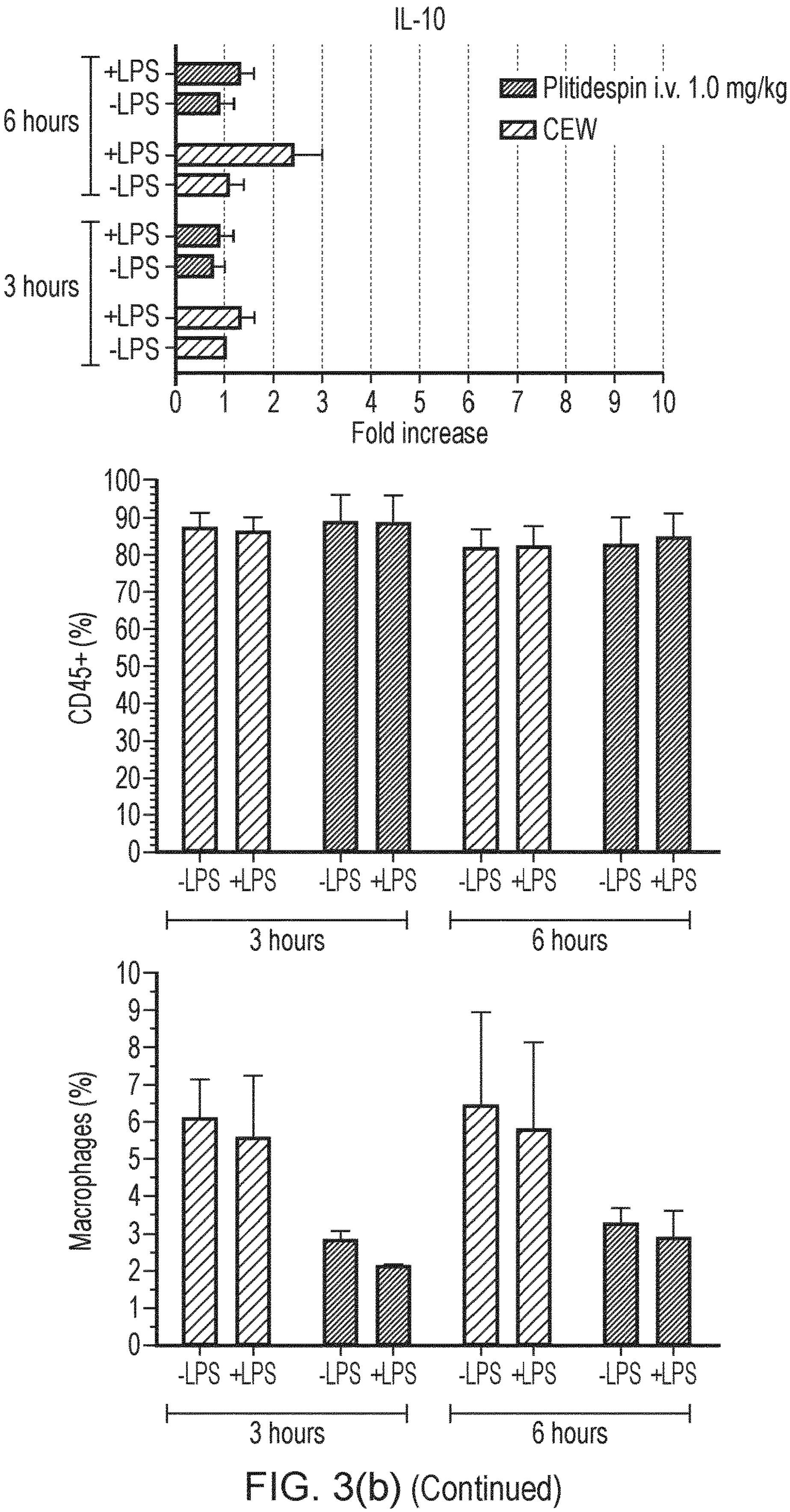

As shown in FIG. 3, PLD inhibits ex-vivo secretion of the pro-inflammatory cytokines, IL-6, IL-8 and TNF-alpha in murine isolated from BAL (Bronchoalveolar lavage).

We checked whether plitidepsin inhibits the LPS-trigged cytokine secretion in alveolar macrophages. To that end mice were injected i.v. with plitidepsin (1 mg/kg) or vehicle and 12 hours after administration bronchoalveolar lavage fluid (BAL) was collected. Cells were plated and treated ex-vivo or not with 15 μg/mL of LPS-B5 for 3 or 6 hours and secreted cytokines were measured. As can be seen LPS induce the secretion of IL-6, IL-10 and TNFα (grey bars). Furthermore, in the animals treated with plitidepsin, the drug clearly inhibited the production of pro-inflammatory cytokines IL-6, and TNF-α induced by LPS (red bars) and led to an overall anti-inflammatory effect.

This is further shown again in FIG. 14. In the animals treated with plitidepsin, plitidepsin was able to significantly reduce the secretion of IL-6, IL-10 and TNFα induced by LPS-B5 at 3 and 6 hours in $CD45^+$ cells isolated from bronco-alveolar lavages. This effect was unrelated to cell viability as shown in FIG. 14(*a*,*b*).

Figure 15:
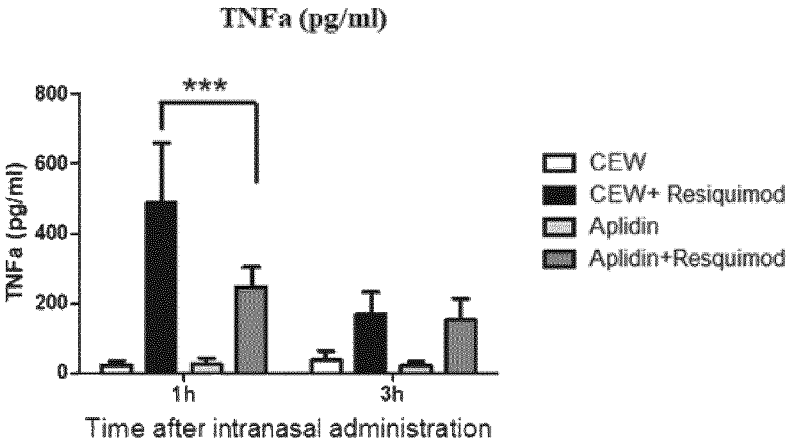
FIG. 15 shows the effect of plitidepsin treatment on the production of the pro-inflammatory cytokines TNF-αt mediated by Resiquimod.

We further checked whether plitidepsin inhibits resiquimod (RQ)-trigged cytokine secretion in BALF. Mice were injected i.v. with plitidepsin (1 mg/kg) or vehicle 1 hour before a 50 μg/mouse intranasal inoculation with resiquimod. At 1 or 3 hours after intranasal administration of RQ bronchoalveolar lavage fluid (BALF) was collected. Cells were plated and secreted cytokines were measured. As can be seen, RQ induces the secretion of TNFα at both 1 and 3 hours following administration. In vivo administration of PLD prevented the increased production of TNFα. As can be seen in FIG. 15, RQ induces the secretion of TNFα at both 1 and 3 hours following administration. In vivo administration of PLD prevented the increased production of TNFα.

Also we checked the effect of plitidepsin on alveolar macrophage recruitment. Viral infection also leads to the activation of macrophages. Activated macrophages are twice the size of resting macrophages and are more "aggressive", having increased levels of lysosomal proteins and a greater ability to phagocytose. Classically activated macrophages also release proteases, neutrophil chemotactic factors, reactive oxygen species and pro-inflammatory cytokines (such as IL-1 beta/IL-1F2, IL-6, and TNF-alpha/TNFSF1A), leading to inflammation and tissue destruction. Bronchoalveolar lavage cells were stained and analyced by flow cytometry.

Plitidepsin decreased the percentage of macrophages presents on bronchoalveolar lavage without cytotoxic effects.

Example 3

Figure 4A:
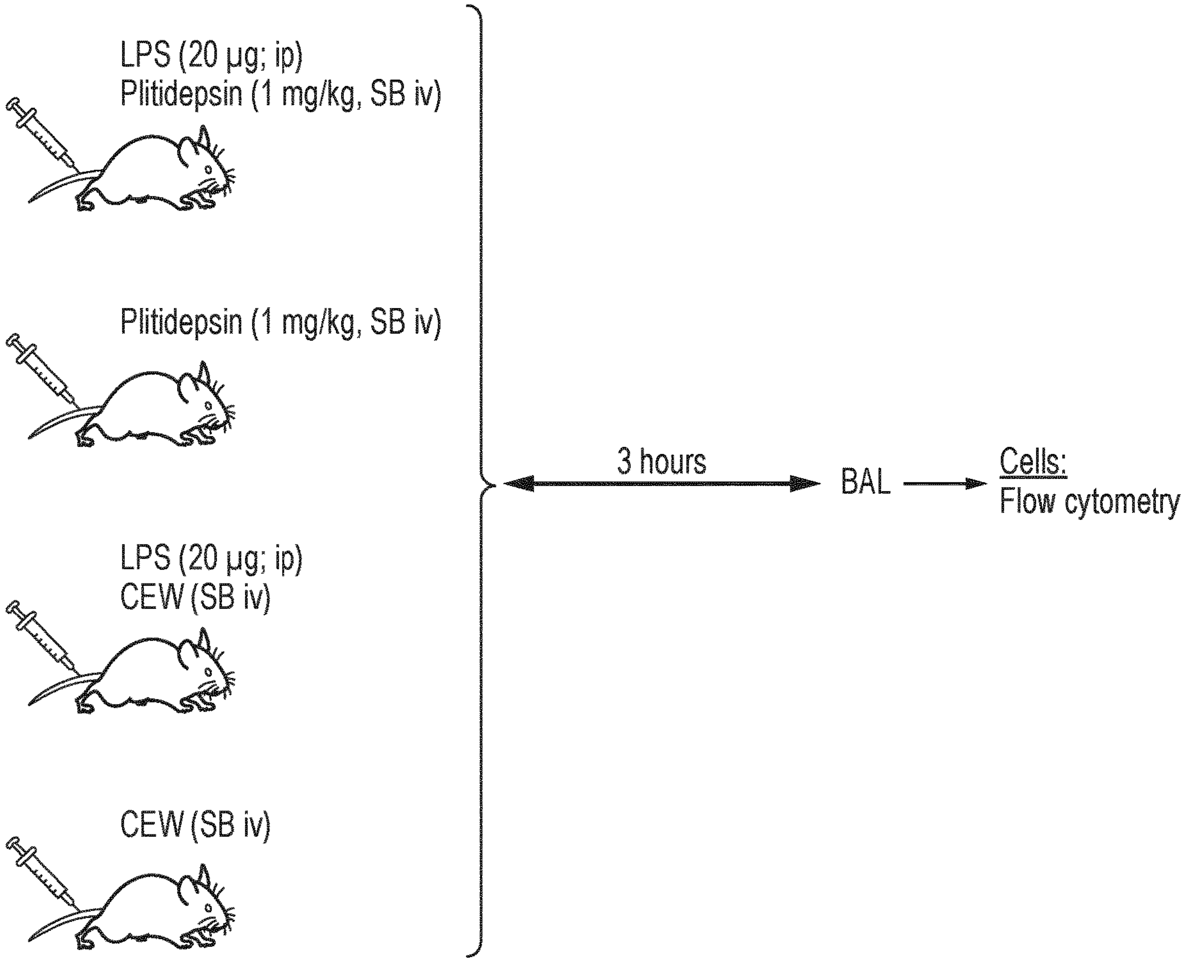
FIG. 4A and FIG. 4B shows a decrease in classically activated macrophages in LPS-challenged mice.

As shown in FIG. 4, after a single iv administration in mice, PLD reduces the number of macrophages in BAL.

Figure 4B:
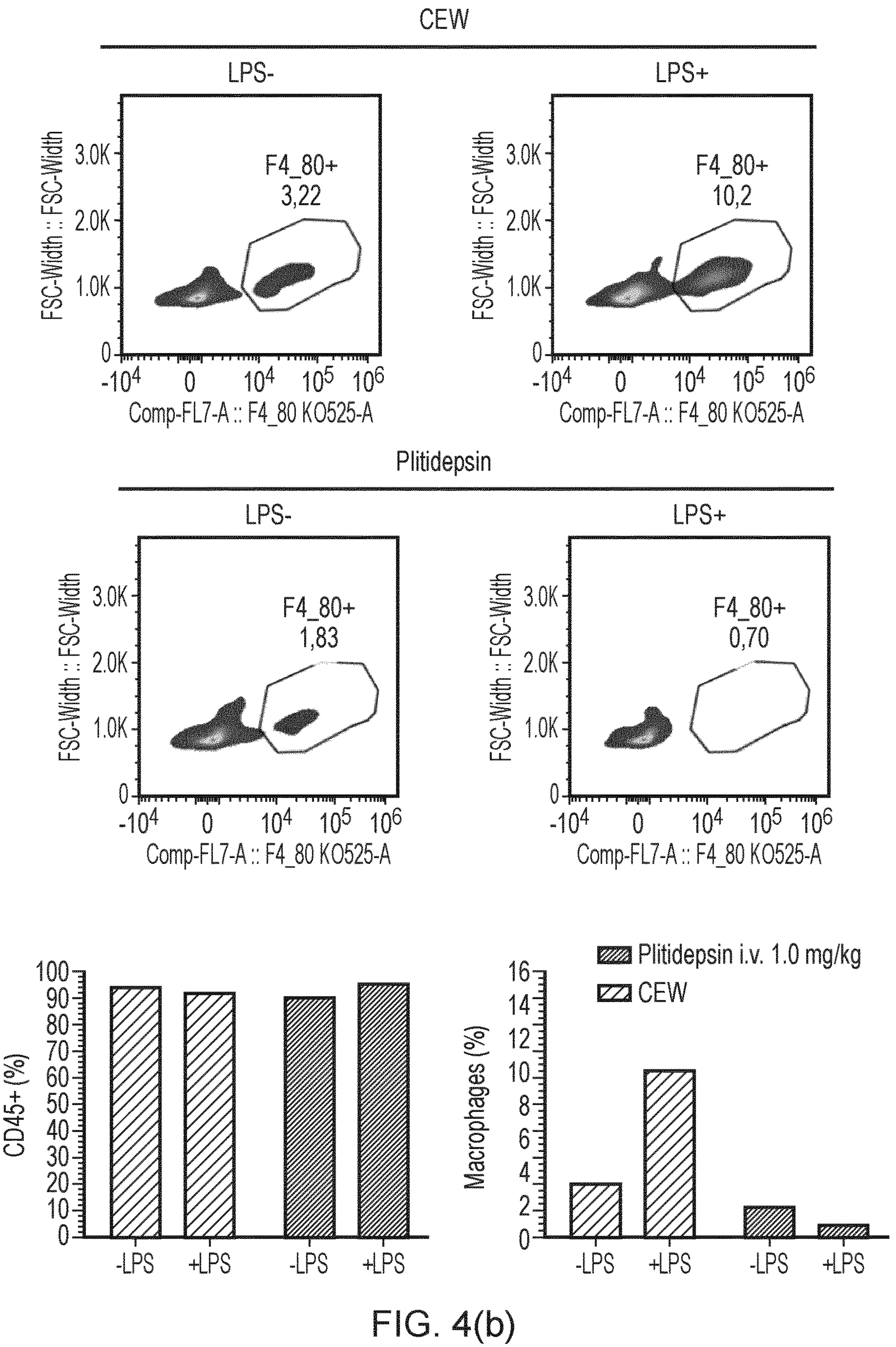

To investigate whether plitidepsin decreases the percentage of alveolar macrophage in animals with acute inflammation, we treated mice with plitidepsin (1 mg/kg) i.v., with LPS (20 μg/kg) i.p. in sterile saline or with plitidepsin (1 mg/kg; i.v.) in combination with LPS (20 μg/kg, i.p.). Three hours later, bronchoalveolar lavages were collected. Bronchoalveolar lavage cells were obtained by centrifugation and analyzed by flow cytometry (FIG. 4*b*). Upper panels show the strategy of analysis of macrophage population present in the samples. Lower right panel show the same result expressed as percentage of cells. Lower left panel show the percentage of CD45+(leucocyte marker) alive cells. As can be seen LPS induce the recruitment of alveolar macrophages. The treatment with Plitidepsin decrease the percentage of macrophages presents on bronchoalveolar lavage without cytotoxic effects.

Example 4

Figure 5A:
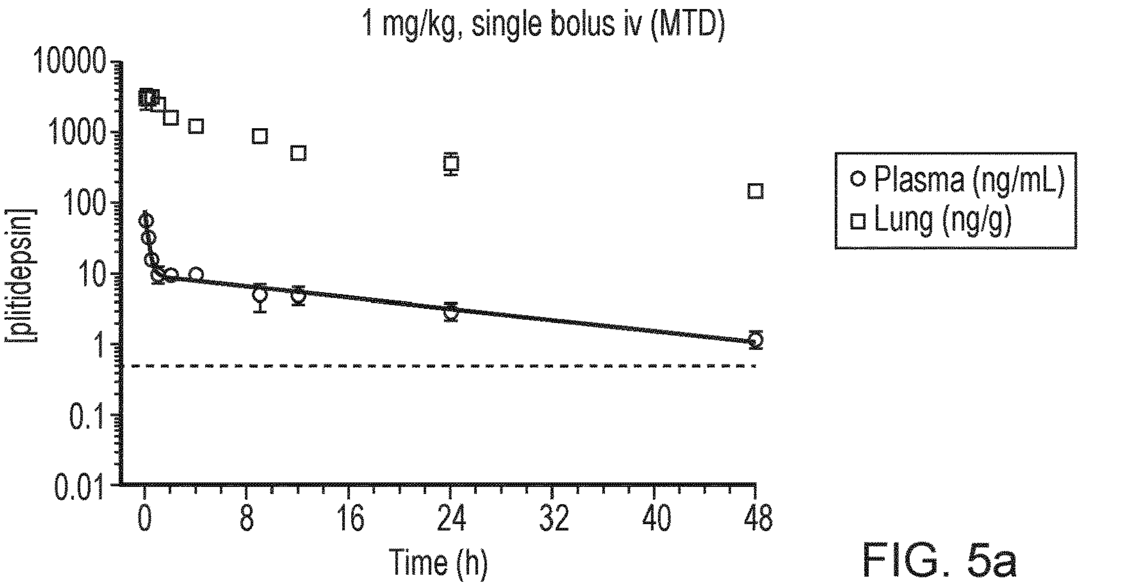
FIG. 5 shows the effects of plitidepsin on alveolar macrophage recruitment in LPS treated mice. Concentration-time curves (mean±SD) of plitidepsin in plasma and lung of mice (a), rats (b) and hamsters (c) after a single intravenous dose at 1.0, 0.2 and 0.2 mg/kg respectively.
Figure 5B:
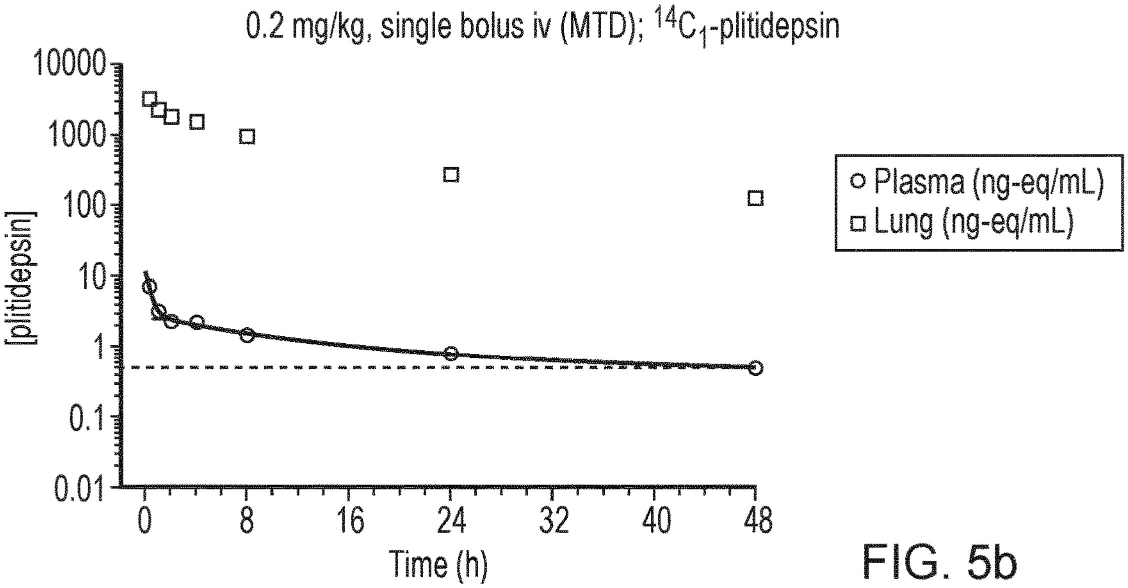
Figure 5C:
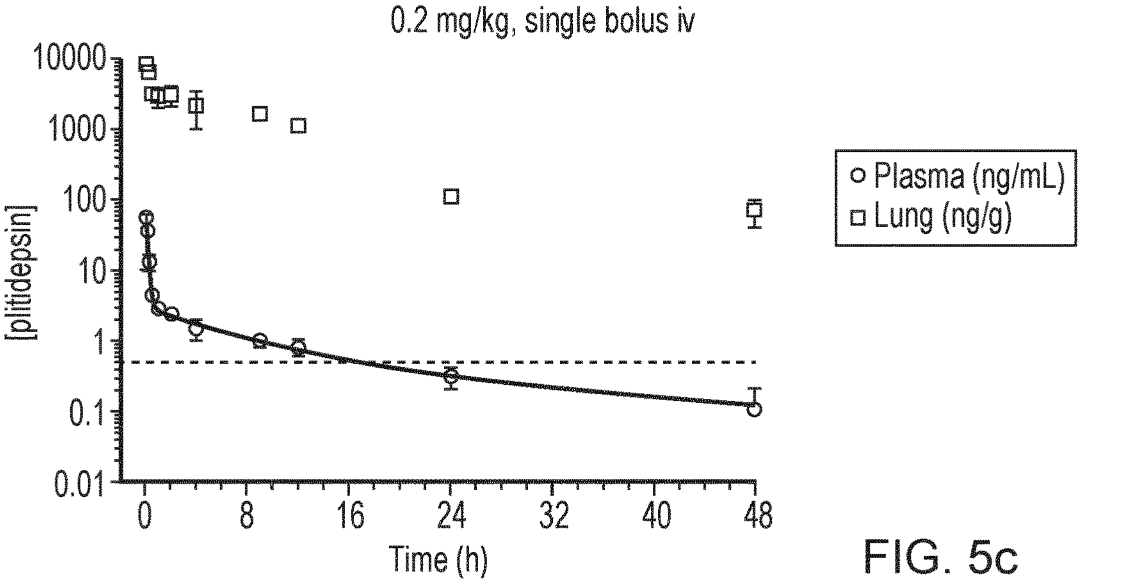

As shown in FIG. 5, PLD is distributed to the lungs in non-clinical species. In addition, similar plasma exposures are achieved in non-clinical the mouse (which is the non-clinical species used in the pharmacological models) and patients.

The concentration of plitidepsin in lungs was consistently higher than that in plasma at any sampling time, with a lung-to-plasma ratio (calculated as ${}^{lung}AUC_{0-\infty}/{}^{plasma}AUC_{0-\infty}$) in mice, rats and hamsters of 133, 460 and 909, respectively, thus confirming the distribution of plitidepsin into the lung.

ELISA Assays for Secreted Cytokines

THP1-NFκB-LUC cell cultures were treated as described above, and the culture medium was sampled at 6 hours post-treatment to assay for secreted cytokines by ELISA. Media samples were stored at 4° C. IL-8, IL-1β, IL-6 and TNF□ protein secretion into culture medium was quantitated using highly specific and sensitive ELISA kits. Human IL-1b, human IL-6, human IL-8 and human TNF OptEIA™ ELISA kits were obtained from BD Biosciences and performed as described by the manufacturer. The data presented are the average of three independent experiments performed in triplicate.

MTT Assay

Cells were seeded in 96 well microtiter plates and allowed to stand for 24 hours at 37° C. and 5% CO2 before treatment described above. After 6 hours of continuous treatment, cellular viability was estimated from conversion of MTT to its coloured reaction product, MTT formazan, which was dissolved to measure its absorbance at 540 nm. Data presented here are representative from a series of at three independent experiments performed in triplicate.

"In Vivo" and "Ex Vivo" Treatments.

Mice were randomized into groups of five animals to receive the treatments. Mice were injected intra venous (i.v.) with plitidepsin (1 mg/kg) and 12 hours after administration were euthanised. Control group received plitidepsin vehicle diluted with saline (Cremophor/Ethanol/Water). Bronchoalveolar lavage fluid (BAL) of each group was collected and centrifugated to obtain bronchoalveolar lavage cells. Cells underwent red blood cell lysis (Roche) and were plated and treated ex-vivo or not with 15 μg/mL of LPS-B5 for 3 or 6 hours. Secreted cytokines were measured using highly specific and sensitive ELISA kits. Mouse IL-6, mouse IL-10 and mouse TNF DuoSet ELISA kits were obtained from R&D Systems and performed as described by the manufacturer. Data presented here are representative from a series of at three independent experiments.

Animal Inflammation Model.

Mice were randomiced into groups of two animals to receive the treatments. Mice were challenged with plitidepsin (1 mg/kg) intra venous (i.v.), with LPS (20 μg/kg) intra peritoneal (i.p.) in sterile saline or with plitidepsin (1 mg/kg; i.v.) in combination with LPS (20 μg/kg, i.p.). The control group received plitidepsin vehicle (Cremophor/Ethanol/Water) diluted with saline. Three hours later, animals were euthanised and bronchoalveolar lavage collected (a total of 1.2 ml, PBS). Bronchoalveolar lavage cells were obtained

TABLE 1

| Species (gender) | Strain | Dose† (mg/kg) | $C_{max}$ (ng/mL) | $AUC_{0-\infty}$ (ng · h/mL) | $t_{1/2}$ (h) | Cl (L/h/kg) | $Vd_{ss}$ (L7kg) |
|---|---|---|---|---|---|---|---|
| Mouse (F) | C57BL6/J | $1.0^a$ | 50.7 | 225.3 | 18.2 | 4.4 | 101.8 |
| Human (M/F) | — | $0.135^b$ | 29.1 | 256.0 | 20-80 | 0.7-0.9 | 29-33 |
| | — | $0.02^c$ | $8.5^d$ | 174.04 | — | — | — |

F, female; M, male.
†Schedule:
Nonclinical species: single intravenous bolus.
Patients: 3-h intravenous infusion.
[a]Maximum Tolerated Dose.
[b]Calculated from the Recommended Dose of 5 mg/m2, 3-h infusion or 9.5 mg/patient.
[c]Equivalent to 1.5 mg/patient, this being a dose used in APLICOV (1-h infusion on days 1, 2 and 3).
[d]Estimated from plitidepsin's population PK model (CPR/2016/01), following 3 daily doses of 1.5 mg/patient.
Human body surface area, 1.9.
Human body weight, 60 kg Materials and Method Transactivation Luciferase Assay.

NF-κB transactivation was assayed using the Bright-Glo™ Luciferase Assay System following the manufacturer's instructions. The NF-κB reporter (Luc)-THP-1 human monocytic, cells stably transfected with NF-κB-Luc plasmid (containing four NF-κB binding sites, a minimal promoter and a luciferase gene), were exposed to 100 ng/mL TNFα (positive control), 500 μg/mL poly (I:C) (Polyinosinic-polycytidylic), 10 μg/mL LPS-B5 (Lipopolysaccharide from *Escherichia coli* 055:B5) or 10 g/mL Resiquimod. The compounds were used either alone or combined with 100 nM plitidepsin for 6 hours. Luminescence was measured in a Perkin-Elmer EnVision reader. A MTT (3-(4,5-dimethylthiazol-2-yl)-2,5-diphenyltetrazolium bromide) cell proliferation assay was simultaneously performed to control the cytotoxicity of the compounds. Cell survival was expressed as percentage of control cell growth. The data presented are the average of three independent experiments performed in triplicate.

by centrifugation and analyzed by flow cytometry. Data presented here are representative from a series of at three independent experiments.

In another inflammation model, mice were randomized into groups of two animals to receive the treatments. Mice were challenged with plitidepsin (1 mg/kg) intra venous (i.v.) followed by Resiquimod (50 μg/mouse, intranasal) 1 hour latter. The control group received plitidepsin vehicle (Cremophor/Ethanol/Water) diluted with saline. One and 3 hours later, animals were euthanized, bronchoalveolar lavage collected (a total of 1.2 ml, PBS) and then, TNFα quantified by ELISA kits. Data presented here are representative from a series of at three independent experiments.

Analysis of Macrophages by Flow Cytometry.

Bronchoalveolar lavage cells were stained with anti-F4/80-BV510, CD45-APC700, CD11b-BV650, CD11c-APC-Fire, CD24-PC7 and Ly6C-BV605 monoclonal antibodies (Biolegend) and a LIVE/DEAD™ Fixable Green Dead Cell Stain Kit, for 488 nm excitation (Thermofisher). Macrophages (F4/80+) were gated on alive immune cells (CD45+ LIVE/DEAD dye−), while alveolar macrophages (F4/80+ CD24−) were specifically gated on CD11c+CD11b− population from alive immune cells. Isotype controls and compensation beads were used to set compensations and gating strategies.

Example 5

The aim here was to evaluate in vivo the effects of plitidepsin in the treatment of severe pneumonia caused by the mouse-adapted A/H1N1 influenza virus infection (A/Puerto Rico/8/34), and also on viral titre levels.

Experimental set-up: To achieve this objective we employed an in vivo model of viral pathogenesis based on the administration of high-dose of PR8 influenza virus (2×105 pfu), which generated a severe infection in the lungs. We then evaluated the therapeutic effect of plitidepsin on severe influenza virus infection in mice. Female mice at the age of 9 weeks were anesthetized by intraperitoneal injection of ketamine-xylazine solution and infection was performed by intranasal administration of virus solution PBS into 20 ul per nares.

Mice that were receiving the treatment were injected subcutaneously with 0.3 mg/kg or 0.15 mg/kg of plitidepsin. Subsequently, survival and body weight loss was monitored until day 3 p.i. No death mice or mice with a weight loss of more than 30% of the starting body weight was recorded during the time of the treatment.

Figure 6:
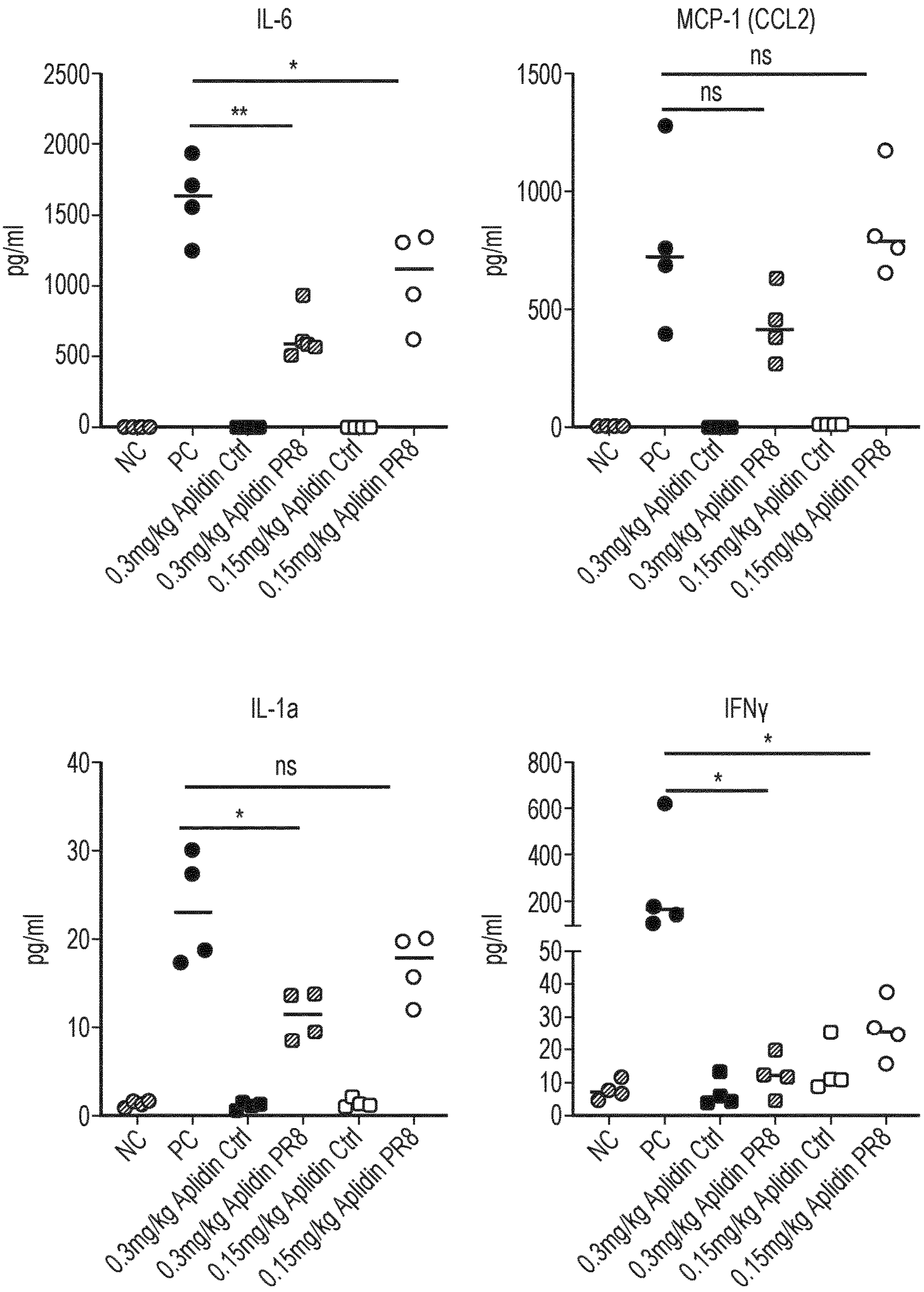
FIG. 6 shows the inflammatory profile in the BALF of mice infected with influenza virus with (PR8) or without (PC) treatment with PLD.
Figure 6:
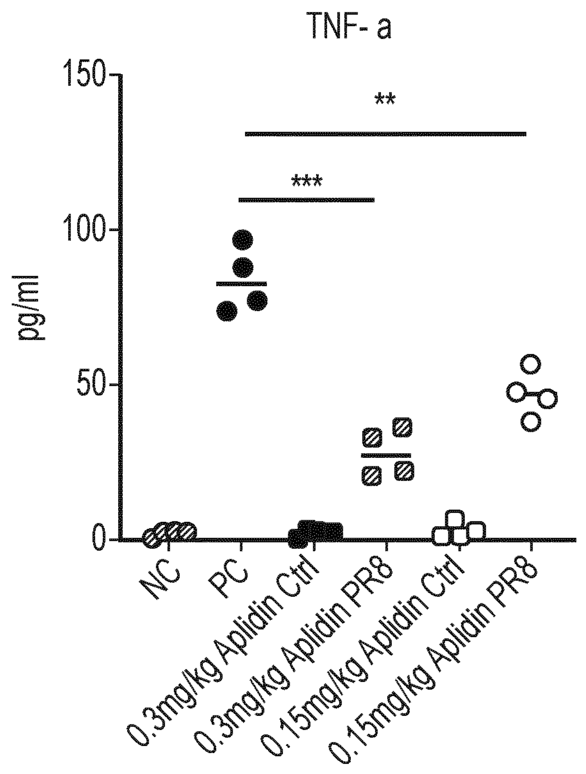

The control of influenza infection in the airways is mediated by enhanced inflammation in the bronchoalveolar lavage fluid (BALF). FIG. 6 shows the inflammatory profile in the BALF of infected mice with or without treatment with plitidepsin. Among the major pro-inflammatory cytokines, plitidepsin strongly reduced the levels of IL-6, CCL2, IL-1α, IFN-γ and TNF-α. Mice that were receiving only half-dose of the drug were less protected and showed an intermediated phenotype.

Figure 7:
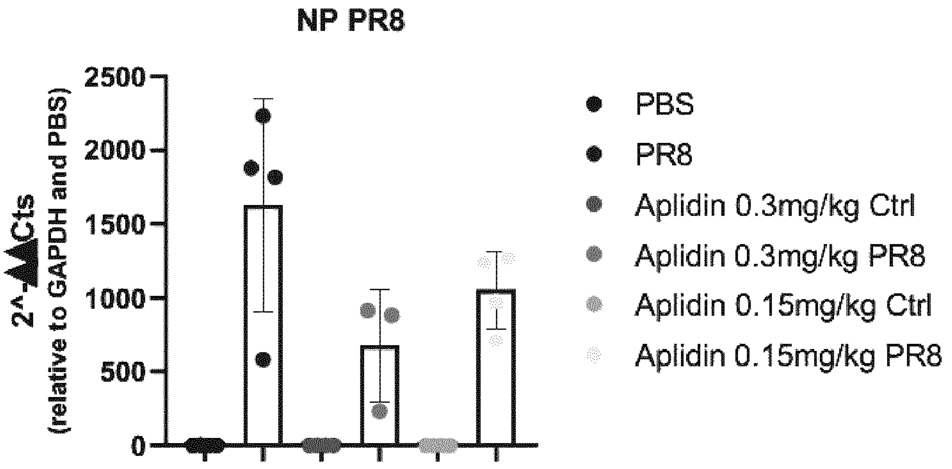
FIG. 7 shows the titre of influenza virus in the lung of mice with or without treatment with PLD. The antiviral activity of PLD was quantified by qPCR measuring the mRNA level of viral NP (NP-PR8).

The viral titer in the lungs was also assessed. As shown in FIG. 7, plitidepsin reduced the viral titre in the lungs at both 0.3 mg/kg and 0.15 mg/kg.

Figure 8:
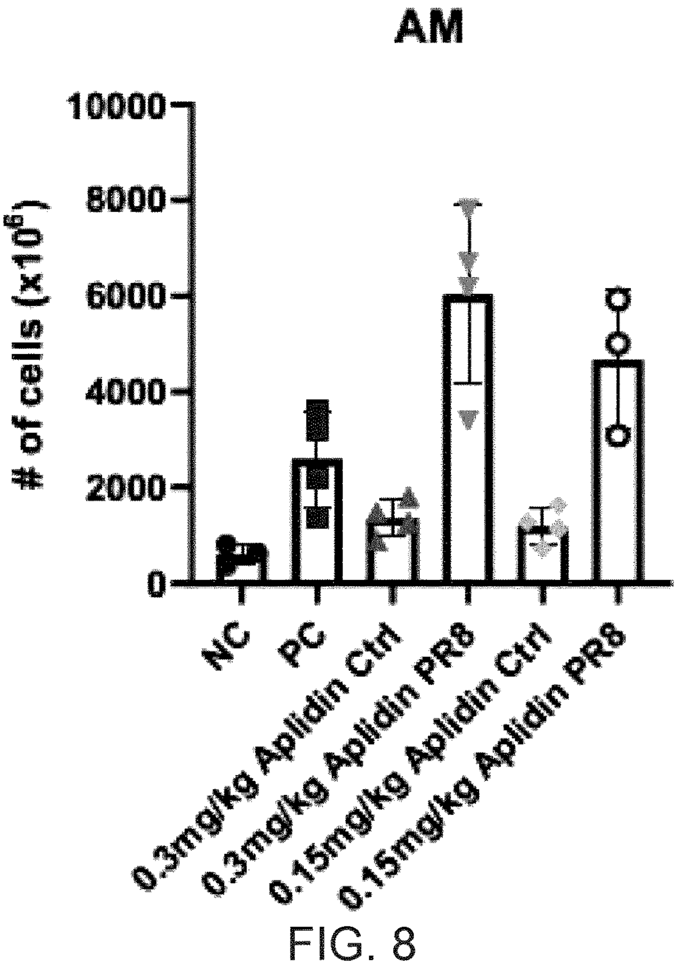
FIG. 8 shows a quantitative measurement of the level of immune cell infiltration, particularly AMs (alveolar macrophages) in the BALF of influenza infected mice treated with (PR8) or without (PC) PLD.

The BALF cellular composition is defined as a marker of lung immune response viral infection. Quantitative measurement of infiltrating cells in correlation to inflammatory cytokine levels was assessed in influenza infected mice. Treatment with plitidepsin did not reduce the total cellular composition of the BALF ($CD45^{+}\times10^{6}$). As shown in FIG. 8 we also found an increase in alveolar macrophage (AM) infiltration suggesting that AMs contribute to viral clearance.

All together, these results confirmed that three subsequent administrations of (total dose of 0.9 mg/kg) of plitidepsin in influenza infected mice can positively reduce inflammation, as shown by the reduction of the early pro-inflammatory cytokines by the treatment. In addition, we detected an increase in alveolar macrophage absolute numbers, which could suggest that AMs play a critical role in viral spread and protection. We also saw a diminished viral titer in the lung of plitidepsin high-dose treated mice.

Example 6

In this example, the antiviral activity of plitidepsin on the spread of West Nile virus in cell culture was studied.

(a) Recombinant Virus WNV-GFP (Lineage 2; Molecular Clone WN956) in Human Hepatoma Cells (Huh7) and African Green Monkey Kidney Cells (Vero-E6).

In order to determine the antiviral potential of plitidepsin against WNV-GFP, target cell lines Vero-E6 and Huh7 were inoculated with an infectious virus stock dilution in the presence of increasing concentrations of plitidepsin, starting at 2.3 pM or 2.5 pg/ml and using 4.5 μM or 5 μg/ml as the highest concentration. Infection efficiency was evaluated at 48 hours, after the virus has spread to a substantial fraction of the target cells in vehicle-treated cultures.

Relative infection efficiency was assessed by automated fluorescence microscopy in the green channel and overall cell biomass/well was estimated by nuclear staining with DAPI in the blue channel, as a preliminary assessment of the compound effective doses as well as overall compound cytotoxicity.

Figure 9:
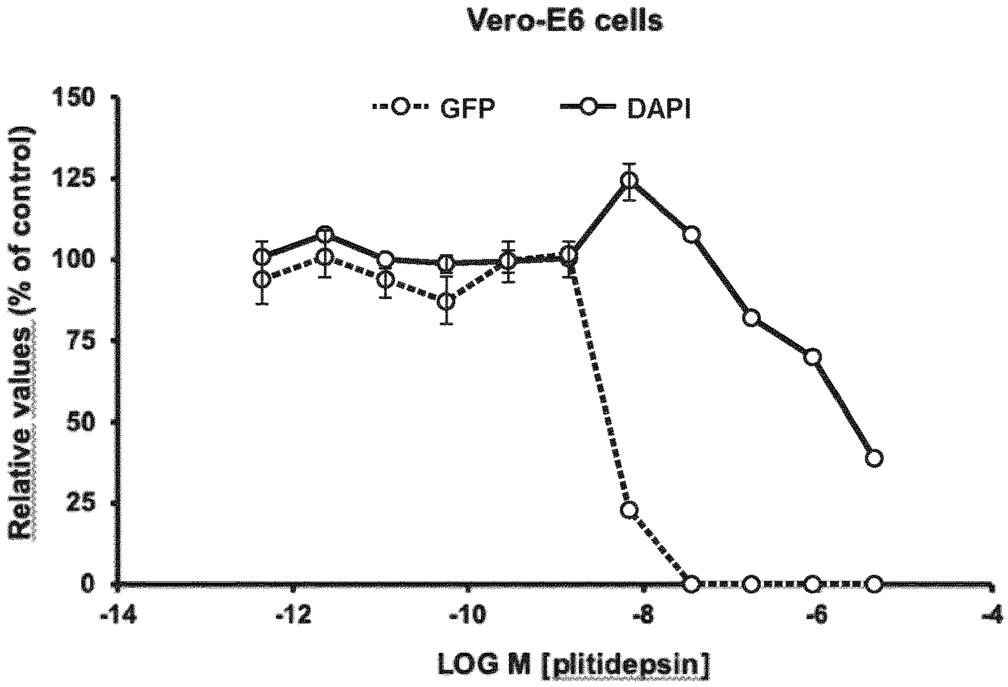
FIG. 9 shows WNV-GFP infection efficiency in VeroE6 cells. Plitidepsin dose-response curves for infection efficiency (GFP; green line) and cell biomass (DAPI; blue line). Data are shown as average and SEM of two independent experiments performed with four biological replicates (n=8).

As shown in FIG. 9, WNV-GFP infection efficiency rapidly decreased at doses around 5 nM in VeroE6 cells, reaching background fluorescence levels at 36 nM and above. The cell number remained unchanged up to 36 nM, but significantly decreased at higher concentrations (180 nM; $p<0.05$), suggesting that plitidepsin interferes with cell duplication capacity at concentrations above 36 nM. The estimated EC50 value for plitidepsin in VeroE6 cells is 4.9 nM and the EC90 is 9.5 nM. Based on the cell biomass the CC50 value is 2330 nM. Thus, the therapeutic index, expressed as the ratio CC50/EC50 in VeroE6 cells is 475.

Figure 10:
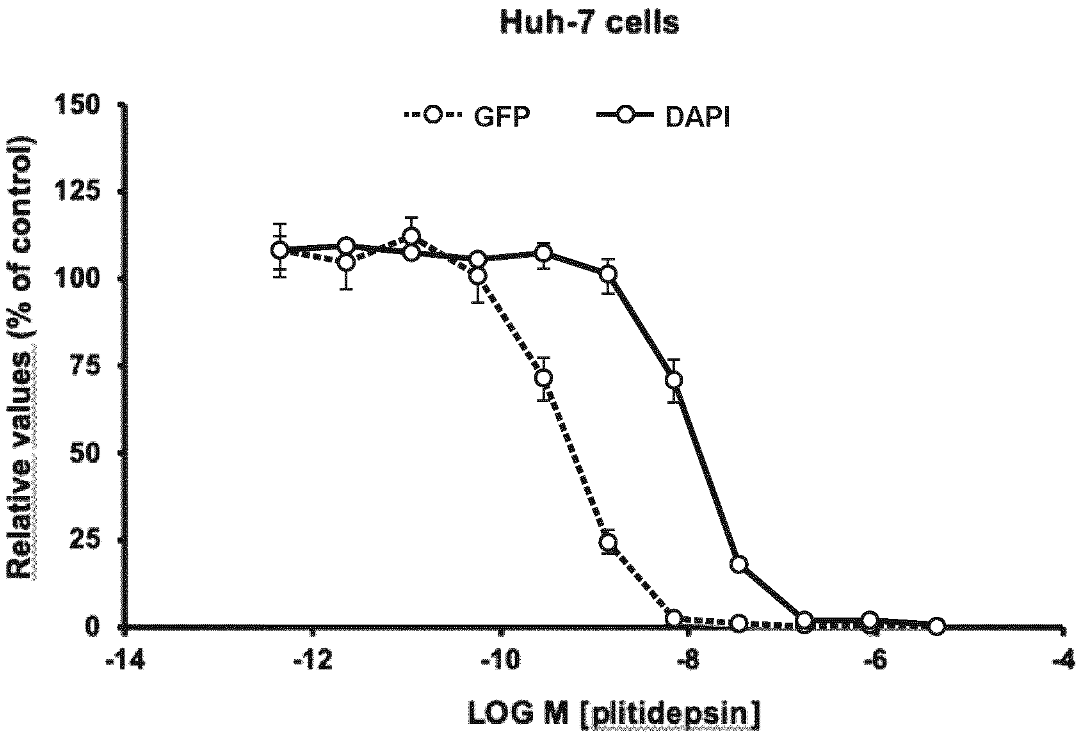
FIG. 10 shows WNV-GFP infection efficiency in Huh-7 cells. Plitidepsin dose-response curves for infection efficiency (GFP; green line) and cell biomass (DAPI; blue line). Data are shown as average and SEM of two independent experiments performed with four biological replicates (n=8).

In Huh7 cells, as shown in FIG. 10, there is a dose-dependent reduction in infection efficiency with EC50 and EC90 values of 0.665 and 3.86 nM respectively. This reduction is associated with a parallel loss of cell biomass in the well, which is statistically significant at 7.2 nM ($p<0.05$) with a CC50 value of 14.7 and a therapeutic index of 22.

The above data shows that plitidepsin interferes with WNV-GFP propagation in cell culture infection models in both Vero-E6 and Huh-7 cells. In one example, antiviral activity in the absence of measurable interference with cell viability may be observed at 1.5 nM ($p<0.05$) in Huh-7 cells and 7.2 nM ($p<0.05$) in Vero-E6 cells.

(b) Recombinant Virus with Wild-Type WNV-NY99 Genome (Lineage 1; Molecular Clone NY99) in Huh7 Human Hepatoma Cells and African Green Monkey Kidney Cells (Vero-E6).

In this example, the impact of plitidepsin on WNV-NY99 propagation using viral RNA load as readout of the infection efficiency was assessed. Vero-E6 or Huh-7 cells were inoculated (MOI 0.01) with a recombinant virus based on the NY99 WNV strain. Infection was performed in the presence of the vehicle or a dose range of plitidepsin displaying bioactivity in the WNV-GFP model (45, 15, 5, 1.5 nM; see above). Inoculated cells were incubated for 48 hours, time at which samples of the supernatants were processed to determine infection efficiency by extracellular infectivity titration. In addition, total RNA was extracted from control and plitidepsin-treated cells to determine viral RNA load and independently assess overall viral infection efficiency.

Figure 11A:
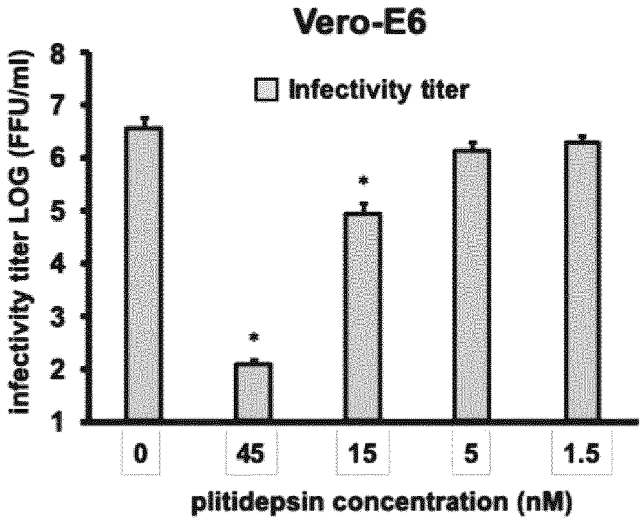
FIG. 11 shows the impact of plitidepsin on WNV extracellular infectivity titers. Vero-E6 (a) or Huh-7 cells (b) were inoculated with WNV/NY99 at MOI 0.01. Forty-eight hours later, cell supernatants were collected to determine the extracellular infectivity titers by endpoint dilution and immunofluorescence microscopy. Data are expressed in infectious units per volume of supernatant (focus forming units (FFU)/ml) in logarithmic scale and are shown as average and SEM (N=4). Statistical significance was tested using one-way ANOVA and a Dunnet's post hoc test ($*p<0.05$).
Figure 11B:
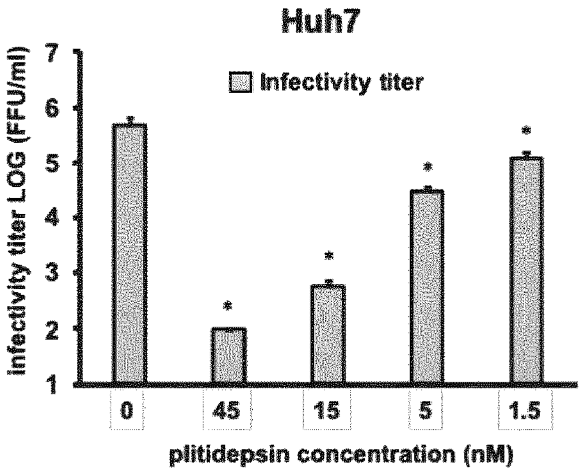

Extracellular infectivity titers show that the presence of plitidepsin strongly interfered with WNV propagation as shown in FIG. 11, with reductions >3 orders of magnitude at 45 nM in VeroE6 and Huh-7 cells. This phenomenon is dose-dependent in both cell lines.

Figure 12A:
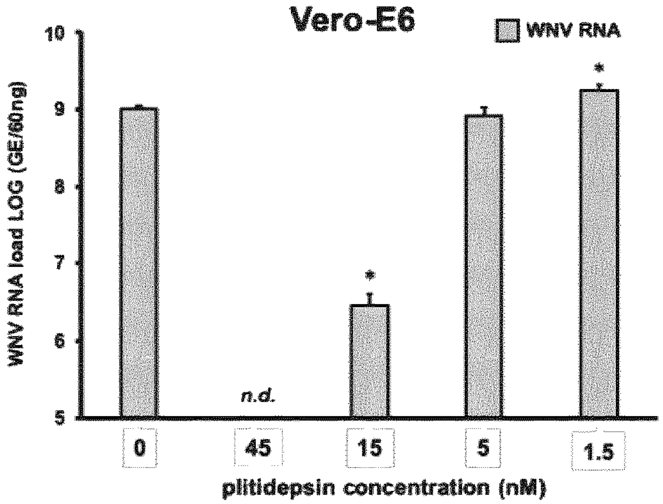
FIG. 12 shows the impact of plitidepsin on intracellular WNV RNA levels. Vero-E6 (a) or Huh-7 (b) cells were inoculated with WNV/NY99 at MOI 0.01. Forty-eight hours later, total cellular RNA was subjected to RT-qPCR. Data are expressed as number of genome copies/60 ng of total RNA normalized in logarithmic scale using 28S RNA as housekeeping gene and are shown as average and SEM (N=4). Statistical significance was tested using one-way ANOVA and a Dunnet's post hoc test (*$p<0.05$). n.d., not detected (<1000 copies/reaction).
Figure 12B:
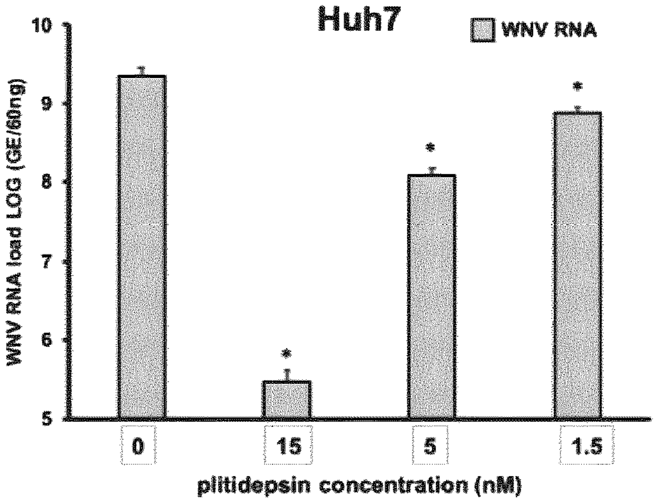

Intracellular WNV RNA load was determined by RT-qPCR in control and plitidepsin-treated cells. Remarkably, as shown in FIG. 12, no RNA could be recovered from Huh-7 cells treated with 45 nM plitidepsin. Nevertheless, viral RNA load was determined in the rest of the sample groups in both cell lines. In agreement with the trend exhibited by the extracellular infectivity titers, viral RNA load significantly decreased in a dose-dependent manner at 15 and 45 nM in Vero-E6 cells, while the viral load at 5 and 1.5 nM were not distinguishable from those in the control (FIG. 12). Similarly, Huh-7 showed a marked reduction in viral load at 15 nM, magnitude of which declined in a dose-dependent manner.

The WNV infection propagation efficiency data suggest that plitidepsin interferes with viral replication at doses above 5 nM in both Vero-E6 and Huh-7 cells, although some degree of interference could be observed at lower concentrations in Huh-7 cells. The results measuring overall propagation efficiency using functional (infectivity) as well as molecular (RT-qPCR) approaches confirm that plitidepsin reduces virus propagation efficiency in the expected range of concentrations based on the data obtained with WNV-GFP.

In summary, supplementation of the cell culture medium with increasing doses of plitidepsin resulted in strong reduction in WNV propagation efficiency in the two infection (WNV-GFP and WNV/NY99) models and in both Vero-E6 and Huh-7 cells.

(c) Methods

Compound preparation: Pre-weighted solid was diluted to a final 1 mg/ml solution in dimethylsulfoxyde (DMSO) and aliquoted at −20° C. until further use. Cell culture: Subconfluent Vero-E6 cells and Huh-7 cell cultures were maintained in complete media [(DMEM supplemented with 10 mM HEPES, 1× non-essential amino acids (Gibco), 100 U/mL penicillin-streptomycin (Gibco) and 10% Fetal Bovine Serum (heat-inactivated at 56° C. for 30 min)].

Viruses: WNV (NY99) and WNV-GFP recombinant viruses were rescued from cloned cDNA as previously described. Stock infectivity titers were determined by plaque assay on Vero-E6 cells as previously described.

Part 1: WNV-GFP Model

Infection experiments: Cells were seeded onto 96-well plates (2×104 cells/well). The day after, serial 5-fold dilutions of plitidepsin were prepared in 2% FCS-containing complete media to achieve the indicated final concentrations. WNV-GFP stock was diluted in complete media containing 2% FCS to achieve the required multiplicity of infection (MOI 0.01). Compound and virus dilutions were mixed 1:1 and added onto the target cells. Cells were incubated for 48 hours at 37° C.; 5% CO2 and 95% humidity.

Cells were fixed by addition of a 5× formaldehyde solution to achieve a 4% final concentration for 30 mins at room temperature. Cells were washed with PBS and stained with DAPI (4',6-diamidino-2-phenylindole) following manufacturer's recommendations. Relative infection efficiency was estimated by image analysis in an automated microscopy device (Tecan Spark Cyto). Uninfected cells and vehicle-treated controls were included in each plate.

Part 2: WNV (NY99) Model

Cells were seeded onto a 24-well plate using $1.2\times10^5$ cells/well. The day after, cells were inoculated with a WNV/NY99 stock to achieve a multiplicity of infection of 0.01 (MOI 0.01) and the indicated plitidepsin concentration in a final volume of 1 ml. Cultures were maintained at 37° C. for 48 hours, time at which supernatants were collected and preserved at −80° C. Total RNA was collected from cells by adding Trizol™ reagent directly to the cells and following the manufacturer's instructions.

Infectivity titration: infectivity titers were determined using endpoint dilution and immunofluorescence microscopy using a monoclonal antibody against Flavivirus E protein (4G2; ATCC® HB-112™). Briefly, Huh-7 cells were inoculated with supernatant dilutions in a 96-well format. Forty-eight hours post infection, cells were fixed for 30 minutes at room temperature with a 4% formaldehyde solution in PBS, washed twice with PBS and incubated with binding buffer (0.3% Triton X100, 3% BSA in PBS) for 1 hour. Primary antibody was diluted in binding buffer and incubated with the cells for 1-hour, time after which the cells were washed with PBS and subsequently incubated with a 1:500 dilution of a goat anti-mouse conjugated to Alexa 488 (ThermoFisher). DAPI (4',6-diamidino-2-phenylindole; ThermoFisher) was used as nucleus staining reagent to evaluate cell number. Cells were washed with PBS and infection foci number was determined under a fluorescence microscope.

Reverse-transcription and qPCR: 60 ng of total cellular RNA were subjected to RT-qPCR using NZYSpeedy One-Step qPCR probe master mix, using manufacturer's recommendations and the primers.

Statistical Analysis: Means and SEM were calculated using Excel. Means were compared using one-way ANOVA and a Dunnet's post-hoc analysis (2-tails; alpha=0.05) using IBM-SPSS

Example 7

Figure 16:
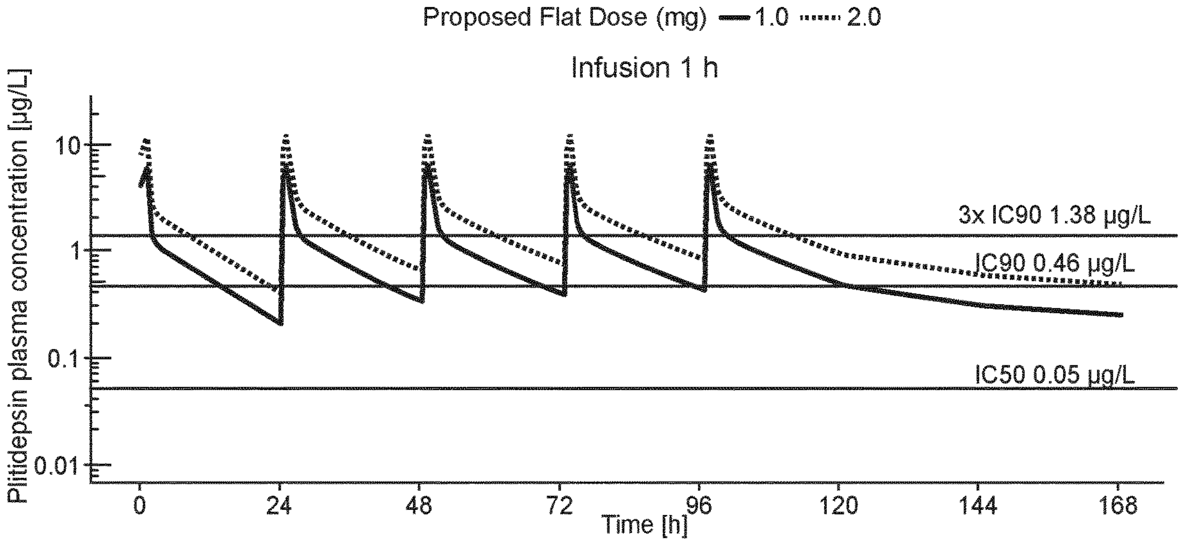
FIGS. 16 and 17 show total plasma concentration profiles vs. time predicted for dosing schedules and administration according to the present invention.
Figure 17:
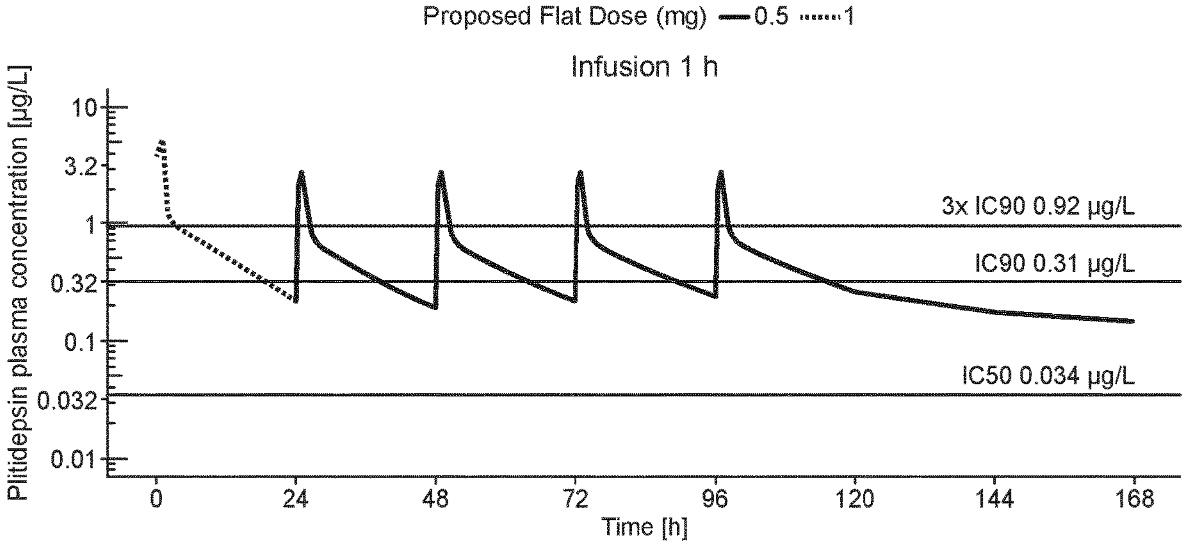

FIG. 16 illustrates the simulation of the total plasma plitidepsin concentration profiles vs. time after a daily dose (D1-D5) of 1.0 mg and 2.0 mg. The horizontal black lines represent the total plasma concentrations associated with the concentrations in lung equivalent to exemplary IC50, IC90 and 3×IC90 in vitro values. A further dosage regimen is 1.5 mg daily for 5 days. A further regimen is illustrated in FIG. 17 which simulates plitidepsin total plasma concentrations associated to an initial flat dose of 1 mg (Day 1) given as a 1-h i.v. infusion, followed by daily doses of 0.5 mg (D2-D5).

Figure 18:
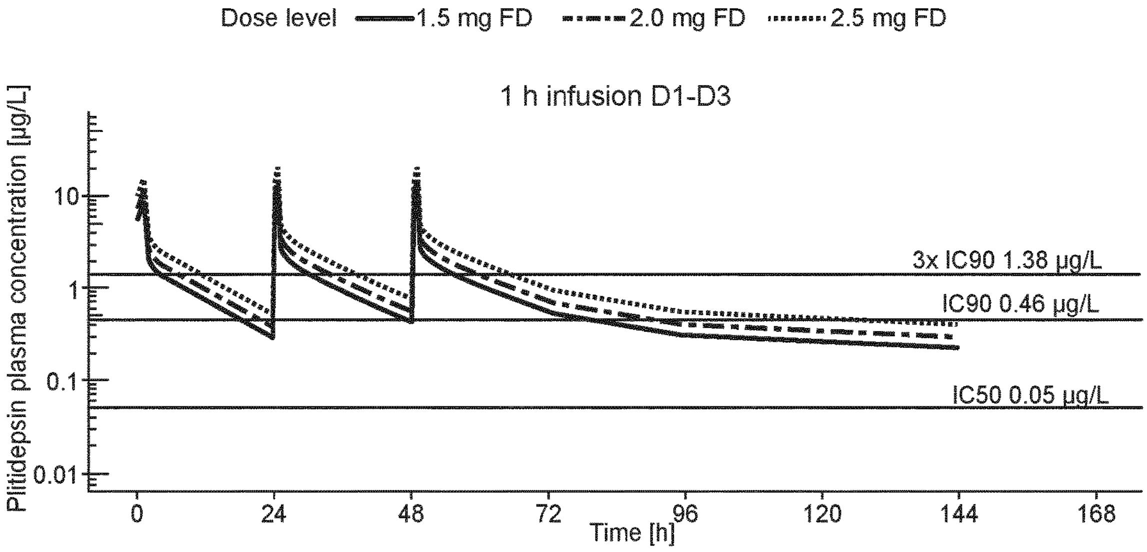
FIG. 18 shows total plasma concentration profiles vs. time predicted for further dosing schedules and administration according to the present invention.

FIG. 18 illustrates the simulation of the total plasma plitidepsin concentration profiles vs. time after a daily dose (D1-D3) of 1.5 mg, 2.0 mg and 2.5 mg. The horizontal black lines represent the total plasma concentrations associated with concentrations in lungs equivalent to exemplary IC50, IC90 and 3×IC90 in vitro values.

Figure 19:
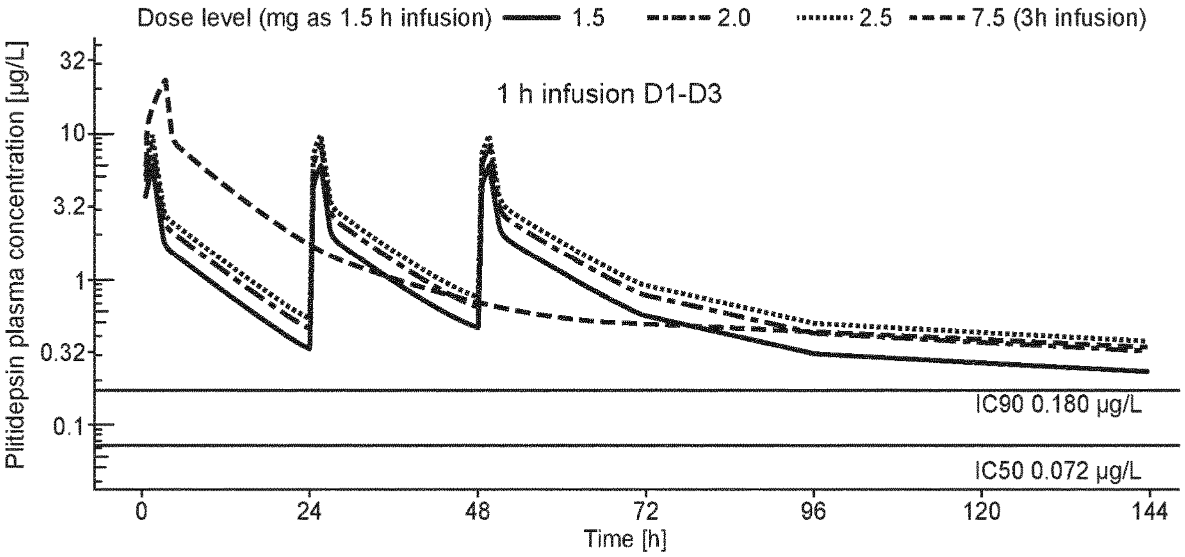
FIG. 19 shows total vs. plasma concentration profiles for single dose plitidepsin 7.5 mg and 1.5, 2.0 and 2.5 mg on day 1 to 3, using a 1.5 hour infusion.

FIG. 19 shows a validated plitidepsin population pharmacokinetic model (Nalda-Molina R, et al. Population pharmacokinetics meta-analysis of plitidepsin (Aplidin) in cancer subjects. Cancer Chemother Pharmacol. 2009 June; 64(1):97-108. doi: 10.1007/s00280-008-0841-4) to confirm total plasma concentration with a single dose.

REFERENCES

Losada A, Berlanga J J, Molina-Guijarro J M, Jiménez-Ruiz A, Gaggo F, Avilés P, de Haro C, Martínez-Leal J F., Generation of endoplasmic reticulum stress and inhibition of autophagy by plitidepsin induces proteotoxic apoptosis in cancer cells. Biochem Pharmacol. 2020 February; 172:113744
Losada A, Muñoz-Alonso M J, García C, Sánchez-Murcia P A, Martínez-Leal J F, Domînguez J M, Lillo M P, Gago F, Galmarini C M., Translation Elongation Factor eEF1A2 is a Novel Anticancer Target for the Marine Natural Product Plitidepsin. Sci Rep. 2016 7; 6:35100
Losada A, Muñoz-Alonso M J, Martínez-Díez M, Gago F, Domínguez J M, Martínez-Leal J F, Galmarini C M., Binding of eEF1A2 to the RNA-dependent protein kinase PKR modulates its activity and promotes tumour cell survival. Br J Cancer. 2018; 119(11):1410-1420
M. D. Vera and M. M. Joullié, Natural products as probes of cell biology: 20 years of didemnin research Med. Res. Rev., 2002, 22, 102
Remington s Pharmaceutical Sciences, 17th Ed., Mack Publishing Company, Easton, Pa., 1995
Stark G. R., Kerr, I. M., Williams, B. R., Silverman, R. H., and Schreiber, R. D., How cells respond to interferons. Annu. Rev. Biochem. 1998, 67: 227-264.
Ranieri V M, Rubenfeld G D, Thompson B T, et al. Acute respiratory distress syndrome: the Berlin Definition. JAMA 2012; 307: 2526-2533.
Losada, A., et al., Translation Elongation Factor eEF1A2 is a Novel Anticancer Target for the Marine Natural Product Plitidepsin. Sci Rep, 2016. 6: p. 35100.
Mateyak, M. K. and T. G. Kinzy, eEF1A: thinking outside the ribosome. J Biol Chem, 2010. 285 (28): p. 21209-13.
PharmaMar, data on file; VPT1992/2014.
PharmaMar, data on file; VPT2678/2014.
Maroun, J. A., et al., Phase I study of Aplidine in a daily×5 one-hour infusion every 3 weeks in patients with solid tumors refractory to standard therapy. A National Cancer Institute of Canada Clinical Trials Group study: NCIC CTG IND 115. Ann Oncol, 2006. 17 (9): p. 1371-8.
Nalda-Molina R, et al. Population pharmacokinetics meta-analysis of plitidepsin (Aplidin) in cancer subjects. Cancer Chemother Pharmacol. 2009 June; 64 (1): 97-108. doi: 10.1007/s00280-008-0841-4.
Kawai T & Akira S (2007); Signaling to NF-κB by Toll-like receptors; Trends in Molecular Medicine; Volume 13, Issue 11, p. 460-469.
Davis W G, Blackwell J L, Shi P Y, Brinton M A. Interaction between the cellular protein eEF1A and the 3-terminal stem-loop of West Nile virus genomic RNA facilitates viral minus-strand RNA synthesis. J Virol. 2007; 81(18): 10172-87.
Suthar M S, Diamond M S, Gale M, Jr. West Nile virus infection and immunity. Nat Rev Microbiol. 2013; 11(2): 115-28.
Rossi S L, Ross™, Evans J D. West Nile virus. Clin Lab Med. 2010; 30(1):47-65.
Rossini G, Landini M P, Gelsomino F, Sambri V, Varani S. Innate host responses to West Nile virus: Implications for central nervous system immunopathology. World J Virol. 2013; 2(2):49-56.
Getts D R, Terry R L, Getts M T, Muller M, Rana S, Shrestha B, et al. Ly6c+ "inflammatory monocytes" are microglial precursors recruited in a pathogenic manner in West Nile virus encephalitis. J Exp Med. 2008; 205(10):2319-37.
Wang T, Town T, Alexopoulou L, Anderson J F, Fikrig E, Flavell R A. Toll-like receptor 3 mediates West Nile virus entry into the brain causing lethal encephalitis. Nat Med. 2004; 10(12):1366-73.
Kumar M, Verma S, Nerurkar V R. Pro-inflammatory cytokines derived from West Nile virus (WNV)-infected SK-N-SH cells mediate neuroinflammatory markers and neuronal death. J Neuroinflammation. 2010:7:73.

The invention claimed is:

1. A method of alleviating progress of a viral infection, wherein the virus is selected from the Orthomyxoviridae family or wherein the virus is West Nile virus, wherein the method comprises administering to an individual in need thereof a therapeutically effective amount of plitidepsin, or a pharmaceutically acceptable salt or stereoisomer thereof.

2. The method according to claim 1, wherein the virus is Orthomyxoviridae virus.

3. The method according to claim 1, wherein the Orthomyxoviridae virus is selected from Influenzavirus A, Influenzavirus B, Influenzavirus C, Thogotovirus, Quaranjavirus, and Isavirus.

4. The method according to claim 3, wherein the Orthomyxoviridae virus is Influenza A; or the Orthomyxoviridae virus is influenza B.

5. The method according to claim 4, wherein the Orthomyxoviridae virus is Influenza A, and is selected from H1N1, H1N2 and H3N2; or the Orthomyxoviridae virus is influenza B, and is selected from the Yamagata or Victoria lineages.

6. The method according to claim 1, wherein the virus is West Nile virus.

7. The method according to claim 1, wherein the compound is administered in combination with a corticosteroid.

8. The method according to claim 7, wherein the corticosteroid is dexamethasone.

9. The method according to claim 7, wherein the compound and corticosteroid are administered concurrently, separately or sequentially.

10. The method according to claim 1, wherein the compound is administered according to a regimen of a daily dose for 10 days, 9 days, 8 days, 7 days, 6 days, 5 days, 4 days, 3 days, 2 days or 1 day.

11. The method according to claim 1, wherein the compound is administered by infusion;

wherein the infusion is a 1 to 3 hour infusion.

12. The method according to claim 1, wherein the compound is administered using a loading dose and a maintenance dose.

13. The method according to claim 12, wherein the dosage regimen is:

a loading dose of 2.5 mg for day 1 of treatment, and followed by a maintenance dose of 2 mg/day for subsequent days;

a loading dose of 2.5 mg for day 1 of treatment, and followed by a maintenance dose of 1.5 mg/day for subsequent days;

a loading dose of 2.5 mg for day 1 of treatment, and followed by a maintenance dose of 1 mg/day for subsequent days;

a loading dose of 2.5 mg for day 1 of treatment, and followed by a maintenance dose of 0.5 mg/day for subsequent days;

a loading dose of 2 mg for day 1 of treatment, and followed by a maintenance dose of 1.5 mg/day for subsequent days;

a loading dose of 2 mg for day 1 of treatment, and followed by a maintenance dose of 1 mg/day for subsequent days;

a loading dose of 2 mg for day 1 of treatment, and followed by a maintenance dose of 0.5 mg/day for subsequent days;

a loading dose of 1.5 mg for day 1 of treatment, and followed by a maintenance dose of 1 mg/day for subsequent days;

a loading dose of 1.5 mg for day 1 of treatment, and followed by a maintenance dose of 0.5 mg/day for subsequent days; or a loading dose of 1 mg for day 1 of treatment, and followed by a maintenance dose of 0.5 mg/day for subsequent days.

14. The method according to claim 1, wherein the compound is administered in combination with a corticosteroid, and wherein the corticosteroid is administered on the same days as administration of the compound.

15. The method according to claim 14, wherein the corticosteroid may also be administered on one or more subsequent days; including wherein the corticosteroid is administered with the compound on days 1-3 of treatment and the corticosteroid is further administered on one or more of days 4-10; and/or wherein the corticosteroid is administered intravenously on days when the compound is administered but is administered by oral administration or IV on subsequent days; and/or wherein the corticosteroid is dexamethasone; including wherein dexamethasone is administered at a dose of 6.6 mg/day IV on days when the compound is administered; and/or wherein dexamethasone is administered at a dose of 6 mg/day oral administration or IV on subsequent days, including one or more of days 4, 5, 6, 7, 8, 9 and 10.

16. The method according to claim 1, wherein the compound is administered as a single dose on day 1 of treatment.

17. The method according to claim 16, wherein the single dose is 1-10 mg; and/or wherein the compound is administered as a 1.5-hour infusion; and/or wherein a corticosteroid is administered using a loading dose and a maintenance dose.

18. The method according to claim 10, wherein the compound is administered according to a regimen of a daily dose for 3, 4, or 5 days.

19. The method according to claim 10, wherein the compound is administered at a dose of 0.5 mg a day to 5 mg a day.

20. The method according to claim 19, wherein the compound is administered at a dose of 1.5 mg/day to 2.5 mg/day.

21. The method according to claim 10, wherein the compound is administered at a total dose of 1-50 mg.

22. The method according to claim 21, wherein the compound is administered at a total dose of 3 to 15 mg.

23. The method according to claim 11, wherein 1.5 to 2.5 mg of plitidepsin is administered as a 1.5-hour infusion, once a day for 3 consecutive days; or wherein 1 to 2 mg of plitidepsin is administered as a 1.5-hour infusion, once a day for 5 consecutive days.

24. The method according to claim 17, wherein the single dose is 4 to 10 mg.

* * * * *